US007427595B1

(12) United States Patent
Zhu et al.

(10) Patent No.: US 7,427,595 B1
(45) Date of Patent: Sep. 23, 2008

(54) USE OF PROEPITHELIN TO PROMOTE WOUND REPAIR AND REDUCE INFLAMMATION

(75) Inventors: Jing Zhu, Menlo Park, CA (US); Aihao Ding, Riverdale, NY (US); Carl Nathan, Larchmont, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 621 days.

(21) Appl. No.: 10/735,289

(22) Filed: Dec. 12, 2003

Related U.S. Application Data

(60) Provisional application No. 60/432,948, filed on Dec. 12, 2002.

(51) Int. Cl.
*A61K 38/16* (2006.01)
*C07K 14/47* (2006.01)

(52) U.S. Cl. .......................................... 514/12; 530/350

(58) Field of Classification Search ........................ None
See application file for complete search history.

(56) References Cited

U.S. PATENT DOCUMENTS 5,290,762 A * 3/1994 Lezdey et al. .................. 514/8

OTHER PUBLICATIONS

Abe, Tatsuya , et al., "Expression of the Secretory leukoprotease Inhibitor Gene in Epithelial Cells", *The Journal of Clinical Investigation, Inc.*, vol. 87, (Jun. 1991),2207-2215.
Ashcroft, Gillian S., et al., "Mice Lacking Smad3 show accelerated wound healing and an impaired local inflammatory response", *Nature Cell Biology*, vol. 1, (1999),260-266.
Ashcroft, Gilliam S., et al., "Secretory leukocyte protease inhibitor mediates non-redundant functions necessary for normal wound healing", *Nature Medicine*, vol. 6, No. 10, (Oct. 2000), 1147-1153.
Baba, Tadashi , et al., "Acrogranin, an Acrosomal Cysteine-Rich Glycoprotein, Is the Precursor of the Growth-Modulating Peptides, Granulins, and epithelins and Is Expressed in Somatic as Well as Male Germ Cells", *Molecular Reproduction and Development 34*, (1993),233-243.
Baggiolini, Marco , et al., "Interleukin-8, a chemotactic and inflammatory cytokine", *FEBS 11242*, vol. 307, No. 1, (Jul. 1992),97-101.
Bateman, Andrew , et al., "Granulins, A Novel Class of Peptide From Leukocytes", *Biochemical and Biophysical Research Communications*, vol. 173, No. 3., (Dec. 31, 1990),1161-1168.
Bateman, A. , et al., "Granulins: the structure and function of an emerging family of growth factors", *Journal of Endocrinology*, 158, (1998),145-151.
Belcourt, Daniel R., et al., "Isolation and Primary Structure of the Three Major Forms of Granulin-like Peptides from Hematopoietic Tissues of a Teleost Fish (Cyprinus carpio)", *The Journal of Biological Chemistry*, vol. 268, No. 13, (May 5, 1993),9230-9237.
Bhandari, Vijay , et al., "Isolation and sequence of the granulin precursor cDNA from human bone marrow reveals tandem cystein-rich granulin domains", *Proc. Natl. Acad. Sci.* USA, vol. 89, (Mar. 1992),1715-1719.

Carp, Harvey , et al., "Inactivation of Bronchial Mucous Proteinase Inhibitor by Cigarette Smoke and Phagocyte-Derived Oxidants", *Experimental Lung Research*, 1, (1980),225-237.
Caughey, George H., "Seriine Proteinases of Mast Cell and Leukocyte Granules (A League of Their Own)", *Am J. Respir Crit Care Med.*, vol. 150, (1994),S138-S142.
Chien, Cheng-Ting , et al., "The two-hybrid system: A method to identify and clone genes for protein that interact with a proteins of interest", *Proc. Natl. Acad. Sci.* USA, vol. 88, (Nov. 1991),9578-9582.
Daniel, Rachel , et al., "Cellular Localization of Gene Expression for Progranulin", *The Journal of Histochemistry & Cytochemistry*, vol. 48(7), (2000),999-1009.
Daiz-Cueto, Laura , et al., "Modulation of Mouse Preimplantation Embryo Development by Acrogranin (Epithelin/Granulin Precursor)", *Developmental Biology*, 217, (2000),406-418.
Drew, Angela F., et al., "Wound-healing defects in mice lacking fibrinogen", *Blood*, vol. 97, No. 12, (Jun. 15, 2001),3691-3698.
Eisenberg, Stephen P., et al., "Location of the Protease-inhibitory Region of Secretory Leukocyte Protease Inhibitor", *the Journal of Biological Chemistry*, vol. 265, No. 14, (May 15, 1990),7976-7981.
Fuortes, Michele, et al., "Role of the tyrosine kinase pyk2 in the integrin-dependent activation of human neutrophils by TNF", *the Journal of Clinical Investigation*, vol. 104, No. 3, (Aug. 1999),327-335.
Grutter, Markus G., et al., "The 2.5 A X-ray crystal structure of the acid-stable proteinase inhibitor from human mucous secretions analysed in its complex with bovine a-chymotrypsin", *The EMBO Journal*, vol. 7, No. 2, (1988),345-351.
He, Zhiheng , et al., "Progranulin (granulin-epithelin precursor, PC-cell-derived growth factor, acrogranin) mediates tissue repair and turmorigenesis", J. Mol: Med., 81, (2003),600-612.
He, Zhiheng , et al., "Progranulin Gene Expression Regulates Epithelial Cell Growth and Promotes Tumor Growth in Vivo", *Cancer Research 59*, (Jul. 1, 1999),3222-3229.
He, Zhiheng , et al., "Progranulin is a mediator of the wound response", *Nature Medicine*, vol. 9, No. 2, (Feb. 2003),225-229.
Helmig, R. , et al., "Secretory leukocyte protease inhibitor in the cervical mucus and in the fetal membranes", *European Journal of Obstetrics & Gynecology and Reproductive Biology*, 59, (1995),95-101.
Hong, Suk J., et al.,"Purification of Granulin-like Polypeptide from the Blood-Sucking Leech, Hirudo nipponia", *Protein Expression and Purification 16*, (1999),340-346.

(Continued)

*Primary Examiner*—Bridget E. Bunner
*Assistant Examiner*—Fozia M Hamud
(74) *Attorney, Agent, or Firm*—Schwegman, Lundberg & Woessner, P.A.

(57) ABSTRACT

The invention is directed to compositions and methods for wound healing and controlling inflammation that involve proepithelin, with or without secretory leukocyte protease inhibitor (SLPI).

46 Claims, 19 Drawing Sheets

OTHER PUBLICATIONS

Hrabal, Richard, et al., "The hairpin stack fold, a novel protein architecutre for a new family of protein growth factors", *Nature Structural Biology*, vol. 3, No. 9, (Sep. 1996),747-752.

Hunt, Thomas K., "Basic Principles of Wound Healing", *The Journal of Trauma*, vol. 30, No. 12 Supplement,(Dec. 1990), S122-S128.

Hutchison, D. C., "The role of proteases and antiproteases in bronchial secretsions", *Eur. J. Respir. Dis*, vol. 71, Suppl. 153,(1987),78-85.

Jin, Fenyu, et al., "Lipopolysaccharide-Related Stimuli Induce Expression of the Secretory Leukocyte Protease Inhibitor, a Macrophage-Derived Lipopolysaccharide Inhibitor", *Infection and Immunity*, (Jun. 1998),2447-2452.

Jin, Fen-Yu, et al., "Secretory Leukocyte Protease Inhibitor: A Macrophage Product Inducted by and Antagonistic to Bacterial Lipopolysaccharide", *Cell*, vol. 88, (Feb. 7, 1997),417-426.

Lee, Chul H., et al., "Distribution of Secretory Leukoprotease Inhibitor in the Human Nasal Airway", *Am. Rev. Respir. Dis*., vol. 147, (1993),710-716.

Martin, Paul, "Wound Healing—Aiming for Perfect Skin Regeneration", *Science*, vol. 276, (Apr. 4, 1997),75-81.

McElvaney, N. G., et al., "Modulation of Airway Inflammation in Cystic Fibrosis", *The Journal of Clinical Inivestigation, Inc.*, vol. 90, (Oct. 1992),1296-1301.

Mellet, Philippe, et al., "Mapping the Heparin-Binding Site of Mucus Proteinase Inhibitor", *Biochemistry*, 34, (1995),2645-2652.

Nathan, Carl, et al., "Cytokine-induced Respiratory Burst of Human Neutrophils: Dependency on Extracellular Matrix Proteins and CD11/CD18 Integrins", *The Journal of Cell Biology*, vol. 109, (Sep. 1989),1341-1349.

Ohlsson, Kjell, et al., "Secretory Leucocyte Protease Inhibitor in the Male Genital Trract: PSA-Induced Proteolytic Processing in Human Semen and Tissue Localization", *Journal of Andrology*, vol. 16, No. 1, (Jan. 2, 1995),64-74.

Ong, C.H.P., et al., "Progranulin (Granulin-epithelin precursor, PC-cell derived growth factor, Acrogranin) in proliferation and tumorigenesis", *Histol Histopathol*, 18, (2003),1275-1288.

Park, Pyong W., et al., "Cell Surface Heparan Sulfate Proteoglycans: Selective Regulators of Ligand-Receptor Encounters", *The Jouranl of Biological Chemistry*, vol. 275, No. 39, (Sep. 29, 2000),29923-29926.

Plowman, Gregory D., et al., "The Epithelin Precursor Encodes Two Proteins with Opposing Activities on Epithelial Cell Growth", *The Journal of Biological Chemistry*, vol. 267, No. 18, (Jun. 25, 1992),13073-13078.

Romer, John, et al., "Impaired Wound Healing in Mice with a Disrupted Plasminogen Gene", *Nature Medicine*, vol. 2, No. 3, (Mar. 1996),287-292.

Sallenave, Jean-Michel, et al., "Secretory Leukocyte Proteinase Inhibitor is a Major Leukocyte Elastase Inhibitor in Human Neutrophils", *Journal of Leukocyte Biology*, vol. 61, (Jun. 1997),695-702.

Shoyab, Mohammed, et al., "Epithelins 1 and 2: Isolation and characterization of two cysteine-rich growth-modulating proteins", *Proc. Natl. Acad. Sci USA*, vol. 87, (Oct. 1990),7912-7916.

Singer, Adam J., et al., "Cutaneous Wound Healing", *The New England Journal of Medicine*, (1999),738-746.

Somorin, Oyin, et al., "The Action of Trypsin on Synthetic Chromogenic Arginine Substrates", *J. Biochem*, 85, (1978),157-162.

Song, Xiao-Yu, et al., "Secretory Leukocyte Protease Inhibitor Suppresses the Inflammation and Join Damage of Bacterial Cell Wall-induced Arthritis", *The Journal of Experimental Medicine*, vol. 190, No. 4, (Aug. 16, 1999),535-542.

Sparro, Giulia, et al., "Isolation and N-Terminal Sequence of Multiple Forms of Granulins in Human urine", *Protein Expression and Purificaiton 10*, (1997),169-174.

Thompson, Robert C., et al., "Isolation, Properties, and Complete Amino Acid Sequence of Human Secretory Leukocyte Protease Inhibitor, a Potent Inhibitor of Leukocyte Elastase", *Proceedings of the National Academy of Sciences of the United States of America*, vol. 83, No. 18, (1986),6692-6696.

Van Wetering, Sandra, et al.,"Regulation of SLPI and elafin release from bronchial epithelial cells by neutrophil defensins", *Am. J. Physiol. Lung Cell. Mol. Physiol*., 278, (2000),L51-L58.

Wahl, Sharon M., et al.,"Anatomic Dissociation Between HIV-1 and Its Endogenous Inhibitor in Mucosal Tissues", *American Journal of Pathology*, vol. 150, No. 4., (Apr. 1997),1275-1284.

Witte M.D., Maria B., et al., "Wound Healing (General Principles of Wound Healing)", *Surgical Clinics of North America*, vol. 77, No. 3, (Jun. 1997),509-528.

Wright, Clifford D., et al., "Inhibition of Murine Neutrophil Serine Porteinases by Human and Murine Secretory Leukocyte Protease Inhibitor", *Biochemical and Biophysical Research Communications*, 254, (1999),614-617.

Xia, Xianmin, et al., "Identification of Cell Surface Binding Sites for PC-Cell-Derived Growth Factor, PCDGF, (Epithelin/Granulin Precursor) on Epithelial Cells and Fibroblasts", *Biochemical and Biophysical Research Communications*, 245, (1998),539-543.

Xu, Shi-Qiong, et al., "The Granulin/Epithelin Precursor Abrogates the Requirement for the Insulin-like Growth Factor 1 Receptor for Growth in Vitro", *the Journal of Biological Chemistry*, vol. 273, No. 32, (Aug. 7, 1998),20078-20083.

Ying, Qi-Long, et al., "Functions of the N-Terminal Domain of Secretory Leukoprotease Inhibitor", *Biochemistry*, 33, (1994),5445-5450.

Zanocco-Marani, Tommaso, et al., "Biological Activities and Signaling Pathways of the Granulin/Epithelin Precursor", *Cancer Research 59*, (1999),5331-5340.

Zhang, Haidi, et al., "Inhibition of tumorigenicity of the teratoma PC cell line by transfection with antisense cDNA for PC cell-derived growth factor (PCDGF, epithelin/granulin precursor)", *Proc. Natl. Acad. Sci. USA*, vol. 95, (Nov. 1998), 14202-14207.

Zhang, Yahong, et al., "Secretory Leukocyte Protease Inhibitor Suppresses the Production of Monocyte Prostaglandin H Synthase-2, Prostaglandin E2, and Matrix Metalloproteinases", *The Journal of Clinical Investigation*, vol. 99, No. 5, (Mar. 1997),894-900.

Zhou, Jian, et al., "Purification of an Autocrine Growth Factor Homologous with Mouse Epitheliin Precursor from a Highly Tumorigenic Cell Line", *The Journal of Biological Chemistry*, vol. 268, No. 15, (May 25, 1993),10863-10869.

Zhu, Jing, et al., "Suppression of macrophage responses to bacterial lipopolysaccharide by a non-secretory form of secretory leukocyte protease inhibitor", *Biochimica et Biophysica Acta 1451*, (1999),219-223.

Zitnik, Ralph J., et al., "The Cloning and Characterization of a Murine Secretory Leukocyte Protease Inhibitor cDNA", *Biochemical and Biophysical Research Communications 232*, (1997),687-697.

"The Lowdown on High Blood Sugar by Jerry Ryan, Ph.d", http://www.flickergaming.net/the-lowdown-on-high-blood-sugar-by-jerry-ryan—ph-d.html, (Downloaded Jan. 31, 2008),5 pgs. pp. 1-5.

Angelov, Nikola, et al., "Aberrant mucosal wound repair in the absence of secretory leukocyte protease inhibitor", *Thrombosis and Haemostasis*, 92(2), (2004),288-297.

Brunner, Georg, "Dr. Jekyll and Mr. Hyde: the many faces of wound healing regulators.", *Thrombosis and Haemostasis*, 92(2), (2004),232-233.

Shimoya, Koichiro, et al., "Secretory leukocyte protease inhibitor levels in cervicovaginal secretion of elderly women", *The European Menopause Journal*, 54(2), (2006),141-148.

Shugars, D. C., et al., "Salivary concentration of secretory leukocyte protease inhibitor, an antimicrobial protein, is decreased with advanced age.", *Gerontology*, 47(5), (2001),246-253.

Thuraisingam, Thusanth, et al., "Delayed cutaneous wound healing in mice lacking solute carrier 11a1 (formerly Nramp1): correlation with decreased expression of secretory leukocyte protease inhibitor", *Journal of Investigative Dermatology*, 126(4), (2006),890-901.

\* cited by examiner

SLPI
FIG. 1A-A
Preproepithelin
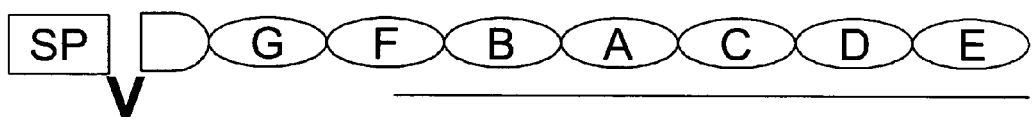
FIG. 1A-B

BamH I and EcoR V digestion

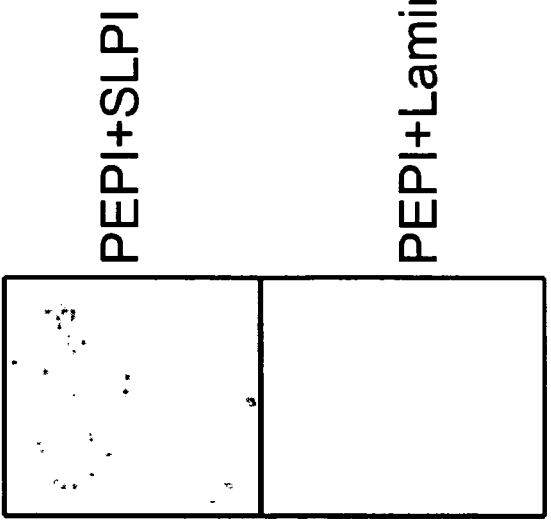
FIG. 1C-B
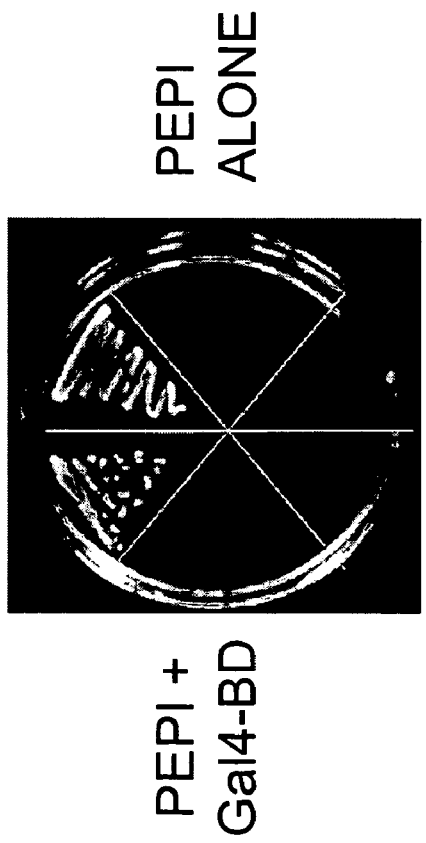
FIG. 1C-A

FIG. 2A-A   FIG. 2A-B

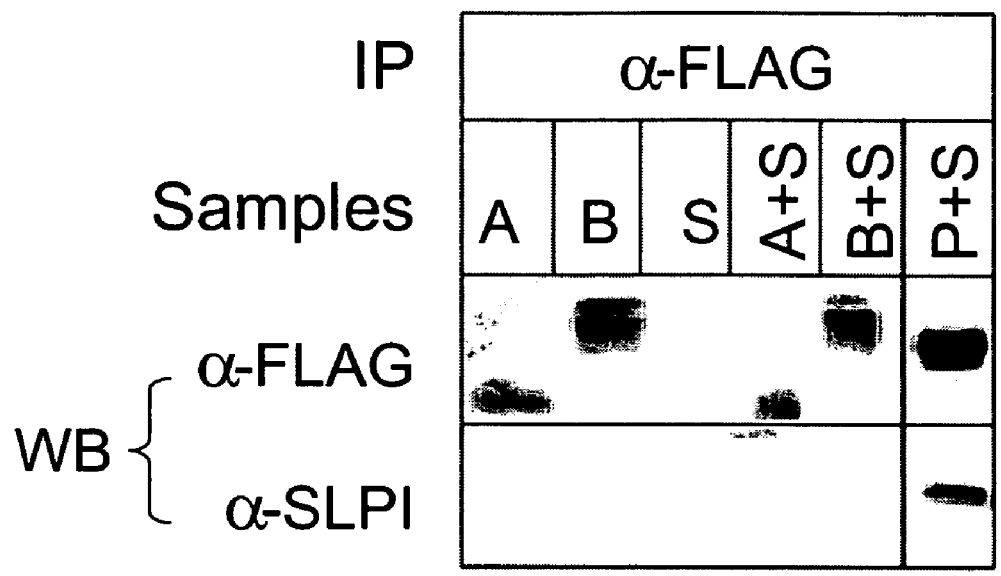
FIG. 2E-A
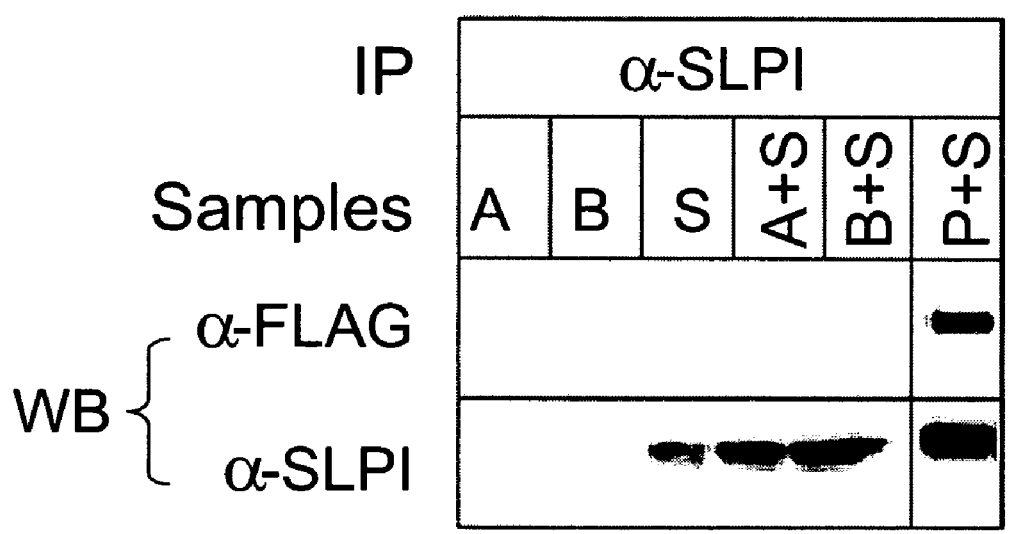
FIG. 2E-B

Human PMN ELASTASE, 0.3 unit/ml

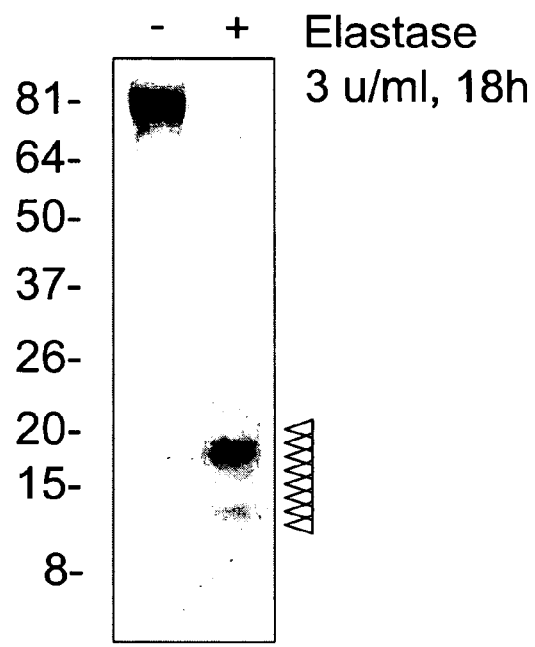
FIG. 3E-A
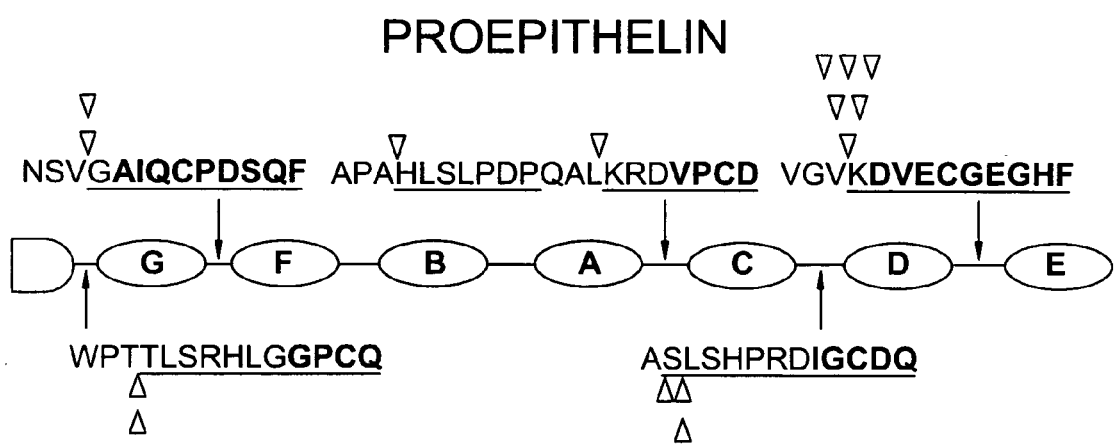
FIG. 3E-B

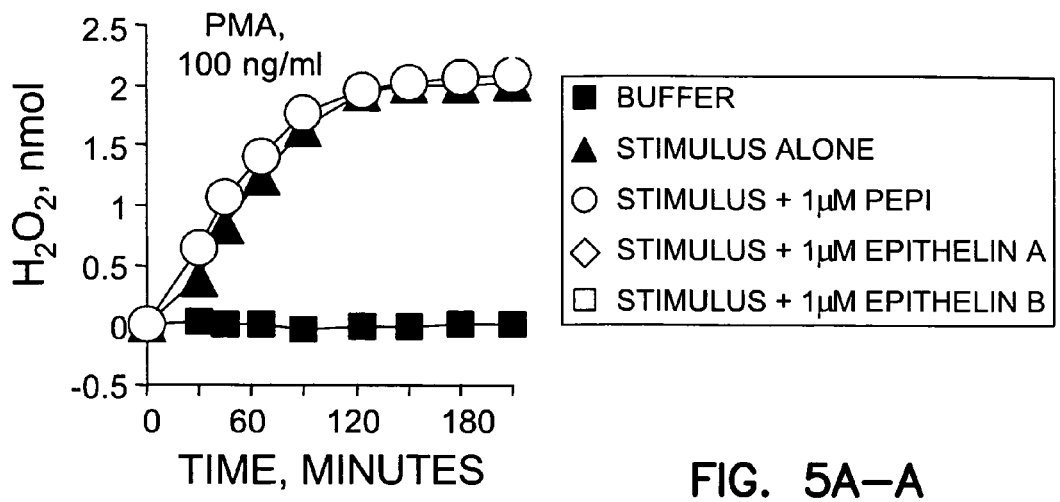
FIG. 5A-A
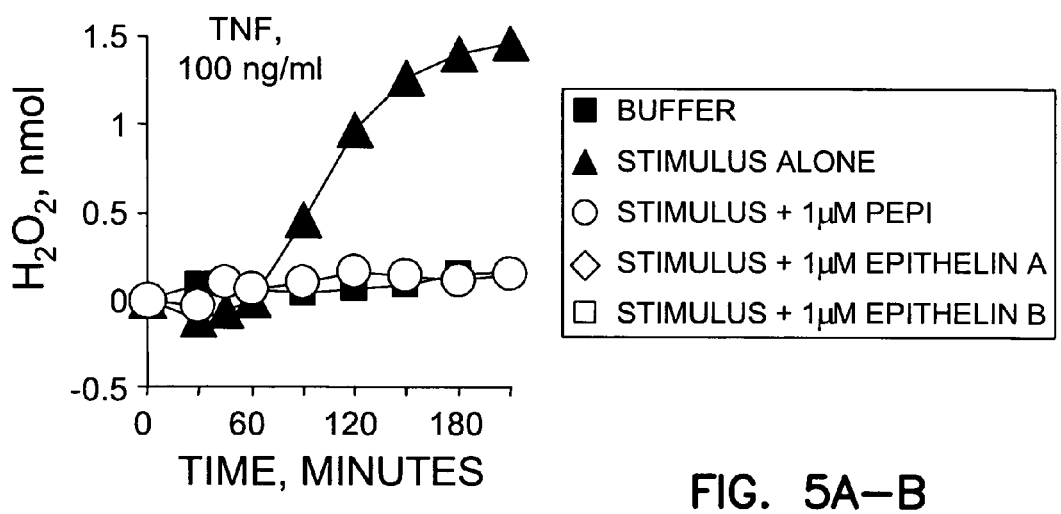
FIG. 5A-B
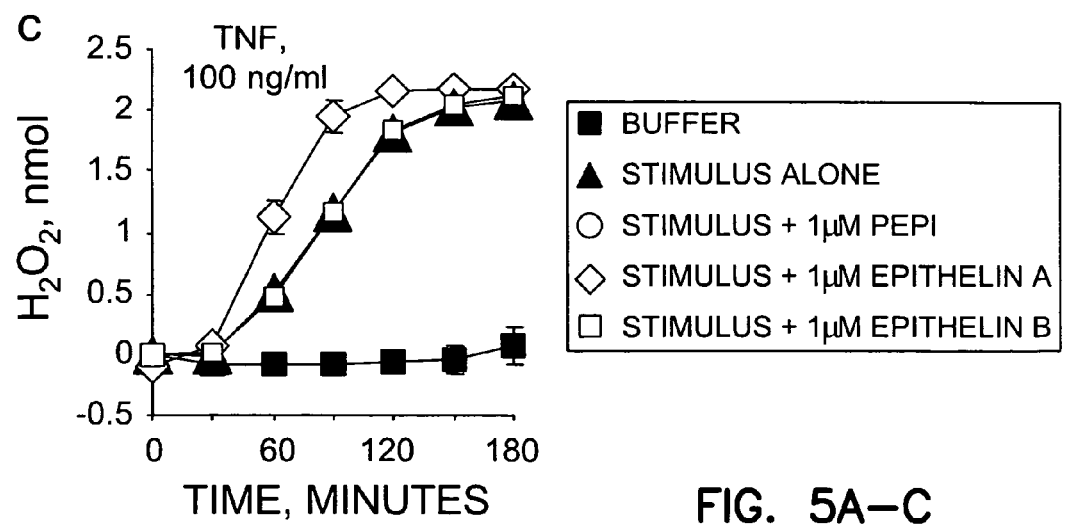
FIG. 5A-C

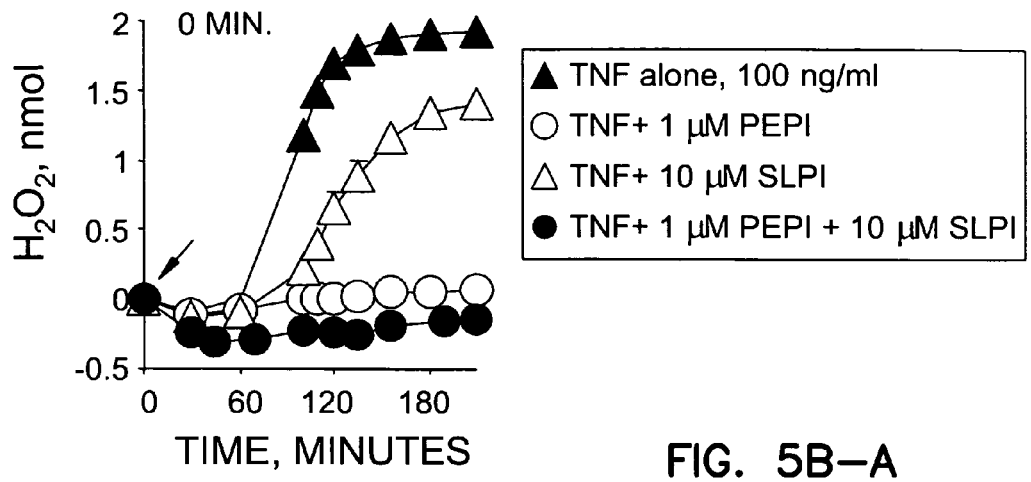
FIG. 5B-A
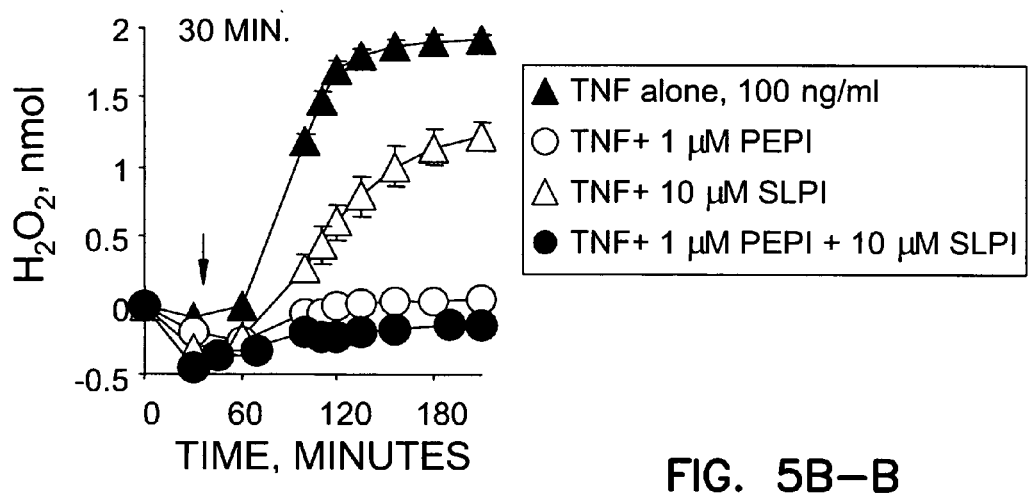
FIG. 5B-B
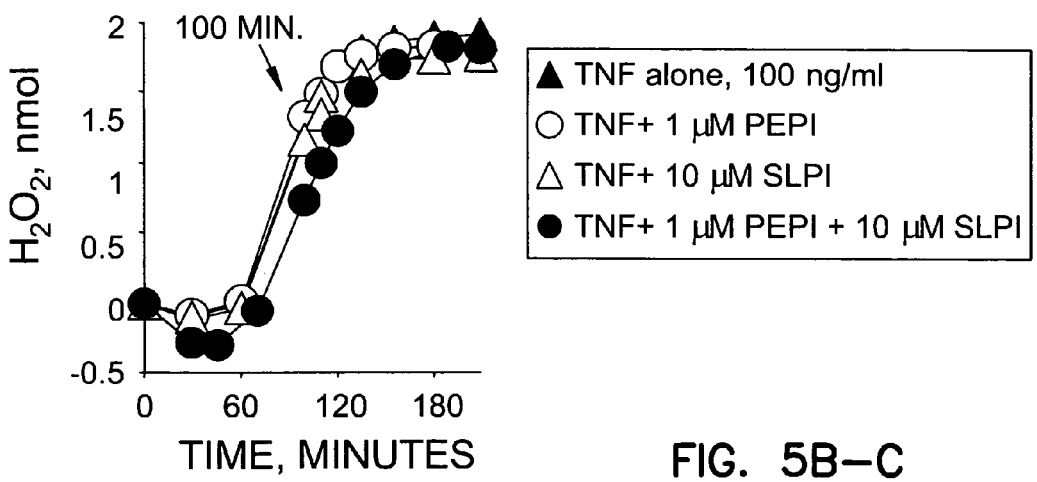
FIG. 5B-C

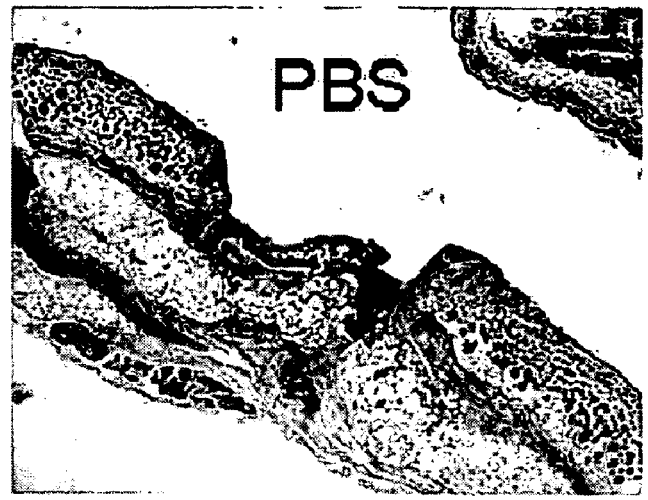
FIG. 7C-A
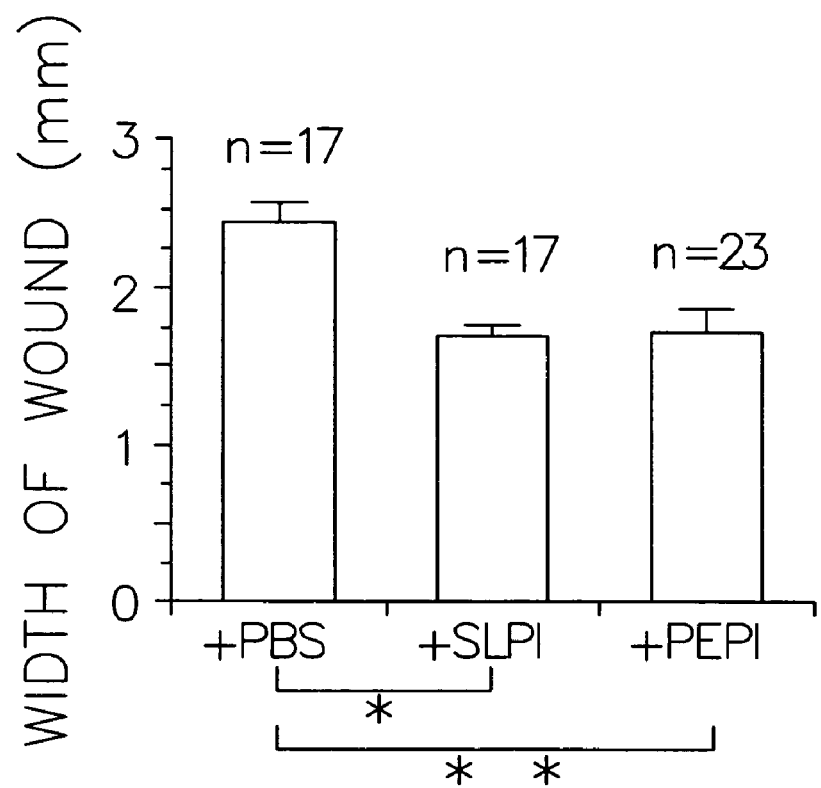
FIG. 7C-B

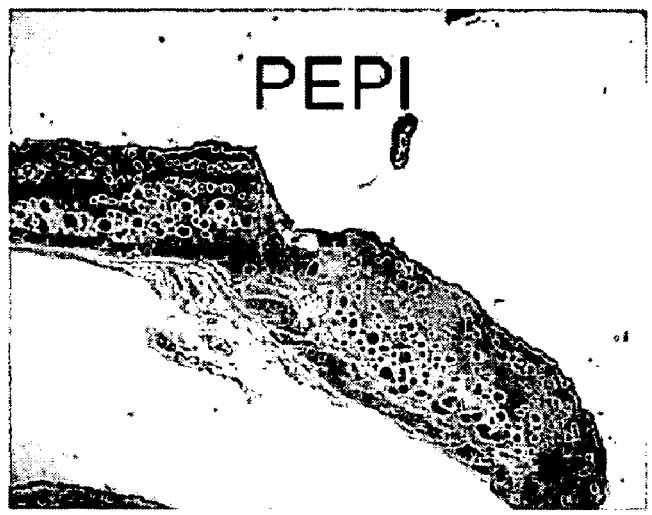
FIG. 7C-C
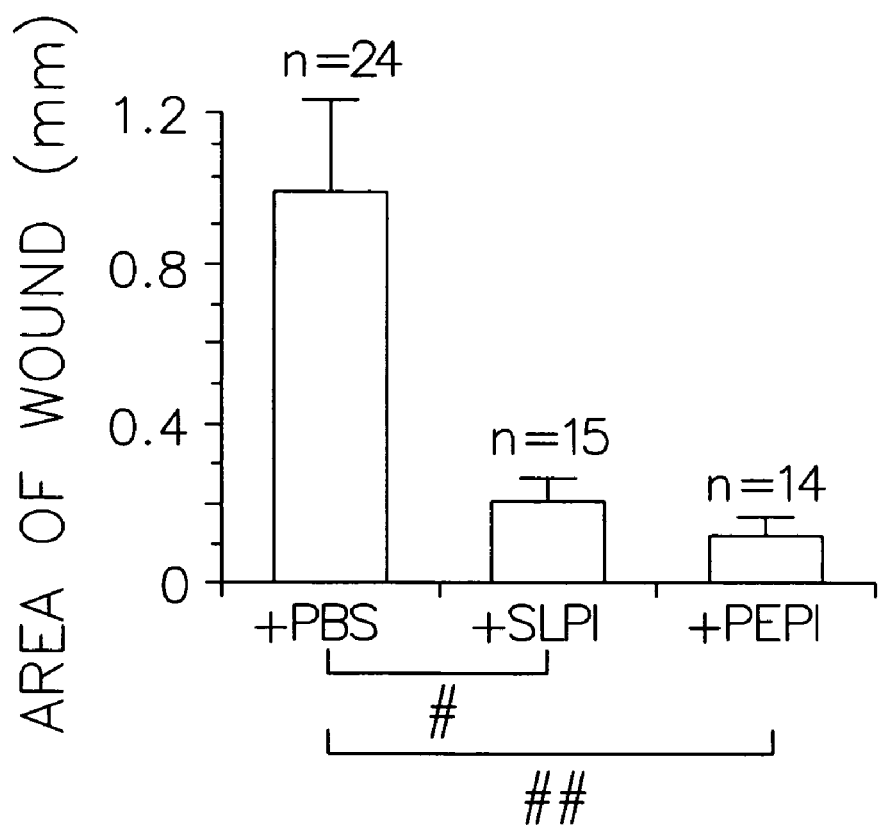
FIG. 7C-D

USE OF PROEPITHELIN TO PROMOTE WOUND REPAIR AND REDUCE INFLAMMATION

This application claims priority to U.S. Provisional Application Ser. No. 60/432,948 filed Dec. 12, 2002.

GOVERNMENT FUNDING

The invention described herein was developed with the support of the National Institutes of Health, grant numbers RO1 GM61710 and RO1 A46382. The United States Government has certain rights in the invention.

FIELD OF THE INVENTION

The invention relates to compositions and methods for wound healing that involve the use of proepithelin.

BACKGROUND OF THE INVENTION

Skin is probably the organ most subject to injury. The breach of epithelium triggers tissue mast cells, recruits leukocytes from the blood and stimulates the production of cytokines that activate them. Host survival requires that leukocytes sterilize the wound and that epithelium closes it. However, the antimicrobial molecules released by leukocytes—oxidants, proteases and antimicrobial peptides—can be inimical to epithelial cell survival and proliferation. Control mechanisms must exist that coordinate the phasing of otherwise incompatible actions by diverse host cells in a wound (Martin, 1997; Singer and Clark, 1999).

However, skin repair is a complex process. The process of skin repair can be divided into four phases usually described as inflammation, granulation tissue formation, epithelialization and remodeling of the connective tissue matrix. Each of these phases is complex in itself, and it is clear that for good wound healing, the processes must occur successively and in coordination. Good wound healing can be defined as restoration of the skin, including the dermal and epidermal part, in such a way that the resulting scar tissue maximally resembles the unwounded skin structurally, histologically, functionally, and esthetically obviously, such scar tissue is different from a hypertrophic scar or keloid.

The skin is composed of several sections including the epidermis and dermis, which can be divided into different layers. The upper section is the epidermis, which contains mostly keratinocyte or epithelial cells, some melanocytes and Langerhans cells, and several Merkel cells. Five different layers are found in the epidermis, reflecting the state of keratinization. Proliferating keratinocytes are located at the base of the epidermis, within the stratum basal, and are attached to the dermis via the basement membrane. The dermis is composed of connective tissue, including fibroblasts and other connective tissue cells, and connective tissue matrix substances. Blood vessels, nerves, sensory organs, sweat glands, sebaceous glands, and hair follicles are present in the dermis.

Increased leukocyte elastase activity in mice lacking secretory leukocyte protease inhibitor (SLPI) leads to impaired wound healing due to enhanced activity of TGFb and perhaps other factors. Workers have some data indicating that proepithelin (PEPI) appears to be an epithelial growth factor that can be converted to epithelins (EPIs) in vivo. However, mechanism(s) of this conversion and the consequences thereof are unknown.

Given the complexity of wound healing, further information is needed on the processes by which such healing occurs. Moreover, new therapies for wound healing, particularly of chronic wounds, are needed.

SUMMARY OF THE INVENTION

According to the invention, supplying proepithelin corrects the wound-healing defect in SLPI-null mice. Secretory leukocyte protease inhibitor and proepithelin form complexes preventing elastase from converting proepithelin to epithelins. Moreover, as provided herein, proepithelin and epithelin exert opposing activities. Epithelins inhibit the growth of epithelial cells but induce them to secrete the neutrophil attractant IL-8, while proepithelin blocks neutrophil activation by tumor necrosis factor, preventing release of oxidants and proteases. Thus, proepithelin can inhibit inflammation and promote healing of wounds.

Hence, in one embodiment, the invention provides compositions and methods for healing wounds that employ proepithelins. For example, the invention provides a therapeutic method for enhancing wound healing in a mammal afflicted with a wound that involves administering an effective amount of a composition comprising proepithelin (PEPI) or a subunit thereof to the mammal. The composition can also include secretory leukocyte protease inhibitor or a subunit thereof.

In other embodiments, the invention provides compositions and methods for inhibiting release of cytotoxic oxidants from neutrophils that employ proepithelins. For example, the invention also provides a therapeutic method for inhibiting inflammation in a mammal afflicted with a wound that involves administering an effective amount of a composition comprising proepithelin (PEPI) or a subunit thereof to the mammal.

DESCRIPTION OF THE FIGURES

FIG. 1A-C shows the domains of SLPI and PEPI and illustrates that PEPI binds SLPI in yeast.

FIGS. 1A-A and 1A-B show the protein domains in SLPI and preproepithelin. FIG. 1A-A illustrates that mouse SLPI is composed of a secretory signal peptide (amino acids 1-25), an N-terminal domain (amino acids 26-55) and a C-terminal domain (amino acids 56-131). FIG. 1A-B shows that mouse proepithelin contains a secretory signal peptide (SP, amino acids 1-17) and 7.5 EPI domains, seven of which are designated alphabetically. The fragment identified in the two-hybrid screen described herein is underlined.

FIG. 1B shows that BamHI and EcoR Vdigestion of 27 positive clones revealed 3 fragmentation patterns. The DNA markers (M) are a HinDIII digest of λ DNA and a 123-bp ladder. Sequencing confirmed that 21 of the clones encoded the same partial cDNA from mouse proepithelin that included a 1180 bp of the ORF and 338 bp of the 3' UTR (underlined region in FIGS. 1A-B). An additional clone consisted of a shorter piece of proepithelin cDNA (clone 18 in FIG. 1B).

FIGS. 1C-A and IC-B provide confirmation that proepithelin and SLPI interact in yeast. Fusion of proepithelin (PEPI) and SLPI to GAL4 activation and binding domains (AD and BD), respectively, was compared to a positive control with p53 and SV40-T, as well as to negative controls with PEPI alone and SLPI alone, and non-specific controls with PEPI and Gal-4-BD or PEPI and lamin C. Positive interactions permitted growth without histidine FIG. 1C-A and expression of LacZ (FIG. 1C-B).

FIG. 2A-E show that SLPI interacts with proepithelin but not with epithelins in vitro and in vivo. The abbreviations used in FIGS. 2A-E are: p, plasmid; v, vector; IP, immunoprecipitation; WB, western blot; α-S, anti-SLPI antibody; α-FLAG, antibody to the FLAG-tag that is fused with PEPI.

FIG. 2A-A provides a western analysis showing that recombinant human (H) and mouse (M) proepithelins were expressed in HEK293 cells. FIG. 2A-B shows that both human recombinant EPI A and B were expressed in insect cells. All four proteins were purified from conditioned media.

FIG. 2B shows that mouse SLPI co-immunoprecipitated with mouse PEPI from the conditioned media of co-transfected mammalian cells. The mouse proteins were expressed in COS-1 cells.

FIG. 2C shows that human SLPI co-immunoprecipitated with human PEPI from the conditioned media of co-transfected mammalian cells. Human proteins in were expressed in HEK293 cells.

FIG. 2D shows that SLPI was detected in the PEPI immunoprecipitates from two human bronchoalveolar lavage (BAL) fluids.

FIGS. 2E-A and 2E-B show that SLPI co-immunoprecipitated with PEPI but not with EPI A or B in solutions of the pure recombinant proteins. PEPI, EPI A and EPI B were FLAG-tagged. Samples employed were as follows: A, human EPI A; B, human EPI B; S, human SLPI; P, human PEPI.

FIG. 3A-E illustrate that SLPI prevents conversion of proepithelin (PEPI) to EPIs by elastase.

FIG. 3A shows that selected serine proteinases cleave PEPI. An anti-FLAG western blot of recombinant mouse PEPI (100 ng/lane) was incubated with elastase (0.3 U/ml), chymotrypsin (12.5 µg/ml), cathepsin G (0.1 U/ml) or trypsin (1.25 µg/ml) for the indicated times. The term "Fold Enzymes" is used to identify multiples of the indicated proteinase concentrations. The Ki is the reported inhibitory constant of mouse SLPI for the indicated proteinase (Zitnik, et al., 1997).

FIG. 3B shows that SLPI protects PEPI from proteolysis as detected by western analysis. Either human or mouse SLPI inhibits proteolysis of mouse PEPI (100 ng/lane) by elastase. Samples were incubated at 37° C. for 30 min and western blotted with anti-FLAG antibody.

FIG. 3C shows that wild type and mutant SLPI protect PEPI from proteolysis. Mutant SLPI lacking anti-elastase activity (at a concentration of 2 µM) inhibits elastase-mediated proteolysis of PEPI but not of mouse brain tubulin. Proepithelin or tubulin (100 ng/lane) was incubated with 0.1 U/ml of human elastase with the indicated reagents at 37° C. for 15 min and western blotted with anti-PEPI or anti-tubulin antibody. Abbreviations: SLPIwt, wild type human SLPI (40 nM); SLPIL72K, human SLPI Leu72Lys mutant (2 µM); BSA, bovine serum albumin (2 µM).

FIG. 3D shows that elastase cleaves PEPI but not EPIs. Pure recombinant human EPI A and B (5 µg each) were resistant to digestion by elastase (37° C., 60 min), but pure recombinant PEPI (5 µg) was cleaved to discrete fragments as revealed by SDS-PAGE followed by Coomassie blue staining.

FIG. 3E shows that elastase cleaves PEPI within inter-EPI linkers. N-terminal sequences of the indicated PEPI fragments were determined by automated Edman degradation and are shown to the right of the western blot. Arrows indicate cleavage sites, all of which were in inter-EPI linkers. Each arrowhead marks the cleavage site that generated the N-terminus of an individual polypeptide. The identified N-terminal sequences of elastase fragments are underlined. Residues contained in EPI domains as purified from natural sources are in bold. The sequences present in this Figure are SEQ D NOs 28, 29 30, 31, and 32.

FIG. 4A-D shows the contrasting effects of PEPI and EPI B on epithelial cell proliferation and chemokine release. Results are means ±SEM for triplicate cultures in one representative experiment of three performed (A, B and C). Some error bars fall within the symbols.

FIGS. 4A-A and 4A-B illustrate concentration-dependent stimulation of A549 (4A-A) and SW-13 (4A-B) cell proliferation by human PEPI.

FIG. 4B illustrates concentration-dependent inhibition of A549 and SW-13 cell proliferation by human EPI B.

FIGS. 4C-A and 4C-B graphically illustrate release of IL-8 from A549 (4C-A) and SW-13 (4C-B) cells in response to EPI B but not PEPI.

FIG. 4D graphically illustrates induction of IL-8 by elastase-digested PEPI. Results are means ±SEM (n=7). *, p<0.03 compared with controls.

FIG. 5A-C illustrates that PEPI and SLPI, but not EPIs, suppress the TNF-induced respiratory burst of adherent human neutrophils. Results are means ±SEM for nmol $H_2O_2$ produced by $1.5 \times 10^4$ cells/well in triplicate cultures in one representative experiment of the 3-6 experiments (A), or 3 experiments (B) and (C) performed. Most error bars fall within the symbols.

FIGS. 5A-A, A-B and A-C show that human PEPI (5A-B) but not EPIs A or B (5A-C) inhibited the respiratory burst triggered by TNF, but had no effect on the respiratory burst triggered by PMA (5A-A). The graphs plot release of $H_2O_2$ (nmol) as a function of time.

FIGS. 5B-A, 5B-B and 5B-C show the effect of delayed addition of PEPI, SLPI or the combination of PEPI+SLPI on the TNF-triggered respiratory burst. The graphs plot release of $H_2O_2$ (nmol) as a function of time. PEPI and/or SLPI were added with TNF (5B-A) or 30 min (5B-B) or 100 min (5B-C) after TNF as marked by the arrows.

FIG. 5C shows SLPI and PEPI augment each other's inhibitory effect on TNF-induced neutrophil activation. The bar graph shown provides cumulative $H_2O_2$ release 120 min after addition of TNF (100 ng/ml), PEPI (0.3 µM) and/or SLPI (3 µM). Results are from one of three similar experiments.

FIG. 6A is a bar graph showing proteinase activity in the conditioned media of neutrophils 180 min after exposure to TNF (100 ng/ml) and/or PEPI (1 µM). Proepithelin inhibited TNF-induced degranulation without affecting cell viability, measured as release of the cytosolic enzyme lactate dehydrogenase (LDH). Total activity corresponded to 1.66 (A490-A600).

FIG. 6B illustrates that the serine protease inhibitor diisopropyl fluorophosphates (DFP) and SLPI both inhibit PEPI degradation by PMA stimulated neutrophils (PMN) (compare lanes 4, 5 and 6). Human Flag-tagged PEPI (100 ng/lane) was incubated with conditioned medium from PMA simulated neutrophils (PMN) at 37° C. for 30 min in the presence of DFP (2 µg/ml) or human SLPI (10 nM). Samples were western blotted with anti FLAG antibody.

FIG. 6C illustrates that neutrophils convert from spherical (a, b) to spread forms (c-f) 60 min after addition of PMA (100 ng/ml) (c, d) or TNF (100 ng/ml) (e, f). PEPI (1 µM) selectively arrested spreading induced by TNF (f). Bar, 10 µm.

FIG. 6D illustrates that PEPI suppresses TNF-induced tyrosine phosphorylation of Pyk2 in neutrophils. Cell lysates (50 µg) from PEPI or ovalbumin (OVA) pretreated (30 min) and TNF-stimulated (45 min) neutrophils were fractionated on SDS-PAGE and western blotted with indicated antibodies.

FIG. 7A-D illustrates the impact of PEPI on wound healing.

FIG. 7A illustrates that there is increased expression of PEPI and SLPI in wounds of wild type mice, and of PEPI in wounds of SLPI knockout (KO) mice. Wounds were collected 3 days after incision and subjected to Northern blot.

FIG. 7B illustrates that healing in a SLPI KO mouse is accelerated when the wounds are treated with PEPI. Wounds treated with SLPI (1 μg) or PEPI (a, 1 μg; b, 5 μg) healed faster than PBS-treated controls.

FIG. 7C-A to 7C-D shows that administration of PEPI improves wound healing in SLPI KO mice. The photomicrographs show sections of the wound lesion obtained 3 days after wounding. The wounds were treated with PBS (control, 7C-A), SLPI (1 μg/site) or PEPI (1 μg/site, 7C-C) as indicated. The bar graphs in FIGS. 7C-B and 7C-D show the width of wound (7C-B) or wound area (7C-D). Means±SEM are shown for the number of wounds indicated. Significance was assessed by ANOVA followed by Fisher's test. *, p=0.001; **, p<0.001; #, p=0.004; ##, p=0.002.

FIG. 7D provides a diagram of the types of interactions exhibited by SLPI, PEPI and elastase relevant to early (host defense; red) and late (host recovery; green) events in wound healing. For simplicity, the roles of other molecules such as TGFβ (Aschroft et al., 1999), plasmin (Romer et al., 1996) and fibrinogen (Drew et al., 2001) are not shown. In the steady state epithelia, SLPI is abundant, elastase-like proteinases are scant, and PEPI is intact. PEPI inhibits the activation of the few neutrophils that find their way into healthy epithelia, and promotes epithelial regeneration to replace cells that are shed. With injury, epithelial cell production of SLPI and PEPI declines. Mast cells and immigrant leukocytes release proteinases that convert PEPI to EPIs. EPIs restrict premature epithelial repair (that is, wound closure before sterilization) while promoting the release of IL-8 or its functional equivalents in the mouse, which elicits the recruitment of more neutrophils to fight infection. Oxidants released by neutrophils inactivate SLPI (Carp and Janoff, 1980), allowing elastase to generate more EPIs. Eventually, exudation of plasma SLPI and the delayed immigration of macrophages (Rappolee and Werb, 1988; Witte and Barbul 1997) that release copious SLPI and PEPI push the PEPI-EPI equilibrium back toward PEPI. Once the concentration of PEPI increases, PEPI prevents neutrophils from discharging cytotoxic, SLPI-inactivating oxidants and PEPI-digesting proteinases and drives epithelial cells into cycle. In such a manner the interaction of SLPI with PEPI can coordinate the innate immune response with the healing of wounds.

DETAILED DESCRIPTION OF THE INVENTION

Figure 1B:
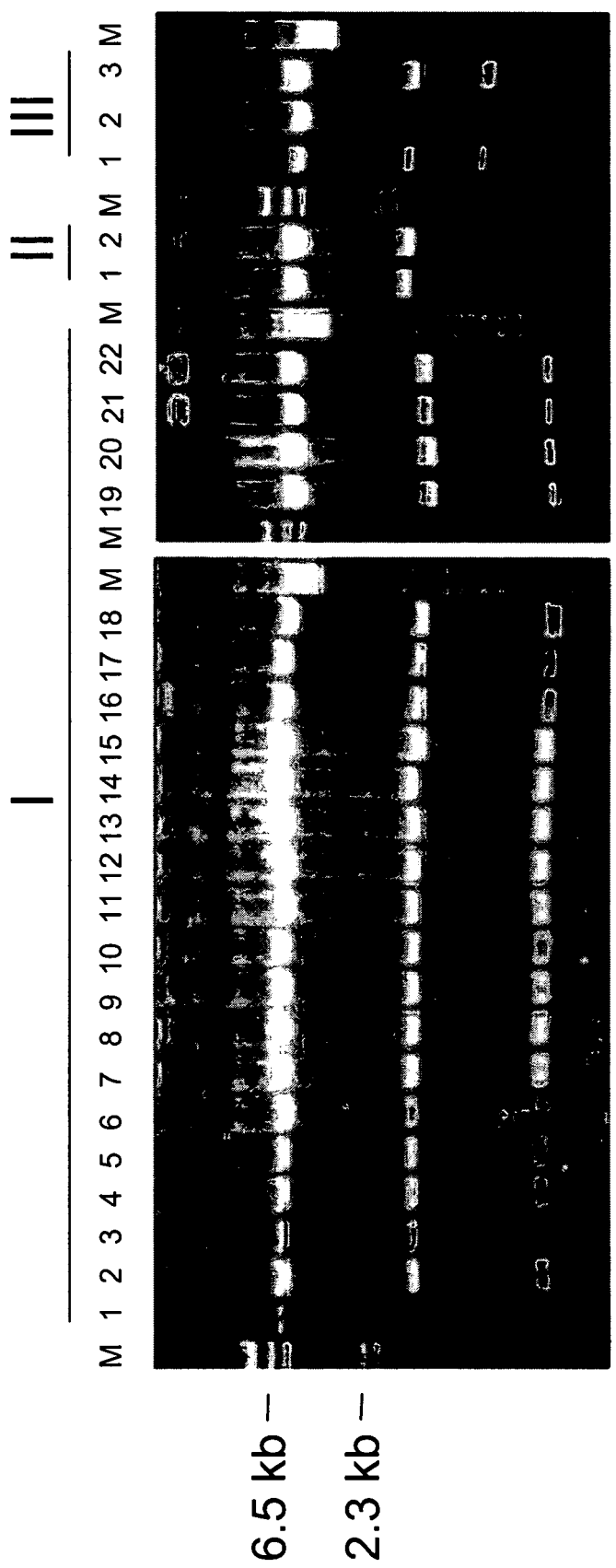

The invention provides compositions and methods for healing wounds. Such compositions and methods employ proepithelins that can enhance wound healing, inhibit neutrophils from discharging cytotoxic, SLPI-inactivating oxidants and PEPI-digesting proteinases and can stimulate epithelial cell proliferation. In other embodiments, the invention provides compositions and methods for inhibiting release of cytotoxic oxidants from neutrophils that employ proepithelins.

Proepithelins and Epithelins

Epithelins (EPIs), or granulins, are a group of seven mutually homologous, 6 kDa peptides, each characterized by the presence of six disulfide bridges. The function of EPIs has been elusive despite their evolutionary conservation in plants, insects, fish, worms and mammals (Avrova et al., 1999; Belcourt et al., 1993; Couto et al., 1992; Hong and Kang, 1999). EPIs have been isolated from diverse tissues and body fluids (Bateman et al., 1990; Belcourt et al., 1993; Shoyab et al., 1990; Sparro et al., 1997).

Proepithelin, also known as progranulin, PC-cell derived growth factor or acrogranin, has been purified from the conditioned media of transformed cell lines as an autocrine growth factor (Baba et al., 1993; Xu et al., 1998; Zhou et al., 1993). Molecular cloning indicates that proepithelin is comprised of one copy of each epithelin plus a half copy of an eighth epithelin, with short peptides linking the EPI domains (Bhandari et al., 1992; Plowman et al., 1992). NMR studies of a carp EPI revealed a compact globular structure, leading to the suggestion that EPIs are strung in proepithelin-like beads on a necklace (Hrabal et al., 1996). A proepithelin convertase was thought to generate the various EPIs post-translationally (Bateman and Bennett, 1998; Bhandari et al., 1992; Plowman et al., 1992). However, until now the enzyme(s) that convert proepithelin to the various epithelins have not been identified. Nor have the conditions or regulatory factors controlling such conversion been identified, or even the effects of such conversion.

Many examples of nucleotide and amino acid proepithelin sequences are available, for example, in the database provided by the National Center for Biotechnology Information (NCBI) (see http://www.ncbi.nlm.nih.gov/). The invention contemplates use of any mammalian proepithelin available to one of skill in the art in the compositions and methods of the invention.

One example of a human sequence for proepithelin is the amino acid sequence at NCBI accession number P28799 (gi: 121617). See website at ncbi.nlm.nih.gov. The amino acid sequence for this proepithelin protein is provided below (SEQ ID NO:1).

1 MWTLVSWVAL TAGLVAGTRC PDGQFCPVAC CLDPGGASYS

41 CCRPLLDKWP TTLSRHLGGP CQVDAHCSAG HSCIFTVSGT

81 SSCCPFPEAV ACGDGHHCCP RGFHCSADGR SCFQRSGNNS

121 VGAIQCPDSQ FECPDFSTCC VMVDGSWGCC PMPQASCCED

161 RVHCCPHGAF CDLVHTRCIT PTGTHPLAKK LPAQRTNRAV

201 ALSSSVMCPD ARSRCPDGST CCELPSGKYG CCPMPNATCC

241 SDHLHCCPQD TVCDLIQSKC LSKENATTDL LTKLPAHTVG

281 DVKCDMEVSC PDGYTCCRLQ SGAWGCCPFT QAVCCEDHIH

321 CCPAGFTCDT QKGTCEQGPH QVPWMEKAPA HLSLPDPQAL

361 KRDVPCDNVS SCPSSDTCCQ LTSGEWGCCP IPEAVCCSDH

401 QHCCPQGYTC VAEGQCQRGS EIVAGLEKMP ARRASLSHPR

441 DIGCDQHTSC PVGGTCCPSL GGSWACCQLP HAVCCEDRQH

481 CCPAGYTCNV KARSCEKEVV SAQPATFLAR SPHVGVKDVE

521 CGEGHFCHDN QTCCRDNRQG WACCPYRQGV CCADRRHCCP

561 AGFRCAARGT KCLRREAPRW DAPLRDPALR QLL

Another example of a human sequence for proepithelin is the amino acid sequence at NCBI accession number NP 002078 (gi: 450-4151). See website at ncbi.nlm.nih.gov. The amino acid sequence for this proepithelin protein is provided below (SEQ ID NO:2).

```
  1 MWTLVSWVAL TAGLVAGTRC PDGQFCPVAC CLDPGGASYS
 41 CCRPLLDKWP TTLSRHLGGP CQVDAHCSAG HSCIFTVSGT
 81 SSCCPFPEAV ACGDGHHCCP RGFHCSADGR SCFQRSGNNS
121 VGAIQCPDSQ FECPDFSTCC VMVDGSWGCC PMPQASCCED
161 RVHCCPHGAF CDLVHTRCIT PTGTHPLAKK LPAQRTNRAV
201 ALSSSVMCPD ARSRCPDGST CCELPSGKYG CCPMPNATCC
241 SDHLHCCPQD TVCDLIQSKC LSKENATTDL LTKLPAHTVG
281 DVKCDMEVSC PDGYTCCRLQ SGAWGCCPFT QAVCCEDHIH
321 CCPAGFTCDT QKGTCEQGPH QVPWMEKAPA HLSLPDPQAL
361 KRDVPCDNVS SCPSSDTCCQ LTSGEWGCCP IPEAVCCSDH
401 QHCCPQGYTC VAEGQCQRGS EIVAGLEKMP ARRASLSHPR
441 DIGCDQHTSC PVGQTCCPSL GGSWACCQLP HAVCCEDRQH
481 CCPAGYTCNV KARSCEKEVV SAQPATFLAR SPHVGVKDVE
521 CGEGHFCHDN QTCCRDNRQG WACCPYRQGV CCADRRHCCP
561 AGFRCAARGT KCLRREAPRW DAPLRDPALR QLL
```

Nucleotide sequences for proepithelin polypeptides from various species are also available, for example, in the database provided by the National Center for Biotechnology Information (NCBI) (see http://www.ncbi.nlm.nih.gov/). One example of a nucleotide sequence for a human proepithelin protein is available at accession number NM 002087 (gi: 450-4150). The nucleic acid sequence for this human SLPI is provided below (SEQ ID NO:3).

```
   1 GTAGTCTGAG CGCTACCCGG TTGCTGCTGC CCAAGGACCG
  41 CGGAGTCGGA CGCAGGCAGA CCATGTGGAC CCTGGTGAGC
  81 TGGGTGGCCT TAACAGCAGG GCTGGTGGCT GGAACGCGGT
 121 GCCCAGATGG TCAGTTCTGC CCTGTGGCCT GCTGCCTGGA
 161 CCCCGGAGGA GCCAGCTACA GCTGCTGCCG TCCCCTTCTG
 201 GACAAATGGC CCACAACACT GAGCAGGCAT CTGGGTGGCC
 241 CCTGCCAGGT TGATGCCCAC TGCTCTGCCG GCCACTCCTG
 281 CATCTTTACC GTCTCAGGGA CTTCCAGTTG CTGCCCCTTC
 321 CCAGAGGCCG TGGCATGCGG GGATGGCCAT CACTGCTGCC
 361 CACGGGGCTT CCACTGCAGT GCAGACGGGC GATCCTGCTT
 401 CCAAAGATCA GGTAACAACT CCGTGGGTGC CATCCAGTGC
 441 CCTGATAGTC AGTTCGAATG CCCGGACTTC TCCACGTGCT
 481 GTGTTATGGT CGATGGCTCC TGGGGGTGCT GCCCCATGCC
 521 CCAGGCTTCC TGCTGTGAAG ACAGGGTGCA CTGCTGTCCG
 561 CACGGTGCCT TCTGCGACCT GGTTCACACC CGCTGCATCA
 601 CACCCACGGG CACCCACCCC CTGGCAAAGA AGCTCCCTGC
 641 CCAGAGGACT AACAGGGCAG TGGCCTTGTC CAGCTCGGTC
 681 ATGTGTCCGG ACGCACGGTC CCGGTGCCCT GATGGTTCTA
 721 CCTGCTGTGA GCTGCCCAGT GGGAAGTATG GCTGCTGCCC
 761 AATGCCCAAC GCCACCTGCT GCTCCGATCA CCTGCACTGC
 801 TGCCCCCAAG ACACTGTGTG TGACCTGATC CAGAGTAAGT
 841 GCCTCTCCAA GGAGAACGCT ACCACGGACC TCCTCACTAA
 881 GCTGCCTGCG CACACAGTGG GGGATGTGAA ATGTGACATG
 921 GAGGTGAGCT GCCCAGATGG CTATACCTGC TGCCGTCTAC
 961 AGTGGGGGGC CTGGGGCTGC TGCCCTTTTA CCCAGGCTGT
1001 GTGCTGTGAG GACCACATAC ACTGCTGTCC CGCGGGGTTT
1041 ACGTGTGACA CGCAGAAGGG TACCTGTGAA CAGGGGCCCC
1081 ACCAGGTGCC CTGGATGGAG AAGGCCCCAG CTCACCTCAG
1121 CCTGCCAGAC CCACAAGCCT TGAAGAGAGA TGTCCCCTGT
1161 GATAATGTCA GCAGCTGTCC CTCCTCCGAT ACCTGCTGCC
1201 AACTCACGTC TGGGGAGTGG GGCTGCTGTC CAATCCCAGA
1241 GGCTGTCTGC TGCTCGGACC ACCAGCACTG CTGCCCCCAG
1281 GGCTACACGT GTGTAGCTGA GGGGCAGTGT CAGCGAGGAA
1321 GCGAGATCGT GGCTGGACTG GAGAAGATGC CTGCCCGCCG
1361 GGCTTCCTTA TCCCACCCCA GAGACATCGG CTGTGACCAG
1401 CACACCAGCT GCCCGGTGGG GCAGACCTGC TGCCCGAGCC
1441 TGGGTGGGAG CTGGGCCTGC TGCCAGTTGC CCCATGCTGT
1481 GTGCTGCGAG GATCGCCAGC ACTGCTGCCC GGCTGGCTAC
1521 ACCTGCAACG TGAAGGCTCG ATCCTGCGAG AAGGAAGTGG
1561 TCTCTGCCCA GCCTGCCACC TTCCTGGCCC GTAGCCCTCA
1601 CGTGGGTGTG AAGGACGTGG AGTGTGGGGA AGGACACTTC
1641 TGCCATGATA ACCAGACCTG CTGCCGAGAC AACCGACAGG
1681 GCTGGGCCTG CTGTCCCTAC CGCCAGGGCG TCTGTTGTGC
1721 TGATCGGCGC CACTGCTGTC CTGCTGGCTT CCGCTGCGCA
1761 GCCAGGGGTA CCAAGTGTTT GCGCAGGGAG GCCCCGCGCT
1801 GGGACGCCCC TTTGAGGGAC CCAGCCTTGA GACAGCTGCT
```

1841 GTGAGGGACA GTACTGAAGA CTCTGCAGCC CTCGGGACCC
1881 CACTCGGAGG GTGCCCTCTG CTCAGGCCTC CCTAGCACCT
1921 CCCCCTAACC AAATTCTCCC TGGACCCCAT TCTGAGCTCC
1961 CCATCACCAT GGGAGGTGGG GCCTCAATCT AAGGCCTTCC
2001 CTGTCAGAAG GGGGTTGTGG CAAAAGCCAC ATTACAAGCT
2041 GCCATCCCCT CCCCGTTTCA GTGGACCCTG TGGCCAGGTG
2081 CTTTTCCCTA TCCACAGGGG TGTTTGTGTG TGTGCGCGTG
2121 TGCGTTTCAA TAAAGTTTGT ACACTTTCAA AAAAAAAAAA
2161 AAAAAAAAAA AAAAAAAA

One example of a mouse sequence for proepithelin is the amino acid sequence at NCBI accession number P28798 (gi: 585216). See website at ncbi.nlm.nih.gov. The amino acid sequence for this proepithelin protein is provided below (SEQ ID NO:4).

1 MWVLMSWLAF AAGLVAGTQC PDGQFCPVAC CLDQGGANYS
41 CCNPLLDTWP RITSHHLDGS CQTHGHCPAG YSCLLTVSGT
81 SSCCPFSKGV SCGDGYHCCP QGFHCSADGK SCFQMSDNPL
121 GAVQCPGSQF ECPDSATCCl MVDGSWGCCP MPQASCCEDR
161 VHCCPHGASC DLVHTRCVSP TGTHTLLKKF PAQKTNRAVS
201 LPFSVVCPDA KTQCPDDSTC CELPTGKYGC CPMPNAICCS
241 DHLHCCPQDT VCDLIQSKCL SKNYTTDLLT KLPGYPVKEV
281 KCDMEVSCPE GYTCCRLNTG AWGCCPFAKA VCCEDHIHCC
321 PAGFQCHTEK GTCEMGILQV PWMKKVIAPL RLPDPQILKS
361 DTPCDDFTRC PTNNTCCKLN SGDWGCCPIP EAVCCSDNQH
401 CCPQGFTCLA QGYCQKGDTM VAGLEKIPAR QTTPLQIGDI
441 GCDQHTSCPV GQTCCPSLKG SWACCQLPHA VCCEDRQHCC
481 PAGYTCNVKA RTCEKDVDFI QPPVLLTLGP KVGNVECGEG
521 HFCHDNQTCC KDSAGVWACC PYLKGVCCRD GRHCCPGGFH
561 CSARGTKCLR KKIPRWDMFL RDPVPRPLL

Another example of a mouse sequence for proepithelin is the amino acid sequence at NCBI accession number NP 032201 (gi: 6680107). See website at ncbi.nlm.nih.gov. The amino acid sequence for this proepithelin protein is provided below (SEQ ID NO:5).

1 MWVLMSWLAF AAGLVAGTQC PDGQFCPVAC CLDQGGANYS
41 CCNPLLDTWP RITSHHLDGS CQTHGHCPAG YSCLLTVSGT
81 SSCCPFSKGV SCGDGYHCCP QGFHCSADGK SCFQMSDNPL
121 GAVQCPGSQF ECPDSATCCl MVDGSWGCCP MPQASCCEDR
161 VHCCPHGASC DLVHTRCVSP TGTHTLLKKF PAQKTNRAVS
201 LPFSVVCPDA KTQCPDDSTC CELPTGKYGC CPMPNAICCS
241 DHLHCCPQDT VCDLIQSKCL SKNYTTDLLT KLPGYPVKEV
281 KCDMEVSCPE GYTCCRLNTG AWGCCPFAKA VCCEDHIHCC
321 PAGFQCHTEK GTCEMGILQV PWMKKVIAPL RLPDPQILKS
361 DTPCDDFTRC PTNNTCCKLN SGDWGCCPIP EAVCCSDNQH
401 CCPQGFTCLA QGYCQKGDTM VAGLEKIPAR QTTPLQIGDI
441 GCDQHTSCPV GQTCCPSLKG SWACCQLPHA VCCEDRQHCC
481 PAGYTCNVKA RTCEKDVDFI QPPVLLTLGP KVGNVECGEG
521 HFCHDNQTCC KDSAGVWACC PYLKGVCCRD GRHCCPGGFH
561 CSARGTKCLR KKIPRWDMFL RDPVPRPLL

One example of a nucleotide sequence for a mouse proepithelin protein is available at accession number NM 008175 (gi: 31982323). The nucleic acid sequence for this human SLPI is provided below (SEQ ID NO:6).

1 GAGATGCCTC CCAGGGAGCC CGGACCCCGA CGCAGGCAGA
41 CCATGTGGGT CCTGATGAGC TGGCTGGCCT TCGCGGCAGG
81 GCTGGTAGCC GGAACACAGT GTCCAGATGG GCAGTTCTGC
121 CCTGTTGCCT GCTGCCTTGA CCAGGGAGGA GCCAACTACA
161 GCTGCTGTAA CCCTCTTCTG GACACATGGC CTAGAATAAC
201 GAGCCATCAT CTAGATGGCT CCTGCCAGAC CCATGGCCAC
241 TGTCCTGCTG GCTATTCTTG TCTTCTCACT GTGTCTGGGA
281 CTTCCAGCTG CTGCCCGTTC TCTAAGGGTG TGTCTTGTGG
321 TGATGGCTAC CACTGCTGCC CCCAGGGCTT CCACTGTAGT
361 GCAGATGGGA AATCCTGCTT CCAGATGTCA GATAACCCCT
401 TGGGTGCTGT CCAGTGTCCT GGGAGCCAGT TTGAATGTCC
441 TGACTCTGCC ACCTGCTGCA TTATGGTTGA TGGTTCGTGG
481 GGATGTTGTC CCATGCCCCA GGCCTCTTGC TGTGAAGACA
521 GAGTGCATTG CTGTCCCCAT GGGGCCTCCT GTGACCTGGT
561 TCACACACGA TGCGTTTCAC CACGGGCAC CCACACCCTA
601 CTAAAGAAGT TCCCTGCACA AAGACCAAC AGGGCAGTGT
641 CTTTGCCTTT TTCTGTCGTG TGCCCTGATG CTAAGACCCA
681 GTGTCCCGAT GATTCTACCT GCTGTGAGCT ACCCACTGGG
721 AAGTATGGCT GCTGTCCAAT GCCCAATGCC ATCTGCTGTT
761 CCGACCACCT GCACTGCTGC CCCCAGGACA CTGTATGTGA
801 CCTGATCCAG AGTAAGTGCC TATCCAAGAA CTACACCACG
841 GATCTCCTGA CCAAGCTGCC TGGATACCCA GTGAAGGAGG

881 TGAAGTGCGA CATGGAGGTG AGCTGCCCTG AAGGATATAC

921 CTGCTGCCGC CTCAACACTG GGGCCTGGGG CTGCTGTCCA

961 TTTGCCAAGG CCGTGTGTTG TGAGGATCAC ATTCATTGCT

1001 GCCCGGCAGG GTTTCAGTGT CACACAGAGA AAGGAACCTG

1041 CGAAATGGGT ATCCTCCAAG TACCCTGGAT GAAGAAGGTC

1081 ATAGCCCCCC TCCGCCTGCC AGACCCACAG ATCTTGAAGA

1121 GTGATACACC TTGTGATGAC TTCACTAGGT GTCCTACAAA

1161 CAATACCTGC TGCAAACTCA ATTCTGGGGA CTGGGGCTGC

1201 TGTCCCATCC CAGAGGCTGT CTGCTGCTCA GACAACCAGC

1241 ATTGCTGCCC TCAGGGCTTC ACATGTCTGG CTCAGGGGTA

1281 CTGTCAGAAG GGAGACACAA TGGTGCTGG CCTGGAGAAG

1321 ATACCTGCCC GCCAGACAAC CCCGCTCCAA ATTGGAGATA

1361 TCGGTTGTGA CCAGCATACC AGCTGCCCAG TAGGGCAAAC

1401 CTGCTGCCCA AGCCTCAAGG GAAGTTGGGC CTGCTGCCAG

1441 CTGCCCCATG CTGTGTGCTG TGAGGACCGG CAGCACTGTT

1481 GCCCGGCCGG GTACACCTGC AATGTGAAGG CGAGGACCTG

1521 TGAGAAGGAT GTCGATTTTA TCCAGCCTCC CGTGCTCCTG

1561 ACCCTCGGCC CTAAGGTTGG GAATGTGGAG TGTGGAGAAG

1601 GGCATTTCTG CCATGATAAC CAGACCTGTT GTAAAGACAG

1641 TGCAGGAGTC TGGGCCTGCT GTCCCTACCT AAAGGGTGTC

1681 TGCTGTAGAG ATGGACGTCA CTGTTGCCCC GGTGGCTTCC

1721 ACTGTTCAGC CAGGGGAACC AAGTGTTTGC GAAAGAAGAT

1761 TCCTCGCTGG GACATGTTTT TGAGGGATCC GGTCCCAAGA

1801 CCGCTACTGT AAGGAAGGGC TACAGACTTA AGGAACTCCA

1841 CAGTCCTGGG AACCCTGTTC CGAGGGTACC CACTACTCAG

1881 GCCTCCCTAG CGCCTCCTCC CCTAACGTCT CCCCGGCCTA

1921 CTCATCCTGA GTCACCCTAT CACCATGGGA GGTGGAGCCT

1961 CAAACTAAAA CCTTCTTTTA TGGAAAGAAG GCTGTGGCCA

2001 AAAGCCCCGT ATCAAACTGC CATTTCTTCC GGTTTCTGTG

2041 GACCTTGTGG CCAGGTGCTC TTCCCGAGCC ACAGGTGTTC

2081 TGTGAGCTTG CTTGTGTGTG TGTGCGCGTG TGCGTGTGTT

2121 GCTCCAATAA AGTTTGTACA CTTTC

According to the invention, proepithelin can bind secretory leukocyte protease inhibitor polypeptides.

Secretory Leukocyte Protease Inhibitor

Secretory leukocyte protease inhibitor (SLPI) is a protein named for its presence in epithelial secretions and its ability to inhibit neutrophil elastase and cathepsin G. SLPI is comprised of two 6-kDa, mutually homologous peptides, each with 4 disulfide bonds, connected by a short linker (Grutter et al., 1988). It was recently discovered that macrophages and neutrophils also produce SLPI (Jin et al., 1997; Sallenave et al., 1997; Song et al., 1999) and that SLPI exerts anti-inflammatory actions on both macrophages (Jin et al., 1997; Zhang et al., 1997; Zhu et al., 1999; Song et al., 1999) and neutrophils (Grobmyer et al., 2000). SLPI circulates in plasma, and the levels rise after injection of endotoxin and during sepsis (Grobmyer et al., 2000). At 12 kDa, SLPI is one of the smallest serine proteinase inhibitors in plasma. This may favor its selective accumulation in tissues, where SLPI appears to constitute the major inhibitory activity toward serine proteinases (Sallenave et al., 1997).

One example of a human sequence for SLPI is the amino acid sequence at NCBI accession number AAH20708 (gi: 18088405). See website at ncbi.nlm.nih.gov. The amino acid sequence for this SLPI protein is provided below (SEQ ID NO:7).

1 MKSSGLFPFL VLLALGTLAP WAVEGSGKSF KAGVCPPKKS

41 AQCLRYKKPE CQSDWQCPGK KRCCPDTCGI KCLDPVDTPN

81 PTRRKPGKCP VTYGQCLMLN PPNFCEMDGQ CKRDLKCCMG

121 MCGKSCVSPV KA

Nucleotide sequences for SLPI polypeptides from various species are available, for example, in the database provided by the National Center for Biotechnology Information (NCBI) (see http://www.ncbi.nlm.nih.gov/). One example of a nucleotide sequence for this human SLPI protein is available at accession number BC020708 (gi: 18088404). The nucleic acid sequence for this human SLPI is provided below (SEQ ID NO:8).

1 AGAGTCACTC CTGCCTTCAC CATGAAGTCC AGCGGCCTCT

41 TCCCCTTCCT GGTGCTGCTT GCCCTGGGAA CTCTGGCACC

81 TTGGGCTGTG GAAGGCTCTG GAAAGTCCTT CAAAGCTGGA

121 GTCTGTCCTC CTAAGAAATC TGCCCAGTGC CTTAGATACA

161 AGAAACCTGA GTGCCAGAGT GACTGGCAGT GTCCAGGGAA

201 GAAGAGATGT TGTCCTGACA CTTGTGGCAT CAAATGCCTG

241 GATCCTGTTG ACACCCCAAA CCCAACAAGG AGGAAGCCTG

281 GGAAGTGCCC AGTGACTTAT GGCCAATGTT TGATGCTTAA

321 CCCCCCCAAT TTCTGTGAGA TGGATGGCCA GTGCAAGCGT

361 GACTTGAAGT GTTGCATGGG CATGTGTGGG AAATCCTGCG

401 TTTCCCCTGT GAAAGCTTGA TTCCTGCCAT ATGGAGGAGG

441 CTCTGGAGTC CTGCTCTGTG TGGTCCAGGT CCTTTCCACC

481 CTGAGACTTG GCTCCACCAC TGATATCCTC CTTTGGGGAA

521 AGGCTTGGCA CACAGCAGGC TTTCAAGAAG TGCCAGTTGA

561 TCAATGAATA AATAAACGAG CCTATTTCTC TTTGCAAAAA
601 AAAAAAAAAA AAAAAAAAAA AAAAA

One example of a mouse sequence for SLPI is the amino acid sequence at accession number NP 035544 (gi:6755574). See website at ncbi.nlm.nih.gov. The amino acid sequence for this mouse SLPI is provided below (SEQ ID NO:9).

1 MKSCGLLPFT VLLALGILAP WTVEGGKNDA IKIGACPAKK
41 PAQCLKLEKP QCRTDWECPG KQRCCQDACG SKCVNPVPIR
81 KPVWRKPGRC VKTQARCMML NPPNVCQRDG QCDGKYKCCE
121 GICGKVCLPP M

One example of a mouse sequence for SLPI is the nucleic acid sequence at accession number NM 011414 (gi: 6755573). See website at ncbi.nlm.nih.gov. The nucleic acid sequence for this mouse SLPI is provided below (SEQ ID NO:10).

1 GGCACGAGGG ATGCCAAACC CCTACCTAAC CAGAAGAAGA
41 GAAGAAAGGC CACTGCCGAG GTCACTTCCA GTACTTGGAG
81 GAGAAAGCAA CGTTCCCATT TACAGCTGAG TAACAGGAGC
121 CACAAGGTAT GTCTGACTCA AAAGTTCAGG CTCTCGATGA
161 CTGTGCGGTG CTGCCCAGTG TGTCTTCTTC AATGTAACCT
201 CAGGACCTAG AACAGCACCT TGCATGTGCT CTCAGGTGGT
241 TACTCTGATG GCCTCATGGT CCTGCCTGAA ACAGAAAGTC
281 TGCCACCTAC TTCTGTAGCA GCAAGACTCC TGTTCTGTGG
321 CTAAGCTTCC TGCCTGTGCA AGAGCCACAG GGAGGGGCCA
361 AATGCATGCC ACTGGGGCCA CGCCTCCTGG TAAAGACATA
401 AATAGTGATC CTCGGGACTG GTCATCAGAG CTCCCCTGCC
441 TTCACCATGA AGTCCTGCGG CCTTTTACCT TTCACGGTGC
481 TCCTTGCTCT GGGGATCCTG GCACCCTGGA CTGTGGAAGG
521 AGGCAAAAAT GATGCTATCA AAATCGGAGC CTGCCCTGCT
561 AAAAAGCCTG CCCAGTGCCT TAAGCTTGAG AAGCCACAAT
601 GCCGTACTGA CTGGGAGTGC CCGGGAAAGC AGAGGTGCTG
641 CCAAGATGCT TGCGGTTCCA AGTGCGTGAA TCCTGTTCCC
681 ATTCGCAAAC CAGTGTGGAG GAAGCCTGGG AGGTGCGTCA
721 AAACTCAGGC AAGATGTATG ATGCTTAACC CTCCCAATGT
761 CTGCCAGAGG GACGGGCAGT GTGACGGCAA ATACAAGTGC
801 TGTGAGGGTA TATGTGGGAA AGTCTGCCTG CCCCCGATGT
841 GAGCCTGATC CCTGACATTG GCGCCGGCTC TGGACTCGTG
881 CTCGGTGTGC TCTGGAAACT ACTTCCCTGC TCCCAGGCGT
921 CCCTGCTCCG GGTTCCATGG CTCCCGGCTC CCTGTATCCC
961 AGGCTTGGAT CCTGTGGACC AGGGTTACTG TTTTACCACT
1001 AACATCTCCT TTTGGCTCAG CATTCACCGA TCTTTAGGGA
1041 AATGCTGTTG GAGAGCAAAT AAATAAACGC ATTCATTTCT
1081 CTATGCAAAA AAAAAAAAAA AAAAAAAAAA AAAAAAAAAA
1121 AAA

SLPI and proepithelin have overlapping tissue distribution. Both are expressed in airway epithelium. SLPI has also been detected in saliva (Thompson and Ohlsson, 1986), cervical (Helmig et al., 1995), nasal and bronchial mucus (Hutchison, 1987; Lee et al., 1993) and seminal fluid (Ohlsson et al., 1995). In situ hybridization has shown that proepithelin is expressed in the epithelia of skin, lung, kidney, uterus and cervix (Daniel et al., 2000). The inventors have confirmed that proepithelin is expressed in human lung and mouse skin. Finally, the inventors have previously cloned both SLPI (Jin et al., 1997) and PEPI (see the Examples) from macrophages.

Interactions between SLPI and Proepithelin

The present invention has identified interactions among three molecules produced by leukocytes and/or epithelial cells: elastase, proepithelin and SLPI. According to the invention, elastase digests proepithelin exclusively in the inter-epithelin linkers and thus may be an important component of a proepithelin convertase. However, when bound with SLPI, proepithelin escapes from elastase-mediated digestion. Moreover, also according to the invention, proepithelin and EPIs exert contrasting effects on neutrophils and epithelial cells. Importantly, proepithelin can replace SLPI in restoring normal wound healing in SLPI knock-out mice.

The invention is therefore also directed to a complex between SLPI and proepithelin. Studies by the inventors also suggest that SLPI most likely binds proepithelin at inter-BPI linker peptides, five of which contain negative charges. Thus, one molecule of PEPI may be decorated or complex with several molecules of SLPI.

In another embodiment, the invention is directed to a composition containing SLPI and proepithelin. Such a composition of SLPI and proepithelin may have any convenient molar ratio of SLPI and proepithelin. Hence, because the inventors have some data indicating that several molecules of SLPI bind to one molecule of proepithelin, the composition can contain more SLPI than proepithelin. In some embodiments, the molar ratio of proepithelin to SLPI is about 1:2, or about 1:3, or about 1:4, or about 1:5, or about 1:6, or about 1:7, or about 1:10.

In other embodiments, it may be desirable to have a larger molar ratio of proepithelin than SLPI. Hence, in some embodiments, the molar ratio of SLPI to proepithelin is about 1:2, or about 1:3, or about 1:4, or about 1:5, or about 1:6, or about 1:7, or about 1:10. Other ratios and concentrations of SLPI and proepithelin may also be employed.

Wound Healing and Inflammation

According to the invention, proepithelin can promote wound healing and reduce inflammation. Hence, the invention provides methods for treating wounds that involve administration of proepithelin to the wound. The invention also provides methods for treating wounds that involve administering proepithelin and SPLI to the wound. In other embodiments, the invention provides methods for treating wounds that involve administration of proepithelin to the wound. The invention also provides methods for treating wounds that involve administering proepithelin and SPLI to the wound.

SLPI-deficient mice exhibit slow or retarded healing. However, as shown herein, when proepithelin is administered wounds in SLPI-deficient mice heal normally (FIG. 7B, C). Proepithelin complexed with SLPI retained the ability to protect extracellular matrix proteins fibronectin, vitronectin and collagen type I from digestion by elastase. The N-terminal domain of SLPI binds glycosaminoglycans (Mellet et al., 1995; Ying et al., 1994) and in this way SLPI may serve as a bridge to localize PEPI to epithelial surfaces. This could augment the bioactivity of PEPI. Binding to epithelial glycosaminoglycans may also position SLPI to protect the glycosaminoglycans from proteolytic shedding during inflammation (Park et al., 2000).

Hence, the invention is also directed to methods for treating wounds in a mammal where SLPI levels may be, or are suspected of being, depressed. The invention is further directed to methods for treating inflammation in a mammal where SLPI levels may be, or are suspected of being, depressed. Such methods involve administration of proepithelin to the wound. In some embodiments, a combination of SLPI and proepithelin can be administered.

Proepithelin potently and specifically inhibited TNF-induced signal transduction in neutrophils thereby blocking cell spreading, Pyk2 tyrosine phosphorylation, oxidant production and proteinase release. Proepithelin has also been shown to promote the proliferation of epithelial cells (FIG. 4A)(He and Bateman, 1999; Xu et al., 1998; Zhang and Serrero, 1998; Zhou et al., 1993). Hence, proepithelin antagonizes inflammation and promotes re-epithelialization and wound healing.

Figure 7A:
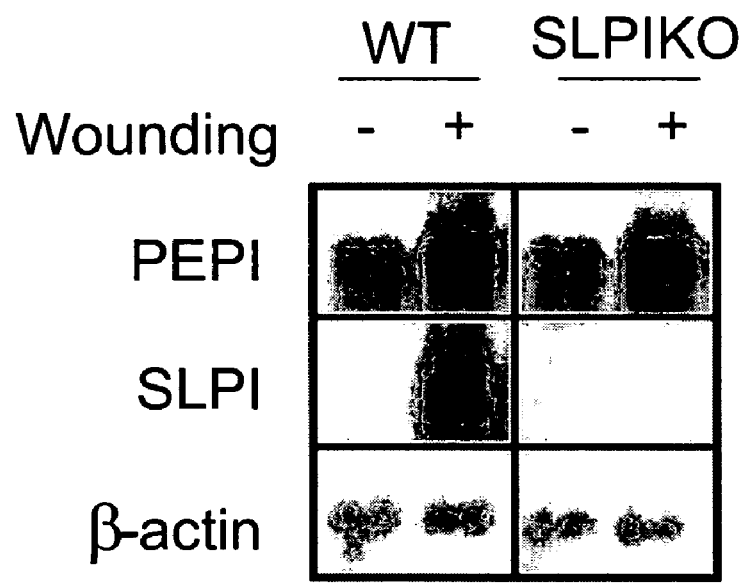
Figure 7B:
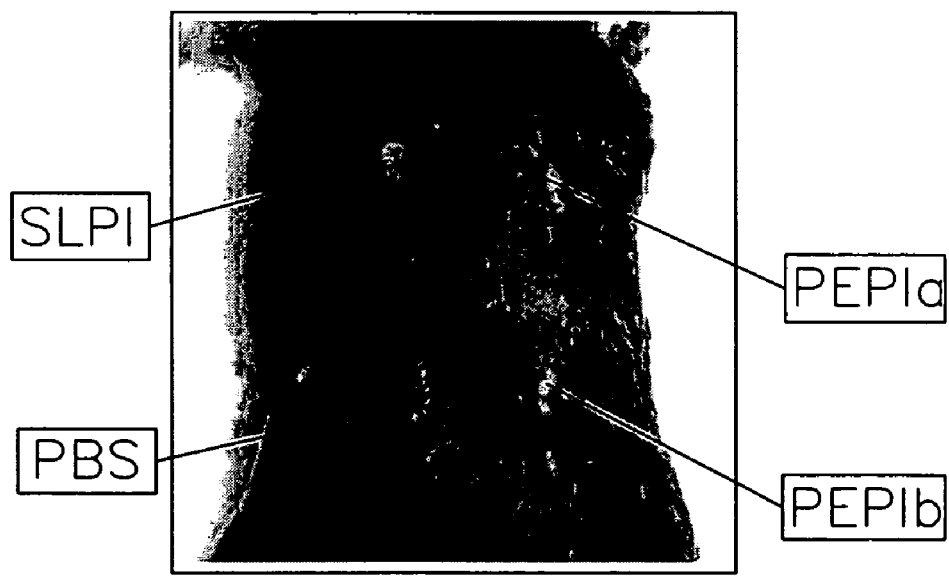
Figure 7D:
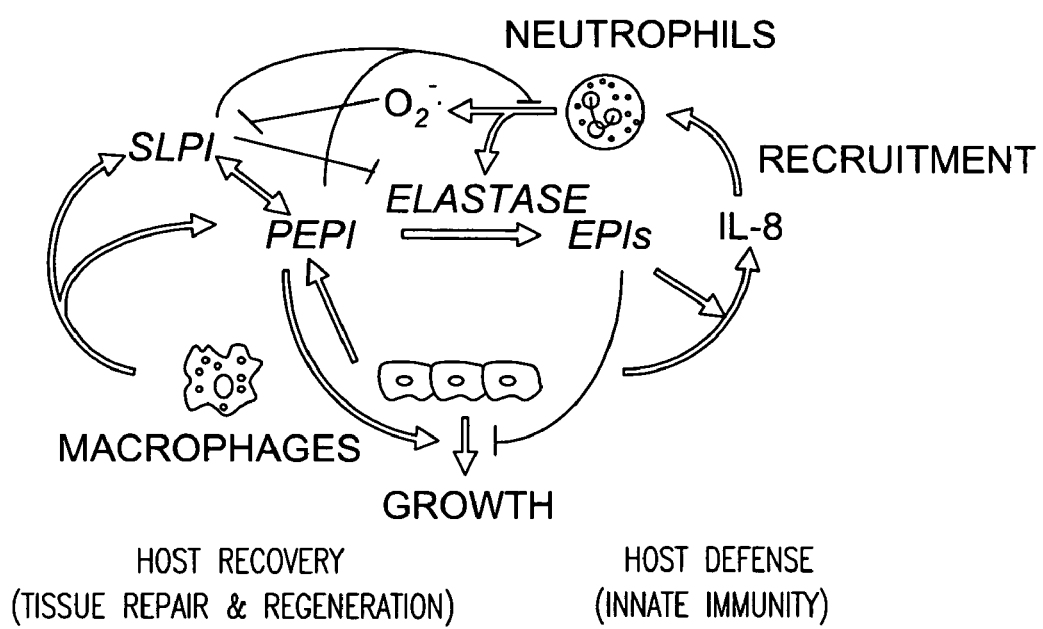

FIG. 7D summarizes the interactions that may exist between several factors within the epithelium and during wound healing. Not all factors that are known to be involved in wound healing are shown. In epithelia in the steady state, SLPI is abundant, elastase-like proteinases are scant, and proepithelin is intact. Proepithelin inhibits the activation of the few neutrophils that find their way into healthy epithelia, and promotes epithelial regeneration to replace cells that are shed.

With injury, epithelial cell production of SLPI and proepithelin declines (FIG. 7D). Mast cells and immigrant leukocytes release proteinases that convert proepithelin to epithelins. Epithelins restrict premature epithelial repair (that is, wound closure before sterilization) while promoting the release of IL-8 or its functional equivalents in the mouse, which elicits the recruitment of more neutrophils to fight infection. Oxidants released by neutrophils inactivate SLPI (Carp and Janoff, 1980), allowing elastase to generate more Epithelins and perpetuating positive feedback. Eventually, exudation of plasma SLPI and the delayed immigration of macrophages (Rappolee and Werb, 1988; Witte and Barbul 1997) that release copious SLPI and proepithelin push the proepithelin-epithelin equilibrium back toward proepithelin. Proepithelin prevents neutrophils from discharging cytotoxic, SLPI-inactivating oxidants and proepithelin-digesting proteinases and drives epithelial cells to proliferate.

The foregoing interaction scheme is supported by the finding that exogenous proepithelin was as effective as exogenous SLPI in overcoming the defect in wound healing of SLPI-null mice. These findings suggest that one major consequence of SLPI deletion appears to be a relative deficiency of intact proepithelin. Of the molecules protected by SLPI, proepithelin appears to be one of the more important for timely healing of a wound. The findings described herein also raise the possibility that healing of refractory wounds might be promoted by the application of proepithelin and SLPI in combination.

The invention contemplates treatment of any type of wound. In some embodiments, the wound is a chronic wound. Chronic wounds or indolent, non-healing wounds may arise from different causes including infection, the presence of foreign bodies or toxic irritants, burns, prolonged cutaneously applied pressure and poor blood supply owing to impaired circulation. In a chronic wound the tissue homeostasis and the wound environment are compromised so that either healing fails to occur or healing begins but is subsequently halted. Factors contributing to the failure of healing in chronic wounds are tissue necrosis, dehydration, chronic wound edema, fibrotic induration, small blood vessel disease and, as provided herein, an imbalance in proepithelin and/or SPLI levels.

The invention also contemplates treatment or prevention of inflammatory responses, particularly neutrophil associated inflammatory conditions or diseases. Inflammatory conditions and diseases that may be prevented or treated with the proepithelin and/or SLPI compositions of the invention include conditions in which neutrophils are too active and those involving connective tissue degradation or cartilage degradation. Examples of problematic inflammatory diseases that may be treated or prevented include during arthritis, gout, rheumatoid arthritis and other inflammatory diseases. Other inflammatory diseases and conditions that may be treated by the compositions and methods of the invention include inflammatory bowel diseases such as Crohn's Disease, with or without a presently characterized and identifiable specific neutrophil disorder (such as Glycogen Storage Disease 1b or Chronic Granulomatous Diseases) pouchitis, fistulas, extraintestinal manifestations of Crohn's Disease, and Ulcerative Colitis. The Ulcerative Colitis can be of any extent, including proctitis, proctosigmoiditis, left-sided colitis, pancolitis and other types of inflammatory diseases.

Recombinant Production of Polypeptides

Polypeptides of the invention can be made recombinantly using convenient vectors, expression systems and host cells. The invention therefore provides expression cassettes, vectors and host cells useful for expressing a proepithelin polypeptide capable of inhibiting neutrophil activation and promoting wound healing.

Sequences for human proepithelin nucleic acids can be found in the NCBI database (see website at ncbi.nlm.nih-.gov), then placed in a selected host cell for recombinant expression of the encoded proepithelin protein. In some embodiments an expression cassette or expression vector is employed.

The expression cassettes of the invention include a promoter. Any promoter able to direct transcription of an encoded polypeptide or polypeptide may be used. Accordingly, many promoters may be included within the expression cassette of the invention. Some useful promoters include constitutive promoters, inducible promoters, regulated promoters, cell specific promoters, viral promoters, and synthetic promoters. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

For expression of a polypeptide in a bacterium, an expression cassette having a bacterial promoter will be used. A bacterial promoter is any DNA sequence capable of binding bacterial RNA polymerase and initiating the downstream (3") transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977), and maltose. Additional examples include promoter sequences derived from biosynthetic enzymes such as tryptophan (trp) (Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689,406) promoter systems also provide useful promoter sequences. A preferred promoter is the *Chlorella* virus promoter (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA*, 80:21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

An expression cassette having a baculovirus promoter can be used for expression of a polypeptide in an insect cell. A baculovirus promoter is any DNA sequence capable of binding a baculovirus RNA polymerase and initiating transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69:765 (1988)).

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PH05 gene, encoding acid phosphatase, also provides useful promoter sequences. (Myanohara et al., *Proc. Natl. Acad. Sci. USA*, 80:1 (1983)).

Synthetic promoters that do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of the ADH2, GAL4, GAL10, or PH05 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA*, 77:1078 (1980); Henikoff et al., *Nature*, 283:835 (1981); Hollenberg et al., *Curr. Topics Microbiol. Immunol.*, 96:119 (1981)); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; (Mercerau-Puigalon et al., *Gene*, 11: 163 (1980); Panthier et al., *Curr. Genet.*, 2:109 (1980)).

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science,* 236:1237 (1987)); Alberts et al., Molecular Biology of the Cell, 2nd ed., 1989). Enhancer elements derived from viruses are often times useful, because they usually have a broad host range. Examples include the SV40 early gene enhancer (Dijkema et al., *EMBO J.,* 4:761 (1985)) and the enhancer/promoters derived from the long terminal repeat (LTR) of the Rous Sarcoma Virus (Gorman et al., *Proc. Natl. Acad. Sci. USA,* 79:6777 (1982b)) and from human cytomegalovirus (Boshart et al., *Cell,* 41:521 (1985)). Additionally, some enhancers are regulatable and become active only in the presence of an inducer, such as a hormone or metal ion (Sassone-Corsi and Borelli, *Trends Genet.,* 2:215 (1986); Maniatis et al., *Science,* 236:1237 (1987)).

It is understood that many promoters and associated regulatory elements may be used within the expression cassette of the invention to transcribe an encoded polypeptide. The promoters described above are provided merely as examples and are not to be considered as a complete list of promoters that are included within the scope of the invention.

The expression cassette of the invention may contain a nucleic acid sequence for increasing the translation efficiency of an mRNA encoding a polypeptide of the invention. Such increased translation serves to increase production of the polypeptide. The presence of an efficient ribosome binding site is useful for gene expression in prokaryotes. In bacterial mRNA a conserved stretch of six nucleotides, the Shine-Dalgamo sequence, is usually found upstream of the initiating AUG codon. (Shine et al., *Nature,* 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology,* Green Publishing Associates and Wiley Interscience, NY. (1989); Beaucage and Caruthers, *Tetra. Letts.,* 22:1859 (1981); VanDevanter et al., *Nucleic Acids Res.,* 12:6159 (1984). Alternatively, translational start sequences can be obtained from numerous commercial vendors. (Operon Technologies; Life Technologies Inc, Gaithersburg, Md.). In some embodiments, the T7 translation initiation sequence is used. The T7 translation initiation sequence is derived from the highly expressed T7 Gene 10 cistron and can have a sequence that includes TCTAGAAATAATTTTGTTTAACTTTAAG AAGGAGATATA (SEQ ID NO:11). Other examples of translation initiation sequences include, but are not limited to, the maltose-binding protein (Mal E gene) start sequence (Guan et al., *Gene,* 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology, Chapter* 16, Green Publishing Associates and Wiley Interscience, NY).

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a polypeptide encoded by the expression cassette of the invention. Such nucleic acid sequences are within the scope of the invention.

The invention therefore provides an expression cassette or expression vector that includes a promoter operable in a selected host and a nucleic acid encoding a polypeptide having, for example, any one of SEQ ID NO:1, 2, 4, or 5. The expression cassette can have other elements, for example, termination signals, origins of replication, enhancers, and the like as described herein. The expression cassette can also be placed in a vector for easy replication and maintenance.

In one embodiment, the proepithelins of the invention can be expressed in yeast. While yeast are sometimes not used for expression of mammalian proteins, because glycosylation and disulfide bond formation might not be correctly reproduced in the yeast cytosol, this concern was not a problem in experiments provided herein. Yeast produced proepithelins were able to form a complex with SLPI (over 80% of the yeast proepithelin clones characterized were capable of SPLI binding).

Moreover, human proepithelin (aa 18-593) and mouse proepithelin (aa 18-589) were recombinantly produced in insect and mammalian cells with secretion being driven by the human proepithelin signal peptide (aa 1-17). Human and mouse nucleic acids encoding proepithelin with an N-terminal FLAG-6×His tag were inserted into a baculovirus vector. Recombinant baculovirus was obtained by recombination of BaculoGold DNA (Pharmingen) and pVL1393 vector-based constructs, amplified in Sf9 cells and used to infect Hi5 cells (Invitrogen) in suspension. Recombinant human PEPI was also expressed by HEK293 cells stably transfected with pTK-hygromycin$^R$ and pCMVI-FLAG-6×His-PEPI (aa 18-593). Transfectants were selected and maintained in 100 µg/ml hygromycin (Sigma, Mo.). Cells were grown to 90% confluence in Dulbecco s minimum Eagles medium (DMEM) with 10% fetal bovine serum, washed twice with phosphate buffered saline (PBS) and cultured in serum-free DMEM for 4 days.

For purification, conditioned media were concentrated by ammonium sulfate precipitation and purified by Ni-NTA (Qiagen) affinity chromatography. The imidazole-eluted proteins were dialyzed against 20 mM ammonium bicarbonate, lyophilized and reconstituted in sterile PBS.

Hence, the proepithelin and SLPI polypeptides of the invention can be made by recombinant procedures using a variety of host cells, including bacterial, yeast, insect and mammalian host cells.

Administration

Polypeptides of the invention can be used to heal wounds, to inhibit neutrophil activation, control inflammation and are beneficial for chronic wound healing. Individual polypeptides, polypeptide variants, polypeptide derivatives and mixtures thereof (e.g. those with different sequences) can be combined in a formulation to promote wound healing, control inflammation and to prevent neutrophil activation. Optimal healing and neutrophil inhibition may require some epithelin or neutrophil activity. Hence, the compositions and formulations of the present invention do not necessarily promote maximal inhibition of neutrophil activation. Instead, the activity of the polypeptide formulation is varied as needed to optimize healing, discourage neutrophil activation and promote healthy skin development. Lesser or greater levels of inhibition can be achieved by varying the type, content and amount of polypeptides so that healing and healthy skin development is promoted while inflammation is controlled.

To promote healthy skin development and/or treat wounds, polypeptides of the invention are introduced onto the skin or into wounds in any manner chosen by one of skill in the art. The polypeptides can be administered by a variety of routes to control inflammation or inhibit neutrophil activation. For example, polypeptides can be formulated into a therapeutic composition containing a therapeutically effective amount of one or more polypeptides and a pharmaceutical carrier.

In some embodiments, such a composition can be introduced onto skin or into the wound as a cream, spray, foam, gel or in the form of any other formulation. In another embodiment, polypeptides of the invention can be formulated into a skin covering or dressing containing a therapeutically effective amount of one or more polypeptides impregnated into, covalently attached or otherwise associated with a covering or dressing material. In one embodiment, the skin covering or dressing permits release of the polypeptide. Release of the polypeptide can be in an uncontrolled or a controlled manner. Hence, the skin coverings or wound dressings of the invention can provide slow or timed release of the polypeptide into a wound. Skin coverings and dressing materials can be any material used in the art including bandage, gauze, sterile wrapping, hydrogel, hydrocolloid and similar materials.

In other embodiments, a composition of the invention can be formulated for oral, topical, subcutaneous, parenteral, intravenous, or pulmonary delivery. Such compositions may be used for control of inflammation in a variety of situations.

Therapeutic compositions of the invention can comprise proepithelin or a pharmaceutically-active subunit thereof, optionally in combination with SLPI or an active subunit thereof, one or both in combination with a pharmaceutically acceptable carrier. In some cases SLPI or a subunit thereof can be formulated separately and used as the sole therapeutic agent.

Proepithelin and/or SLPI therapeutic compositions can also contain liquids, such as water, saline, glycerol, wetting agents, emulsifying agents, or pH buffering agents. Liposomes, such as those described in U.S. Pat. No. 5,422,120, WO 95/13796, WO 91/14445, or EP 524,968 B1 can also be used as a carrier for such therapeutic compositions.

A therapeutically effective amount of a polypeptide of the invention is an amount of polypeptide that promotes healthy skin development and/or wound healing. In another embodiment, a therapeutically effective amount of a polypeptide of the invention is an amount of polypeptide that controls inflammation and/or inhibits neutrophil activation.

For example, when present in a therapeutic or pharmaceutical composition, the amount of polypeptides of the invention can be in the range of about 0.001% to about 85% by weight of the composition. The polypeptides can form about 0.5% to about 30% by weight of the composition. Alternately, the polypeptides form about 1.0% to about 10% by weight of the composition.

The therapeutically effective amount of polypeptide necessarily varies with the route of administration. For example, a therapeutic amount between 30 to 112,000 µg per kg of body weight can be effective for intravenous administration. However, the amount of the polypeptide required will vary not only with the route of administration, but also the nature of the condition being treated and the age and condition of the patient and will be ultimately at the discretion of the attendant physician or clinician.

The dosage and method of administration can vary depending upon the location of the skin or tissue to be treated and/or upon severity of the wound or inflammation. Useful dosages of the polypeptides and polypeptide conjugates can be determined by correlating their in vitro activity, and in vivo activity in animal models, for example, those described herein. Doses effective in humans can be extrapolated from doses effective in mice as taught by U.S. Pat. No. 5,294,430.

For example, the polypeptides can conveniently be administered in unit dosage form; for example, containing about 0.001 µg to about 10 mg, conveniently about 0.01 µg to about 5 mg, more conveniently, about 0.10 µg to about 1 mg, and even more conveniently about 1.0 µg to 500 µg of polypeptide per unit dosage form. The desired dose may be presented in a single dose, as divided doses, or as a continuous infusion. The desired dose can also be administered at appropriate intervals, for example, as two, three, four or more sub-doses per day. One of skill in the art can readily prepare and administer an effective formulation from available information using the teachings provided herein.

The polypeptides of the invention can be formulated as pharmaceutical compositions and administered to a mammalian host, such as a human patient in a variety of dosage forms adapted to the chosen route of administration, i.e., orally or parenterally, by intravenous, intramuscular, topical or subcutaneous routes.

Thus, the polypeptides may be systemically administered, for example, intravenously or intraperitoneally by infusion or injection. Solutions of the polypeptide can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion or topical application can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, one of skill in the art may choose to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptides in the required amount in the appropriate solvent with various of the other ingredients enumerated herein, as required, followed by filter sterilization. In the case of sterile powders for the preparation of sterile injectable solutions, methods of preparation include vacuum drying and the freeze-drying techniques, which yield a powder of the active ingredient plus any additional desired ingredient present in the previously sterile-filtered solutions.

In some instances, the polypeptides can also be administered orally, in combination with a pharmaceutically acceptable vehicle such as an inert diluent or an edible carrier. They may be enclosed in hard or soft shell gelatin capsules, may be compressed into tablets, or may be incorporated directly with the food of the patient's diet. For oral therapeutic administration, the polypeptide may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptide may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohouglycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In general, the polypeptides of the invention are administered topically for wound treatment and for promoting healthy skin development. The polypeptides of the invention may also be administered topically for treatment of inflammation. The active polypeptides may be administered topically by any means either directly or indirectly to the selected tissue as sprays, foams, powders, creams, jellies, pastes, suppositories or solutions. The term paste used in this document should be taken to include creams and other viscous spreadable compositions such as are often applied directly to the skin or spread onto a bandage or dressing. Polypeptides of the invention can be covalently attached, stably adsorbed or otherwise applied to a skin covering or wound dressing material. To facilitate healing after surgery, the active polypeptides of the invention can be applied directly to target tissues or to prosthetic devices or implantable sustained released devices. The compositions can be administered by aerosol, as a foam or as a mist, with or without other agents, directly onto the skin or wound.

The polypeptides can be administered in a formulation that can include an emulsion of the polypeptide in a wax, oil, an emulsifier, water, and/or a substantially water-insoluble material that forms a gel in the presence of water. The formulation provides the desirable properties of an emulsion, in that it is spreadable and has the creamy consistency of an emulsion, yet that does not break down when subjected to normal sterilization procedures, e.g. steam sterilization, because the gel stabilizes the emulsion. It also exhibits better water retention properties than a conventional gel because water is held both in the emulsion and in the gel.

The formulation can also contain a humectant to reduce the partial vapor pressure of the water in the cream or lotion to reduce the rate at which the cream or lotion dries out. Suitable humectants are miscible with water to a large extent and are generally suitable for application to the skin. Polyols are especially suitable for the purpose and suitable polyols may include monopropylene glycol or glycerin (glycerol). The polyol may be present in proportions of 20-50% (by weight) of the total formulation; alternatively the range is 30-40%. This relatively high proportion of polyol also ensures that if the paste should dry out to any degree, the resulting paste remains soft and flexible because the glycerin may act as a plasticizer for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

The formulation can include other ingredients. Ingredients that may be used include: zinc oxide, ichthammol, calamine, silver suphadiazine, chlorhexidine acetate, coal tar, chlorhexidine gluconate, salicylic acid, metronidazole or other antibacterial agents, or a combination thereof. Other ingredients may also be found suitable for incorporation into the cream.

These ingredients can be included in beneficial amounts, for example, up to about 15 wt %, of zinc oxide may be added; typically 6-10% of zinc oxide is used, possibly in combination with another ingredient such as ichthammol (0-3 wt %) and/or calamine (0-15% wt). Ichthammol or calamine may also be used alone. Chlorhexidine acetate can be used at a concentration of up to 1% by weight; 0.5 wt % is typical.

An example of a wax for the emulsion is glyceryl monostearate, or a combination of glyceryl monostearate and PEG100 stearate that is available commercially as CITHROL GMS/AS/NA from Croda Universal Ltd. This combination provides both a wax and an emulsifier (PEG 100 stearate) that is especially compatible with the wax, for forming an emulsion in water. A second emulsifier can be included in the formulation to increase the stability of the emulsion, for example, a PEG20 stearate, such as CITHROL 1OMS that is supplied by Croda Universal Ltd. The total concentration of emulsifier in the cream should normally be in the range of from 3-15%. Where two emulsifiers are used, one may be present in a greater concentration than the other.

The water-insoluble material forms a gel with the water of the formulation. The material is therefore hydrophilic but does not dissolve in water to any great extent. The material can be a polymeric material, for example, a water-absorbing non water-soluble polymer. However, non-polymeric materials that form gels with water and that are stable at elevated temperatures could also be used, e.g. clays such as kaolin or bentonite. Some polymers used in the invention are super-absorbent polymers such as those disclosed in WO-92/16245 and that comprise hydrophilic cellulose derivatives that have been partially cross-linked to form a three dimensional structure. Suitable cross-linked cellulose derivatives include those of the hydroxy lower alkyl celluloses, wherein the alkyl group contains from 1 to 6 carbon atoms, e.g. hydroxyethyl cellulose or hydroxypropylcellulose, or the carboxy-celluloses e.g. carboxymethyl hydroxyethyl cellulose or carboxymethylcellulose. An example of a polymer that may be used in the invention is a partially cross-linked sodium carboxymethyl-cellulose polymer supplied as AKUCELL X18 lby Akzo Chemicals B.V. This polymer is a super absorbent polymer in that it may absorb at least ten times its own weight of water. The cross-linked structure of the polymer prevents it from dissolving in water but water is easily absorbed into and held within the three-dimensional structure of the polymer to form a gel. Water is lost less rapidly from such a gel than from a solution and this is advantageous in slowing or preventing the drying out of the cream formulation. The polymer content of the formulation is normally less than 10%, for example, the polymer content can range from about 0.5 to about 5.0% by weight, or from about 1.0% to about 2% by weight.

The formulation may be sterilized and components of the formulation should be selected, by varying the polymer content, to provide the desired flow properties of the finished product. That is, if the product to be sterilized, then the formulation should be chosen to give a product of relatively high viscosity/elasticity before sterilization. If certain components of the formulation are not to be sterilized, the formulation can be sterilized before addition of those components, or each component can be sterilized separately. The formulation can then be made by mixing each sterilized ingredients under sterile conditions. When components are separately sterilized and then mixed together, the polymer content can be adjusted to give a product having the desired flow properties of the finished product. The emulsion content determines the handling properties and feel of the formulation, higher emulsion content leading to increased spreadability and creaminess.

The formulation may be packaged into tubes, tubs or other suitable forms of containers for storage or it may be spread onto a substrate and then subsequently packaged. Suitable substrates include dressings, including film dressings, and bandages.

Administration can be prior to wounding, as to prior to a surgical incision, or after the wound has formed, as in treatment of a trauma victim. Various methods can be used to administer a therapeutic composition directly to a specific site in the body. For example, therapeutic compositions can be injected several times into or adjacent to a site of wounding, such as a surgical incision or a traumatic injury, or infused intravenously or intra arterially, so as to reach the target site.

The following examples are intended to illustrate but not limit the invention.

EXAMPLE 1

Experimental Procedures

This Example provides materials and procedures for experiments performed on proepithelin.

Yeast Two-Hybrid Screening and cDNA Cloning

A C3H/HeN mouse bone marrow derived macrophage cell line, HeNC$_2$ (Jin et al., 1997), was used for construction of a leukocyte cDNA library in the phagemid vector, pAD-GAL4 (Stratagene). The bait construct, pBD-GAL4-SLPI, contains a truncated mouse SLPI ORF (aa26-131). Screening followed the Hybri-ZAP™ kit protocol (Stratagene). Briefly, YRG-2 yeast harboring pBD-GAU-SLPI were transformed with the pAD-GAL4-HeNC$_2$ cDNA library and grown on plates lacking histidine. Clones recovered from His- plates were analyzed for β-galactosidase activity. Plasmid DNAs rescued from individual His$^+$/Pgal$^+$ clones were subjected to restriction enzyme digestion analysis and DNA sequencing. The partial PEPI ORF derived from a His$^+$/β-gal$^+$ clone was labeled with $^{32}$P-dCTP to screen the HeNC$_2$ cDNA phage library and to clone full-length mouse PEPI cDNA. To clone human PEPI and SLPI, primers flanking the ORFs were used for RT-PCR with total RNA of A549 cells as template.

Proepithelin and Epithelin Sequences

Sequences for various regions within human proepithelin are provided below. The proepithelin sequences shown correspond to the human proepithelin sequence provided in the NCBI database as accession number P28799). For example, the signal peptide for this human proepithelin (amino acids 1-16) is as follows:

MWTLVSWVALTAGLVA (SEQ ID NO:12).

The first linker region within proepithelin links the signal peptide to a half epithelin. This para epithelin with the linker has an elastase cleavage site (^) and has the following sequence (proepithelin amino acids 17-57):

GTRCPDGQFCPVACCLDPGGASYSCCR-PLLDKWPT^TLSRHL (SEQ ID NO:13).

Epithelin G resides within proepithelin amino acids 58-113 and has the following sequence:

GGPCQVDAHCSAGHSCIFTVSGTSSC-CPFPEAVACGDGHHCCPRG FHCSADGRSCF (SEQ ID NO:14).

The second linker region within proepithelin (amino acids 114-122) links the para epithelin peptide to epithelin F. This linker region has the following sequence:

QRSGNNSVG (SEQ ID NO:15).

Epithelin F resides within proepithelin amino acids 123-179 and has the following sequence:

AIQCPDSQFECPDFSTCCVMVDGSWGC-CPMPQASCCEDRVHCC PHGAFCDLVHTRCI (SEQ ID NO:16).

The third linker region within proepithelin (amino acids 180-205) links epithelin F to epithelin B. This linker region has the following sequence:

TPTGTHPLAKKLPAQRTNRAVALSSS (SEQ ID NO:17).

Epithelin B resides within proepithelin amino acids 206-261 and has the following sequence:

VMCPDARSRCPDGSTCCELPSGKYGCCP-MPNATCCSDHLHCCPQDTVCDLIQS KCL (SEQ ID NO:18).

The fourth linker region within proepithelin (amino acids 262-280) links epithelin B to epithelin A. This linker region has the following sequence:

SKENATTDLLTKLPAHTVG (SEQ ID NO:19).

Epithelin A resides within proepithelin amino acids 281-336 and has the following sequence:

DVKCDMEVSCPDGYTCCRLQSGAWGC-CPFTQAVCCEDHIHCCPAGFTCDTQK GTCE (SEQ ID NO:20).

The fifth linker region within proepithelin (amino acids 337-363) links epithelin A to epithelin C. This linker region has two elastase sites (^) and has the following sequence:

QGPHQVPWMEKAPAAHLSLPDPQA^LKRD (SEQ ID NO:21).

Epithelin C resides within proepithelin amino acids 364-417 and has the following sequence:

VPCDNVSSCPSSDTCCQLTSGEWGCCPI-PEAVCCSDHQHCCPQRYTC VAEGQCQ (SEQ ID NO:22).

The sixth linker region within proepithelin (amino acids 418-441) links epithelin C to epithelin D. This linker region has the following sequence:

RGSEIVAGLEKMPARRASLSHPRD (SEQ ID NO:23).

Epithelin D resides within proepithelin amino acids 442-496 and has the following sequence:

IGCDQHTSCPVGGTCCPSLGGSWACCQL-PHAVCCEDRQHCCPAGYT CNVKARSCE-496 (SEQ ID NO:24).

The fifth linker region within proepithelin (amino acids 337-363) links epithelin D to epithelin E. This linker region has one elastase site (^) and has the following sequence:

KEVVSAQPATFLARSPHVGV^AK (SEQ ID NO:25).

Epithelin E resides within proepithelin amino acids 518-573 and has the following sequence:

DVECGEGHFCHDNQTCCRDNRQGWAC-CPYRQGVCCADRRHCCPAGFRCAAR GTKCL (SEQ ID NO:26).

The final (C-terminal) sequence in proepithelin includes amino acids 574-593 and is as follows:

RREAPRWDAPLRDPALRQLL (SEQ ID NO:27).

Protein Expression, Purification and Analysis

Human PEPI (aa 18-593), human EPIs A (aa 281-337) and B (aa 206-261) and mouse PEPI (aa 18-589) each with an N-terminal FLAG-6xHis tag, were produced with secretion being driven by the human PEPI signal peptide (aa 1-17). Recombinant baculovirus was obtained by recombination of BaculoGold DNA (Pharmingen) and pVL1393 vector-based constructs, amplified in Sf9 cells and used to infect HiS cells (Invitrogen) in suspension. Recombinant human PEPI was also expressed by HEK293 cells stably transfected with pTK-hygromycin$^R$ and pCMVI-FLAG-6xHis-PEPI (aa 18-593). Transfectants were selected and maintained in 100 µg/ml hygromycin (Sigma, Mo.). Cells were grown to 90% confluence in Dulbecco s minimum Eagle s medium (DMEM) with 10% fetal bovine serum, washed twice with phosphate buffered saline (PBS) and cultured in serum-free DMEM for 4 days. Conditioned media were concentrated by ammonium sulfate precipitation and purified by Ni-NTA (Qiagen) affinity chromatography. The imidazole-eluted proteins were dialyzed against 20 mM ammonium bicarbonate, lyophilized and reconstituted in sterile PBS. Recombinant human and mouse SLPI were from Amgen (Thousand Oaks, Calif.). Pure, recombinant human or mouse protein (PEPI or SLPI) was injected into rabbits to raise antisera.

PEPI and SLPI were transiently expressed in HEK293 or COS-1 cells. FLAG-tagged PEPI (aa 18-593) was expressed from pCMVI-FLAG and SLPI constructs from pcDNA3.1 (Invitrogen). SLPI constructs included mouse full length (aa 1-131), mouse N-terminal domain (aa 1-80), mouse C-terminal domain (aa 1-25/81-131), and human full-length (aa 1-131). Three days following co-transfection via SuperFect reagent (Qiagen), conditioned media were immunoprecipitated with FLAG M2 antibody (Sigma), separated by reducing SDS-PAGE and western blotted with anti-SLPI antibody (Jin et al., 1997). For in vitro immunoprecipitation assays, recombinant human PEPI or EPI (FLAG-tagged) and SLPI (5 pmol each) were incubated in 10 mM Tris-HCl (pH 7.5), 150 mM NaCl at 37° C. for 30 min before immunoprecipitation with anti-FLAG M2 antibody and western blotting with anti-SLPI antibody or the reverse.

BAL fluids were collected from healthy adult subjects according to an institutional review board-approved protocol following informed consent. The fluids (45 ml each) were concentrated to 0.5 ml in a Centriprep (Millipore) with 10 kDa cut-off before immunoprecipitation with antiserum against human PEPI and western blotting with antisera against human SLPI or human PEPI.

Recombinant mouse PEPI purified via FLAG M2 antibody affinity column was subjected to digestion by human neutrophil elastase (Sigma) in 100 mM Tris-HCl (pH 8.3) and 960 mM NaCl (Kramps et al., 1983); human neutrophil cathepsin G (Calbiochem-Novabiochem) in 100 mM Tris-HCl (pH 7.5), 20 mM $MgCl_2$, 1% DMSO (Rehault et al., 1999); bovine pancreatic a-chymotrypsin (Sigma) in 100 mM Tris-HCl (pH 7.5) and 10 mM $CaCl_2$ (DelMar et al., 1979); or bovine pancreatic trypsin (Sigma) in 100 mM Tris-HCl (pH 7.8) and 20 mM $CaCl_2$ (Somorin et al., 1979) at 37° C.

For determination of the cleavage sites, recombinant human PEPI (35 µg) was incubated with elastase at 37° C. for 18 h. The products were separated by reducing SDS-PAGE and transferred to a PVDF membrane (Bio-Rad) and stained with Coomassie blue. Bands were excised for Edman degradation, as described (Tempst et al., 1994).

Cell-Based Assays

Human epithelial cell lines SW-13 and A549 from ATCC were plated at $0.5 \times 10^5$ cells/well in 96-well plates and treated with protein samples for 48 h. IL-8 was measured in the conditioned media by ELISA (R&D Systems). When indicated, PEPI (100 µM) and elastase (3 u/ml) or either agent alone were pre-incubated for 18 hr at 37° C. in 960 mM NaCl (used to prevent elastase from adsorption to vessel surfaces) and diluted 10-fold in medium before addition to the cells. Alternatively, the cells were plated at $0.4 \times 10^5$ cells/well in 24-well plates and 1 day later switched to serum-free medium containing recombinant proteins for 3 days before measuring cell numbers with the CyQUANT Cell Proliferation Kit (Molecular Probes), or by hemocytometer count of trypan blue-excluding cells.

Neutrophils were isolated from heparinized blood of normal donors with a modified Ficoll-Hypaque gradient (Cardinal Associates)(Fuortes et al., 1993). Erythrocytes were lysed by hypotonic shock and neutrophils resuspended in ice-cold Krebs-Ringer phosphate buffer with glucose (KRPG) for measurement of $H_2O_2$ production by the scolopetin assay (Fuortes et al., 1993) in FBS-precoated Primaria™ 96-well plates (Becton-Dickinson, N.J.) using $1.5 \times 10^4$ neutrophils per well. Cells were treated with protein samples and 100 ng/ml of either phorbol myristate acetate (Sigma) or TNF (Genentech, Calif.) and incubated at 37° C. $H_2O_2$ production was monitored every 30 min in a fluorescence microplate reader (SpectraMax Gemini, Molecular Devices).

To measure proteinase release, $25 \times 10^6$ neutrophils in 4 ml of KRPG were seeded in FBS-precoated 10 cm Primaria™ culture dishes and treated with protein samples and/or 100 ng/ml TNF. Aliquots of the medium were taken at designated times and floating cells removed by centrifigation. 100 µl supernatant was transferred into a 96 well plate and incubated with 10 µg/ml BODIPY FL casein substrate (Molecular Probes) for 2 h at room temperature. Proteinase activity was monitored in a fluorescence microplate reader (Molecular Devices) compared to human neutrophil elastase (Sigma) as standard. To distinguish degranulation from cell lysis, lactate dehydrogenase activity in the conditioned media was assayed using a kit (Roche Molecular Biochemicals).

For conditioned medium, $10^7$ neutrophils/ml in KRPG were stimulated with 100 ng/ml of PMA at 37° C. for 30 min and the cells were removed by centrifugation diisopropyl fluorophosphate was added (2 µg/ml). PEPI alone or a mixture of PEPI and SLPI was incubated with 40 µl conditioned medium at 37° C. for 30 min before SDS-AGE and western blot with anti-FLAG antibody.

For morphologic assessment, $0.5 \times 10^6$ neutrophils in KRPG were plated onto FBS-precoated glass cover slips in 12-well plates. Cells were incubated with protein samples and 100 ng/ml of PMA or TNF for about 40 min, by which time cells treated with TNF alone were fully spread. Cells were fixed as described (Fuortes et al., 1993) and photographed with a Sony DKC-5000 digital camera via an Olympus BX60 microscope.

For determination of Pyk2 phosphorylation, $2.5 \times 10^7$ neutrophils in KRPG were pretreated with 1 µM of PEPI or ovalbumin followed by stimulation with 100 ng/ml TNF. Cell lysates were fractionated on SDS-AGE and western blotted with antibodies (Biosource Camarillo, Calif.) as described (Fuortes et al., 1999).

Wound Healing

SLPI null mice (C57BL6×129) were generated as described by Ashcroft et al. (2000). The SPLI null mice and genetically matched wild type mice of both genders, aged 4 to 8 wks, were anaesthetized with methoxyfluorane. The dorsum was shaved and sterilized with alcohol. 50 ml of PBS containing no protein or 1 µg recombinant rat SLPI or 1 µg recombinant mouse PEPI was injected subcutaneously. Treatments were rotated to exclude site bias. Four equidistant 1-cm full thickness incisional wounds were made through the skin and panniculus carnosus. Wounds were biopsied at day 3 and bisected perpendicular to the long axis for RNA extraction and histology. The haematoxylin and eosin stained cross section was quantified for the width of the epithelial gap (Adobe Photoshop 5.5) and for the wound area (MetaMorph4.6, Universal Imaging Co.), defined by the inflammatory region under the scar, above the muscle and fat layers and flanked by the wound edges. Northern blots were probed with mouse PEPI and SLPI ORF cDNA fragments.

EXAMPLE 2

SLPI Binds PEPI

SLPI inhibits the inflammatory responses of macrophages and monocytes to microbial products (Jin et al., 1998; Jin et al., 1997; Wahl et al., 1997; Song et al., 1999). To define the mechanism for such inhibition, a mononuclear phagocyte cDNA library was tested to ascertain whether these cells expressed molecular target(s) of SLPI.

A yeast two-hybrid approach was used to identify SLPI-binding proteins. Mouse SLPI is a 131-amino acid protein with an N-terminal 25-residue signal peptide (FIG. 1A). The mature sequence (aa 26-131) was used as the bait in fusion with the DNA-binding domain of the yeast transcriptional activator, GAL4. A cDNA library was constructed from a mouse bone marrow macrophage cell line (HeNC$_2$) and expressed in fusion with the activation domain of GAL4 (GAL4-AD). Four million yeast co-transformants were analyzed for histidine auxotrophy and β-galactosidase activity. Twenty-seven clones showed strong phenotypes in both assays. BamH and EcoR V digests (FIG. 1B) assigned these 27 clones to 3 sequences. Sequencing confirmed that 21 of the clones encoded the same partial cDNA from mouse PEPI, comprising 1180 bp of the ORF and 338 bp of the 3' UTR (FIG. 1A, underlined). An additional clone consisted of a shorter piece of PEPI cDNA (clone 18 in FIG. 1B). The PEPI sequences were in frame with GAU-AD. The PEPI-SLPI interaction was confirmed in yeast and its specificity demonstrated (FIG. 1C).

PEPI contains 90 Cys residues that must form 45 correct disulfides. Thus, it is not surprising that we were unable to produce soluble, monomeric, intact PEPI and EPIs in *E. coli*. However, a baculovirus-insect cell expression system yielded EPI A in trace amounts and EPI B in somewhat larger amounts (FIG. 2A). Mouse and human proepithelins produced by insect cells were recovered mostly as degradation products (not shown). Reciprocally, mammalian COS-1 (not shown) and HEK293 cells (FIG. 2A) produced stable PEPI but not EPIs (not shown).

Figure 2B:
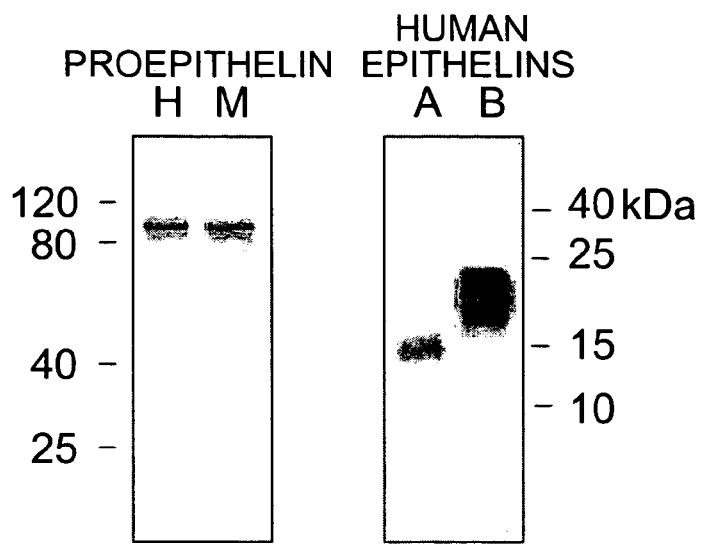
Figure 2B:
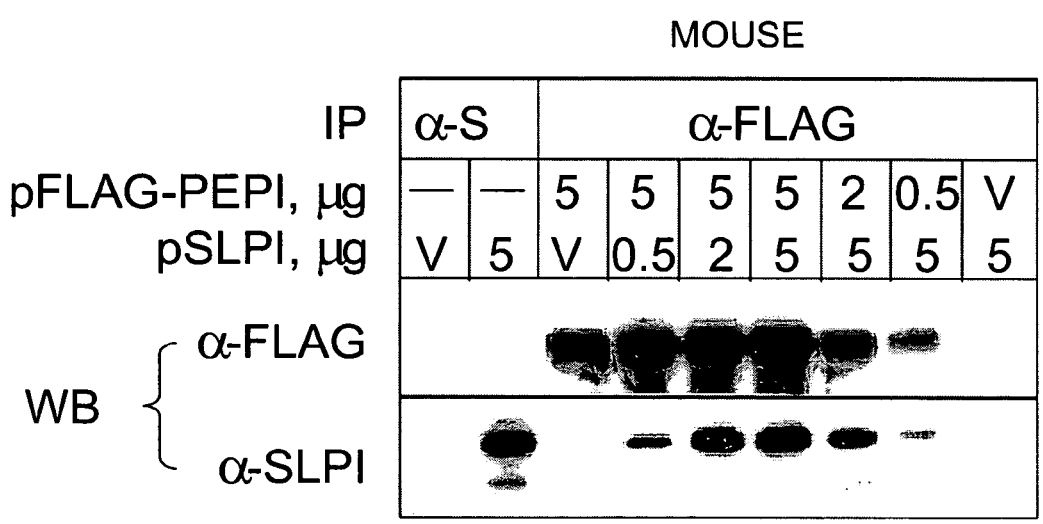
Figure 2C:
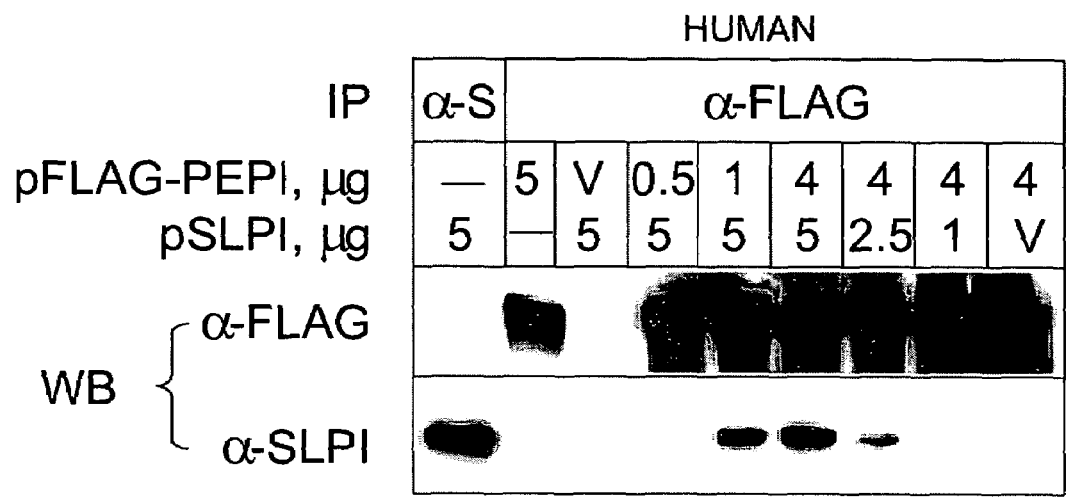

The SLPI-PEPI interaction was further characterized in vivo using transfected mammalian cells, and in vitro using recombinant proteins purified from human and insect cells for PEPI and EPIs, respectively. Mouse SLPI and FLAG-tagged mouse PEPI were cotransfected into COS-1 cells (FIG. 2B). Human SLPI and FLAG-tagged human PEPI were separately co-transfected into HEK293 cells (FIG. 2C). The conditioned media were immunoprecipitated with anti-FLAG antibodies to bring down PEPI, and then western blotted with anti-SLPI antibody. SLPI co-immunoprecipitated with PEPI for both the mouse and human protein pairs. The two proteins were recovered together in amounts proportionate to the quantity of cDNAs used for transfection.

Figure 2D:
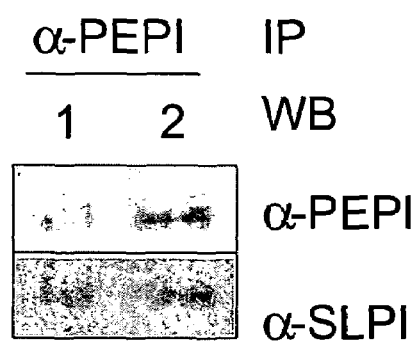

To test if a SLPI-PEPI complex exists in vivo normal human bronchoalveolar lavage (BAL) fluid samples were examined because both SLPI and PEPI are strongly expressed in airway epithelium (Abe et al., 1991; Daniel et al., 2000). PEPI was immunoprecipitated from the BAL fluids collected from two individuals, and SLPI was detected in the PEPI immunoprecipitates (FIG. 2D). Thus, the SLPI-PEPI complex is physiologic.

Next, experiments were performed to ascertain which part of PEPI binds to SLPI (for the order of EPIs in PEPI, see FIG. 1A). EPIs G and F were absent in the partial PEPI sequences isolated as SLPI-binding proteins in yeast (FIG. 1A) and thus were dispensable for the interaction. A series of mouse PEPI terminal deletion mutants were made and co-transfected these mutants with SLPI into COS-1 cells. Truncation mutants containing EPIs G, F, B, A and C co-immunoprecipitated with SLPI (not shown), indicating that EPIs D and E are not required for binding of PEPI to SLPI. The expression level of further truncation mutants dropped dramatically as the deletion proceeded making it difficult to interpret co-immunoprecipitation results with the shorter forms. When FLAG-tagged recombinant human EPI A or EPI B was incubated with recombinant human SLPI at an equimolar ratio (FIG. 2E) or at a molar ratio of A (or B):SLPI::1:5 (not shown), SLPI was not detected in EPI immunoprecipitates or vice versa. Yet, in a similar assay, holo-PEPI and SLPI each reciprocally co-immunoprecipitated with the other (FIG. 2E).

These results indicate, first, that PEPI and SLPI bound each other without the mediation of additional proteins, and second, that EPIs, B, D, E, F, and G were each not necessary or not sufficient for stable interaction with SLPI. It was not excluded that SLPI might bind uniquely to EPI C. However, this seems unlikely, because EPI C is highly homologous (87% among EPIs) to the 6 EPIs to which SLPI did not bind. Instead, SLPI appears to bind to inter-EPI linker region(s) of PEPI, or to a site only present in PEPI's tertiary structure.

Mutation analysis and the crystal structure of human SLPI with a target proteinase (Grutter et al., 1988) localized SLPI's anti-proteinase site to the C-terminal domain, where Leu72-Met73 are displayed in a loop that interacts with the catalytic triad of serine proteinases (Eisenberg et al., 1990). Likewise, the inventors have found that SLPI's C-terminal domain selectively interacts with PEPI (not shown). The interaction between SLPI and proepithelin may be based in part on electrostatics. Human SLPI bears twelve net positive charges and proepithelin five net negative charges. While the N-terminal domain carries half of SLPI's positive charges, they are scattered. In contrast those in the C-terminal domain of human SLPI (R58, R59, K60, K63, K87, R88, K91 and K106) are clustered in a patch on the surface opposite the proteinase binding loop (Grutter et al., 1988). The basic patch is conserved in mouse SLPI. This suggests that SLPI's C-terminal domain may bind elastase on one face and proepithelin on the opposite face.

EXAMPLE 3

Elastase is a PEPI Convertase

Because SLPI binds PEPI but not EPIs, PEPI converts to EPIs, and SLPI inhibits serine proteinases, the postulate that SLPI might block conversion of PEPI to EPIs was examined. Such conversion of PEPI to EPIs may occur by either or both of two mechanisms: (i) SLPI binding to and blocking a serine proteinase component of a PEPI convertase, and (ii) SLPI binding to and blocking cleavage sites in PEPI. Tests were run to ascertain whether any of 4 well-known SLPI-targeted serine proteinases could cleave PEPI: elastase and cathepsin G from human neutrophils, and trypsin and chymotrypsin from bovine pancreas.

Figure 3A:

Only elastase and chymotrypsin hydrolyzed recombinant human PEPI (FIG. 3A). Mouse SLPI is an effective inhibitor of elastase and chymotrypsin, but a relatively poor inhibitor of cathepsin G and trypsin (Zitnik et al., 1997). Similarly, human SLPI has Ki values for elastase, chymotrypsin cathepsin G and trypsin of 0.3, 2.4, 10 and 44 TIM, respectively (Wright et al., 1999; Zitnik et al., 1997). These results suggested that the proteinases that SLPI readily inhibits are the ones most capable of hydrolyzing PEPI.

Figure 3B:
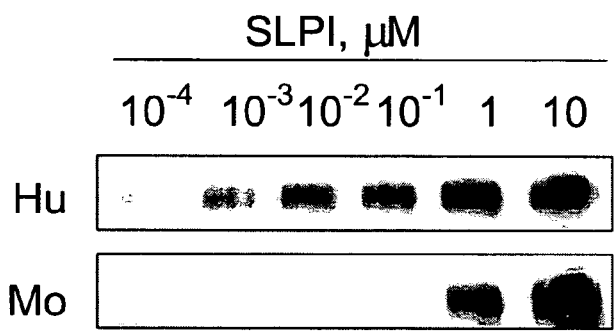
Figure 3C:
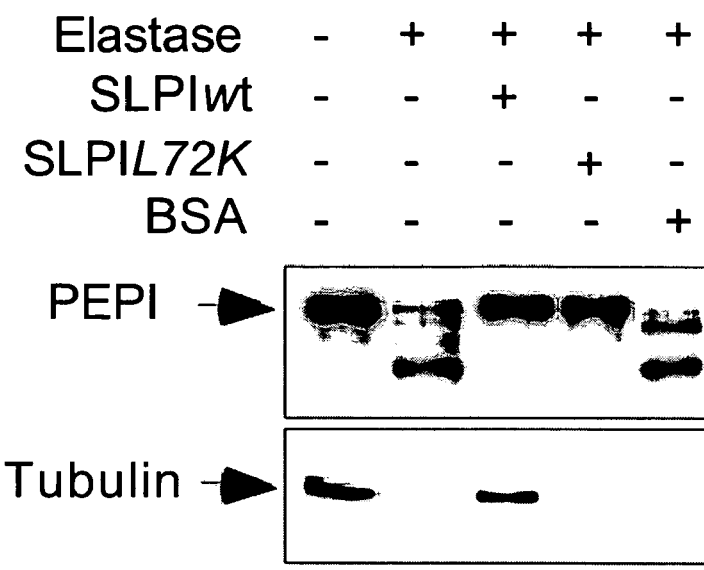

As expected from these observations, human and mouse SLPI did block the cleavage of human PEPI by elastase, human SLPI being the more potent (FIG. 3B). To see whether binding between SLPI and PEPI could also contribute to the protection of PEPI from elastase, a SLPI active-site mutant (L72K) was used that is no longer inhibitory to elastase (Eisenberg et al., 1990), but is still capable of binding SLPI (not shown). SLPIL72K protected PEPI from elastase digestion (FIG. 3C). Neither a control protein (BSA), nor a control substrate (tubulin) protected PEPI from elastase digestion. Thus, SLPI can protect PEPI from digestion by two distinct mechanisms: binding to a serine proteinase and binding to PEPI.

Figure 3D:
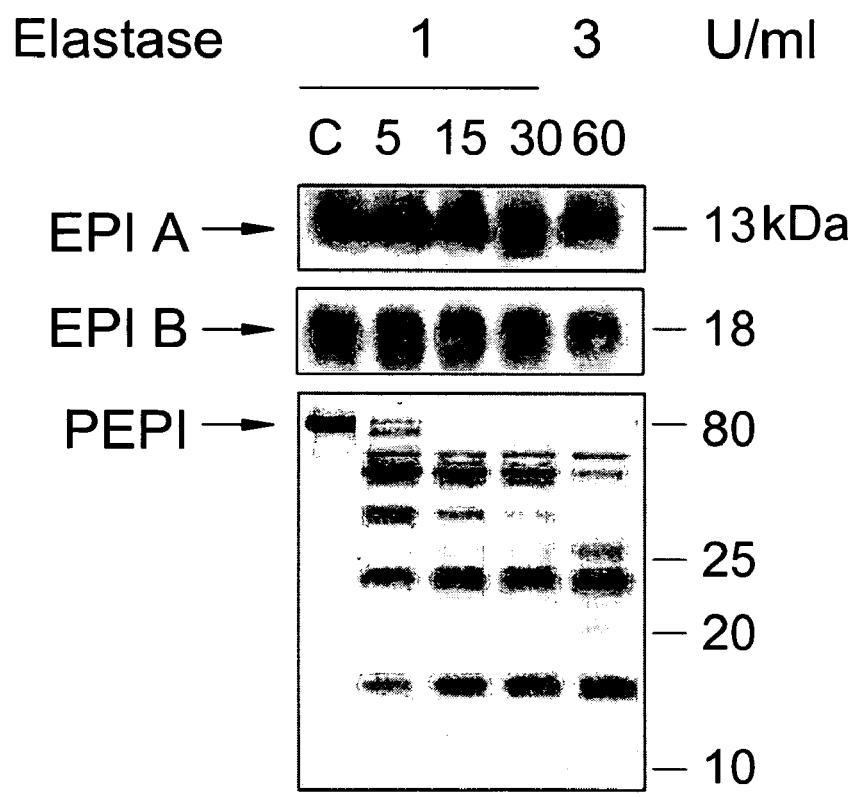

Neutrophil elastase is a candidate to contribute to PEPI convertase activity, because elastase is released in large quantities during infection and inflammation at PEPI-producing sites. At these same sites, elastase is also likely to encounter its physiologic regulator, SLPI. If elastase can participate in the processing of PEPI to EPIs, it should not cleave PEPI within EPI domains. Indeed, EPI A and B were resistant to elastase (FIG. 3D). In contrast, PEPI itself was cleaved by elastase in a concentration- and time-dependent manner, yielding discrete fragments.

To determine elastase cleavage sites, PEPI fragments from an extensive elastase digestion (3 u/ml, 18 h) were subjected to N-terminal sequencing. Fifteen identifiable N-terminal sequences of 8 independent gel slices from the region of apparent molecular mass 13 to 22 kDa (where recombinant EPIs migrate) all were from linker regions of PEPI (FIG. 4E). No cleavage site was found within any epithelin domain. Virtually complete conversion of PEPI to epithelin-sized fragments was also observed with protein chip mass spectrometry (Ciphergen system, not shown). Therefore, elastase cuts PEPI in the inter-BPI regions. While elastase thus can act as at least part of a PEPI convertase, additional proteolytic events would be required to produce precisely the same boundaries identified in EPIs as they have been purified from tissues.

EXAMPLE 4

Contrasting Effects of PEPI and EPIs on Epithelial Cells

PEPI is a growth factor for cells of epithelial origin and various tumors (Zanocco-Marani et al., 1999; Zhou et al., 1993). In contrast, EPI A and B inhibited growth of epithelial cells.

Figure 4B:
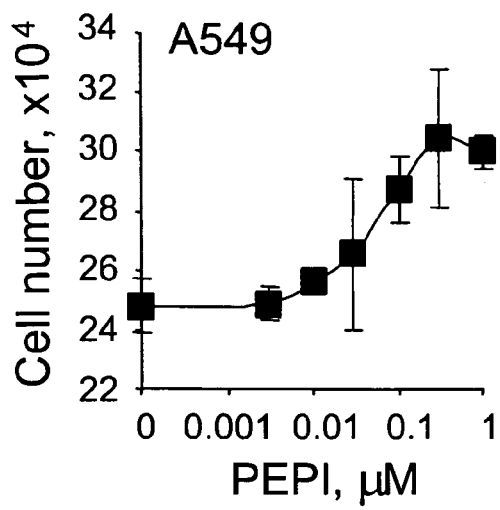
Figure 4B:
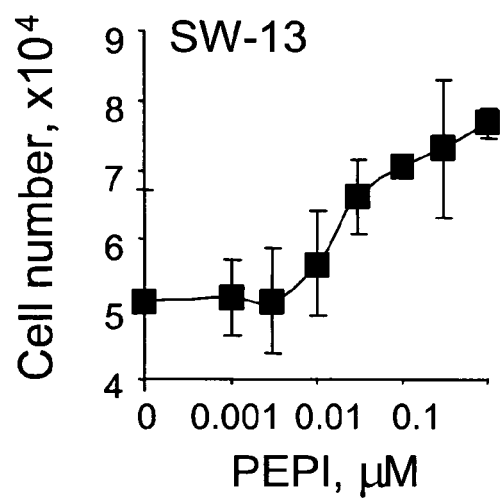
Figure 4B:
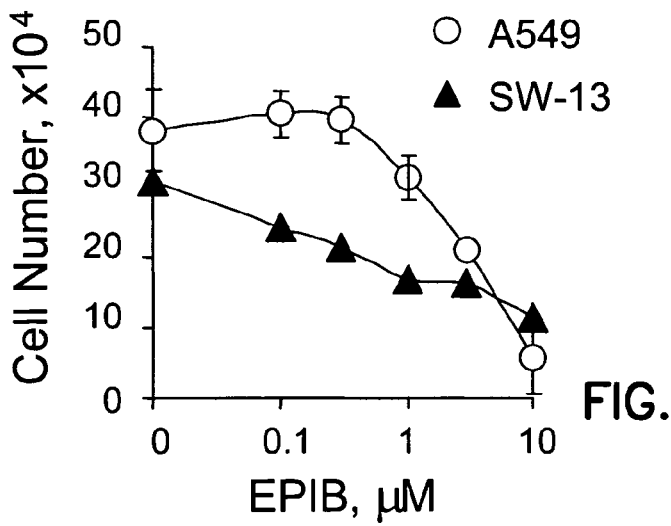

In experiments performed by the inventors, recombinant human PEPI stimulated the proliferation of two human epithelial cell lines A549 and SW-13, with 50% effective concentrations between 50-100 nM (FIG. 4A), while recombinant human EPI B inhibited the growth of the same two cell lines, with 50% inhibitory concentrations of 1-3 µM (FIG. 4B). These results indicated that the recombinant PEPI and EPI B produced as described herein was bioactive, despite the large number of disulfide bonds.

As shown in previous Examples, elastase, a neutrophil product, can convert PEPI to EPI-like fragments. Experiments were run to determine if EPIs could trigger epithelial cells to release IL-8, the major chemokine that attracts neutrophils (Baggiolini and Clark-Lewis, 1992). Indeed, both A549 and SW-13 cells produced large amounts of IL-8 in response to EPI B (FIG. 4C). Strikingly, PEPI was completely inactive in this assay. Because of a limited supply of recombinant EPIs, EPI A could not be tested and a maximally effective concentration of EPI B was not defined. However, the concentration response relationship was in the same range as for inhibition of epithelial cell proliferation (FIG. 4B).

Figure 4D:
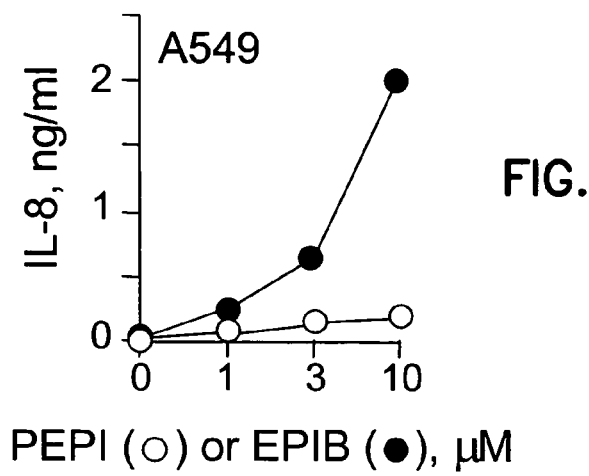
Figure 4D:
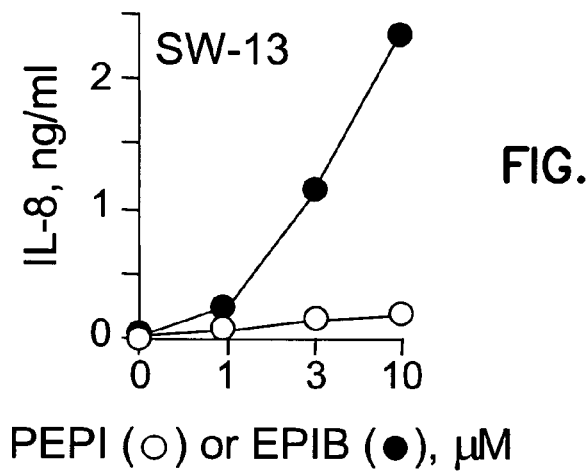
Figure 4D:
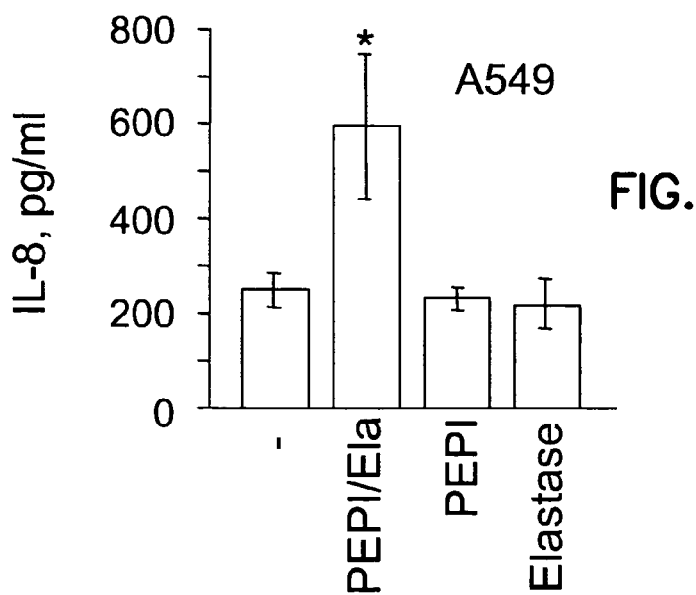

Thus, EPI B can promote epithelial cytostasis and neutrophil recruitment. In contrast, PEPI promotes epithelial proliferation without eliciting production of IL-8. IL-8 inducing activity was also observed in an elastase digest of PEPI (FIG. 4D), suggesting that at least some EPI-like bioactivity can be generated from PEPI by elastase alone.

EXAMPLE 5

Contrasting Effects of PEPI and EPIs on Neutrophils

Neutrophils adherent to proteins of extracellular matrix are triggered by inflammatory stimuli like tumor necrosis factor (TNF) to generate large quantities of reactive oxygen intermediates (ROI)(Nathan, 1987) and to release their granule contents, including elastase (Taggart et al., 2000). This Example describes experiments directed towards testing what effects PEPI, EPIs and SLPI have on the TNF-induced respiratory burst and release of proteinases by human neutrophils adherent to a surface coated with serum proteins. As a control neutrophils were also stimulated with a nonphysiologic agonist, phorbol myristate acetate (PMA).

PEPI inhibited the respiratory burst triggered by TNF (FIG. 5A, panel b). This result did not reflect interference with the phagocyte oxidase (Phox) or with the assay, because PEPI had no effect on the amount of $H_2O_2$ detected in the medium in response to PMA (FIG. 5A, panel a). In contrast to results with PEPI, neither EPI A nor B was able to block the TNF-induced respiratory burst (FIG. 5A, panel c). The triggering of adherent neutrophils by cytokines displayed a characteristic lag period involving cytoskeletal reorganization. Reagents that disrupt signaling events during the lag period can abort the respiratory burst even when added after the stimulus provided that the respiratory burst has not yet commenced (Nathan et al., 1989; Nathan, 1987). Indeed, PEPI abolished the TNF-induced respiratory burst even when added 30 min after TNF (FIG. 5B, panel b). In contrast, PEPI had no effect when added during an ongoing respiratory burst (FIG. 5B, panel c). These results suggested that PEPI inhibited neutrophil activation by perturbing intracellular signaling events initiated after TNF binds to its receptor.

Figure 5C:
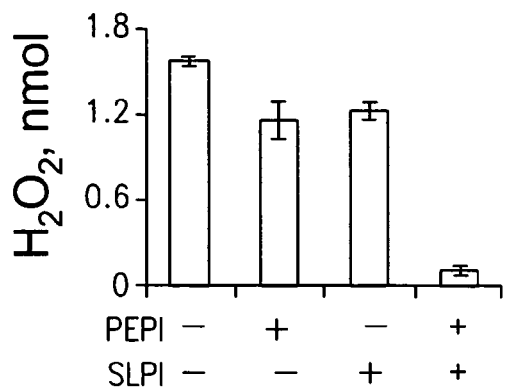

Exogenous SLPI exerts a modest inhibitory effect on the TNF-induced respiratory burst (Grobmyer et al., 2000) as illustrated in FIG. 5B (panels a and b). SLPI and PEPI augmented each other s neutrophil-inhibitory effects (FIG. 5C).

Figure 6A:
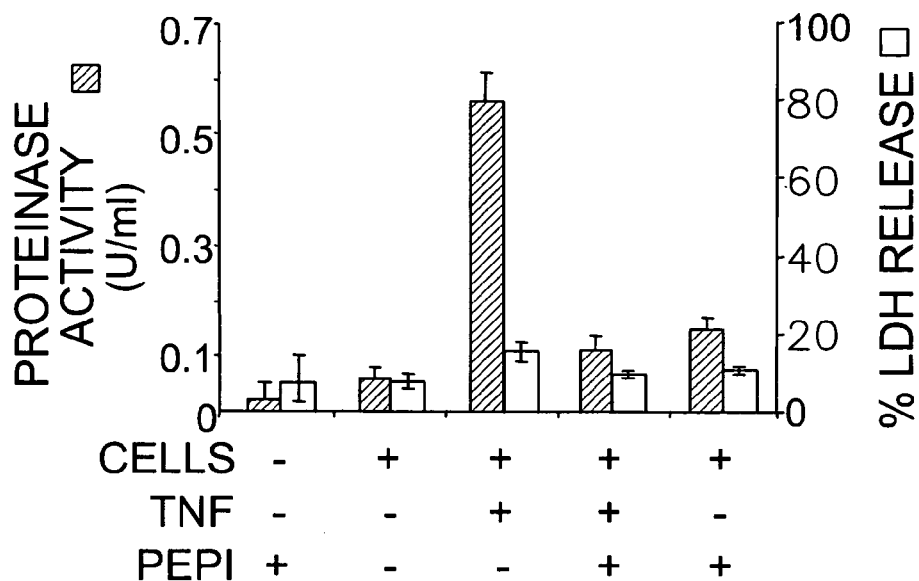
FIG. 6A-D shows that PEPI inhibits neutrophil degranulation, Pyk2 phosphorylation and spreading.
Figure 6B:
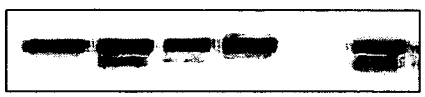

PEPI's inhibition of neutrophils may extend to preventing the release of proteinases that digest PEPI. Accordingly, the conditioned media of activated neutrophils were examined for proteinase activity. PEPI ahnost completely abolished the TNF-triggered release of casein-degrading proteinases (including elastase) from neutrophils (FIG. 6A). The conditioned media from activated neutrophils also digested PEPI, and the ability of these media to do so was inhibited both by SLPI and by the pan serine protease inhibitor diisopropyl fluorophosphate (DFP)(FIG. 6B). Of the three serine proteinases known to be released by activated PMN, cathepsin G does not digest PEPI and proteinase 3 is not inhibited by SLPI, while elastase both digests PEPI and is inhibited by SLPI. Thus, the PEPI-digesting activity released by stimulated human neutrophils was attributable to serine proteinases; PEPI blocked their release; and elastase is likely to be the major PEPI-digesting activity released by activated neutrophils.

Figure 6C:
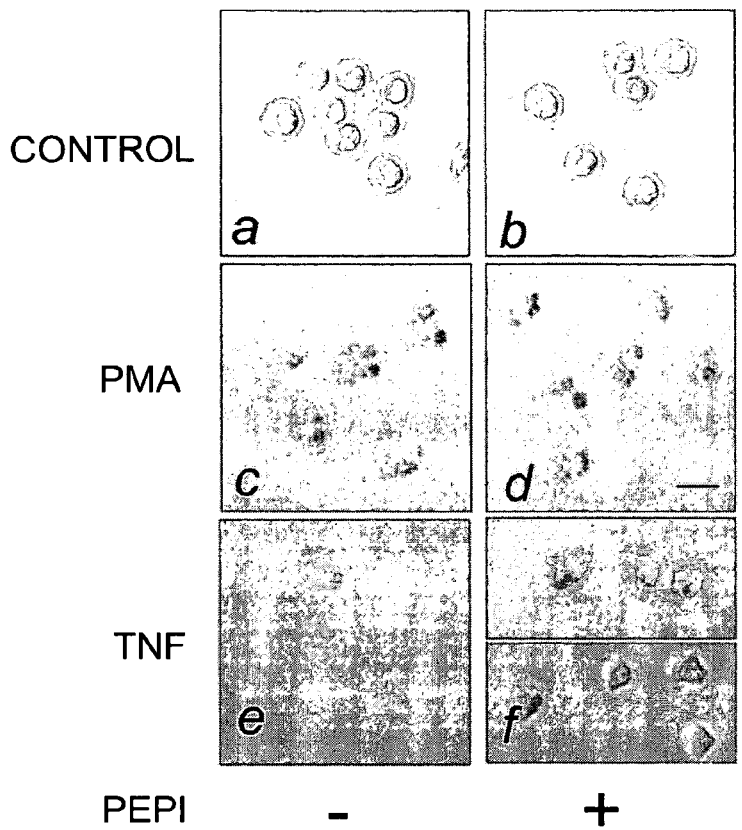

PMA and TNF trigger adherent neutrophils to spread and establish podosomes and focal adhesions in contact with the extracellular matrix (Fuortes et al., 1993), as illustrated in FIG. 6C (compare panels c and e to the control in panel a). PEPI alone had no effect on neutrophil morphology (FIG. 6C, panel b) or on the spreading elicited by PMA (FIG. 6B, panel d). However, PEPI abolished cell spreading but not cell adherence in response to TNF (FIG. 6C, panel f). These results suggest that PEPI spares early events following TNF signal transduction that lead to cell adherence but interferes with later events that lead to cell spreading, the respiratory burst and degranulation.

Figure 6D:
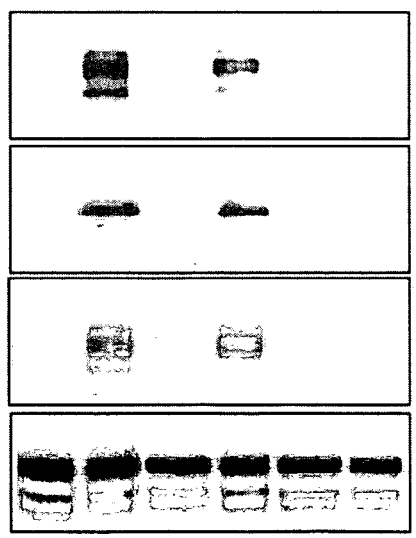

These characteristics directed attention to Pyk2, a tyrosine kinase expressed in neutrophils that appears to mediate TNF-induced cell spreading and respiratory burst (Fuortes et al., 1999). To test whether PEPI interferes with Pyk2 phosphorylation induced by TNF, neutrophils were preincubated with PEPI for 30 min before TNF stimulation. The activation of Pyk2 in the PMN lysates was detected by western blot with antibodies specific for phosphotyrosines 402, 580 and 881. PEPI (but not ovalbumin, a protein control) abolished TNF-induced tyrosine phosphorylation of Pyk2 (FIG. 6D).

Because SLPI and proepithelin are both produced constitutively by epithelial cells, they can be expected to form a complex before inflammation triggers an influx of elastase. If a given molecule of SLPI can bind proepithelin and elastase at the same time, then pre-existent SLPI-proepithelin complexes may retain the ability to inhibit elastase. This is supported by the inventor's finding that proepithelin-complexed SLPI retained the ability to protect extracellular matrix proteins fibronectin, vitronectin and collagen type I from digestion by elastase. Studies by the inventors also suggest that SLPI most likely binds PEPI at inter-BPI linker peptides, 5 of which contain negative charges. Thus, one molecule of PEPI may be decorated with several molecules of SLPI. The N-terminal domain of SLPI binds glycosaminoglycans (Mellet et al., 1995; Ying et al., 1994) and in this way SLPI may serve as a bridge to localize PEPI to epithelial surfaces. This could augment the bioactivity of PEPI. Binding to epithelial glycosaminoglycans may also position SLPI to protect the glycosaminoglycans from proteolytic shedding during inflammation (Park et al., 2000).

EXAMPLE 6

Recombinant PEPI Restores Normal Wound Healing in SLPI-Deficient Mice

SLPI-null mice have impaired healing of wounds accompanied by increased leukocyte infiltration and elevated elastase activity (Ashcroft et al., 2000). Delayed re-epithelialization is presumably related to an inability of SLPI-deficient tissues to counteract proteolysis by serine proteinases that may arise from the infiltrating leukocytes. The discovery of SLPI/PEPI/elastase axis and the dual roles of PEPI in promoting epithelialization and blocking activation of neutrophils prompted inquiry in whether endogenous PEPI is expressed during wound healing, and whether exogenous PEPI can restore normal wound healing in SLPI-null mice.

FIG. 7A shows that PEPI was constitutively expressed in mouse cutaneous tissue and that PEPI transcripts were markedly increased upon wounding, as reported for SLPI in wild type mice (Ashcroft et al., 2000). Wounding induced PEPI to the same extent in the SLPI knockout mice as in wild type mice (Fig. A).

The effect of PEPI on wound healing was assessed using a wound model described by Ashcroft et al. (2000). Four 1-cm incisional wounds were made through the skin and panniculus carnosus on the dorsum of each SLPI-null or matched wild type mouse. Immediately before wounding, the area to be incised was injected subcutaneously with recombinant rat SLPI, recombinant mouse PEPI or PBS vehicle control. Three days later, biopsies were taken across the widest portion of the wound, sectioned and analyzed by morphometry (FIG. 7B, C).

In wild type mice, application of SLPI and PEPI had no effect on the rate of healing (not shown). In contrast, the retarded healing of SLPI-deficient mice was fully normalized not only by recombinant SLPI, but just as effectively by recombinant PEPI (FIG. 7B, C). This suggested that a primary consequence of SLPI deficiency was that intact PEPI became rate-limiting for healing, despite the increase in its local synthesis.

REFERENCES

Abe, T., Kobayashi, N., Yoshimura, K., Trapnell, B. C., Kim, H., Hubbard, R. C., Brewer, M. T., Thompson, R. C., and Crystal, R. G. (1991). Expression of the secretory leukoprotease inhibitor gene in epithelial cells, J Clin Invest 87, 2207-2215.

Ashcroft, G. S., Yang, X., Glick, A. B., Weinstein, M., Letterio, J. J., Mizel, D. E., Anzano, M., Greenwell-Wild, T., Wahl, S. M., Deng, C. and Roberts, A. B. (1999). Mice lacking Smad3 show accelerated wound healing and an impaired local inflammatory response, Nat Cell Biol 1, 260-266.

Ashcroft, G. S., Lei, K., Jin, W., Longenecker, G., Kulkami, A. B., Greenwell-Wild, T., Hale-Donze, H., McGrady, G., Song, X. Y., and Wahl, S. M. (2000). Secretory leukocyte protease inhibitor mediates non-redundant functions necessary for normal wound healing, Nat Med 6,1147-1153.

Avrova, A. O., Stewart, H. E., De Jong, W. D., Heilbronn, J., Lyon, G. D., and Birch, P. R. (1999). A cysteine protease gene is expressed early in resistant potato interactions with Phytophthora infestans, Mol Plant Microbe Interact 12, 1114-1119. Baba, T., Hoff, H. B., 3rd, Nemoto, H., Lee, H., Orth, J., Arai, Y., and Gerton, G. L. (1993). Acrogranin, an acrosomal cysteine-rich glycoprotein, is the precursor of the growth-modulating peptides, granulins, and epithelins, and is expressed in somatic as well as male germ cells, Mol Reprod Dev 34, 233-243.

Baggiolini, M., and Clark-Lewis, I. (1992). Interleukin-8, a chemotactic and inflammatory cytokine, FEBS Lett 307, 97-101.

Bateman, A., Belcourt, D., Bennett, H., Lazure, C., and Solomon, S. (1990). Granulins, a novel class of peptide from leukocytes, Biochem Biophys Res Commun 173, 1161-1168.

Bateman, A., and Bennett, H. P. (1998). Granulins: the structure and function of an emerging family of growth factors, J Endocrinol 158, 145-151.

Belaaouaj, A., McCarthy, R., Baumann, M., Gao, Z., Ley, T. J., Abraham, S, N., and Shapiro, S. D. (1998). Mice lacking neutrophil elastase reveal impaired host defense against gram negative bacterial sepsis, Nat Med 4, 615-618.

Belcourt, D. R., Lazure, C., and Bennett, H. P. (1993). Isolation and primary structure of the three major forms of granulin- like peptides from hematopoietic tissues of a teleost fish (*Cyprinus carpio*), J Biol Chem 268, 9230-9237.

Bhandari, V., Palfree, R. G., and Bateman, A. (1992). Isolation and sequence of the granulin precursor cDNA from human bone marrow reveals tandem cysteine-rich granulin domains, Proc Natl Acad Sci USA 89, 1715-1719.

Carp, H., and Janoff, A. (1980). Inactivation of bronchial mucous proteinase inhibitor by cigarette smoke and phagocyte-derived oxidants, Exp Lung Res 1, 225-237. Caughey, G. H. (1994). Serine proteinases of mast cell and leukocyte granules. A league of their own, Am J Respir Crit. Care Med 150, S138-S142.

Chien, C. T., Bartel, P. L., Sternglanz, R., and Fields, S. (1991). The two-hybrid system: a method to identify and clone genes for proteins that interact with a protein of interest, Proc Natl Acad Sci USA 88, 9578-9582.

Couto, M. A., Harwig, S. S., Cullor, J. S., Hughes, J. P., and Lehrer, R. I. (1992). Identification of eNAP-1, an antimicrobial peptide from equine neutrophils, Infect Immun 60, 3065-3071.

Daniel, R., He, Z., Carmichael, K. P., Halper, J., and Bateman, A. (2000). Cellular localization of gene expression for progranulin, J Histochem. Cytochem 48, 999-1009. Del-Mar, E. G., Largman, C., Brodrick, J. W., and Geokas, M. C. (1979). A sensitive new substrate for chymotrypsin, Anal Biochem 99, 316-320.

Diaz-Cueto, L., Stein, P., Jacobs, A., Schultz, R. M., and Gerton, G. L. (2000). Modulation of mouse preimplantation embryo development by acrogranin (epithelin/granulin precursor), Dev Biol 217, 406-418.

Drew, A. F., Liu, H., Davidson, J. M., Daugherty, C. C. and Degen, J. L. (2001) Wound-healing defects in mice lacking fibrinogen, Blood 97, 3691-3698.

Eisenberg, S. P., Hale, K. K., Heimdal, P., and Thompson, R. C. (1990). Location of the protease-inhibitory region of secretory leukocyte protease inhibitor, J Biol Chem 265, 7976-7981.

Fuortes, M., Melchior, M., Han, H., Lyon, G. and Nathan, C. (1999). Role of the tyrosine kinase pyk2 in the integrin-dependent activation of human neutrophils by TNF. J Clin Invest 104: 327-335.

Grobmyer, S. R., Barie, P. S., Nathan, C. F., Fuortes, M., Lin, E., Lowry, S. F., Wright, C. D., Weyant, M. J., Hydro, L., Reeves, F., et al. (2000). Secretory leukocyte protease inhibitor, an inhibitor of neutrophil activation, is elevated in serum in human sepsis and experimental endotoxemia, Crit. Care Med 28, 1276-1282.

Grutter, M. G., Fendrich, G., Huber, R., and Bode, W. (1988). The 2.5 A X-ray crystal structure of the acid-stable proteinase inhibitor from human mucous secretions analysed in its complex with bovine alpha-chymotrypsin, Embo J 7, 345-351.

He, Z., and Bateman, A. (1999). Progranulin gene expression regulates epithelial cell growth and promotes tumor growth in vivo, Cancer Res 59, 3222-3229.

Helmig, R., Uldbjerg, N., and Ohlsson, K. (1995). Secretory leukocyte protease inhibitor in the cervical mucus and in the fetal membranes, Eur J Obstet Gynecol Reprod Biol 59, 95-101.

Hong, S. J., and Kang, K. W. (1999). Purification of granulin-like polypeptide from the blood-sucking leech, Hirudo nipponia, Protein Expr Purif 16, 340-346.

Hrabal, R., Chen, Z., James, S., Bennett, H. P., and Ni, F. (1996). The hairpin stack fold, a novel protein architecture for a new family of protein growth factors, Nat Struct Biol 3, 747-752.

Hunt, T. K. (1990). Basic principles of wound healing, J Trauma 30, S122-S128. Hutchison, D.C. (1987). The role of proteases and antiproteases in bronchial secretions, Eur J Respir Dis Suppl 153, 78-85.

Jin, F., Nathan, C. F., Radzioch, D., and Ding, A. (1998). Lipopolysaccharide-related stimuli induce expression of the secretory leukocyte protease inhibitor, a macrophage-derived lipopolysaccharide inhibitor, Infect Immun 66, 2447-2452.

Jin, F. Y., Nathan, C., Radzioch, D., and Ding, A. (1997). Secretory leukocyte protease inhibitor: a macrophage product induced by and antagonistic to bacterial lipopolysaccharide, Cell 88, 417-426.

Kramps, J. A., van Twisk, C., and van der Linden, A. C. (1983). L-Pyroglutamyl-L-prolyl-L-valine-p-nitroanilide, a highly specific substrate for granulocyte elastase, Scand J Clin Lab Invest 43, 427-432.

Lee, C. H., Igarashi, Y., Hohman, R. J., Kaulbach, H., White, M. V., and Kaliner, M. A. (1993). Distribution of secretory leukoprotease inhibitor in the human nasal airway, Am Rev Respir Dis 147, 710-716.

Martin, P. (1997). Wound healing—aiming for perfect skin regeneration, Science 276, 75-81.

Mashimo, H., Wu, D.C., Podolsky, D. K., and Fishman, M. C. (1996). Impaired defense of intestinal mucosa in mice lacking intestinal trefoil factor, Science 274, 262-265.

McElvaney, N. G., Nakamura, H., Birrer, P., Hebert, C. A., Wong, W. L., Alphonso, M., Baker, J. B., Catalano, M. A., and Crystal, R. G. (1992). Modulation of airway inflammation in cystic fibrosis. In vivo suppression of interleukin-8 levels on the respiratory epithelial surface by aerosolization of recombinant secretory leukoprotease inhibitor, J Clin Invest 90, 1296-1301.

McQuibban, G. A., Gong, J. H., Tam, E. M., McCulloch, C. A., Clark-Lewis, I., and Overall, C. M. (2000). Inflammation dampened by gelatinase A cleavage of monocyte chemoattractant protein-3, Science 289, 1202-1206.

Mellet, P., Ermolieff, J., and Bieth, J. G. (1995). Mapping the heparin-binding site of mucus proteinase inhibitor, Biochemistry 34, 2645-2652.

Nathan, C., Srimal, S., Farber, C., Sanchez, E., Kabbash, L., Asch, A., Gailit, J., and Wright, S. D. (1989). Cytokine-induced respiratory burst of human neutrophils: dependence on extracellular matrix proteins and CD11/CD18 integrins, J Cell Biol 109, 1341-1349.

Nathan, C. F. (1987). Neutrophil activation on biological surfaces. Massive secretion of hydrogen peroxide in response to products of macrophages and lymphocytes, J Clin Invest 80, 1550-1560.

Ohlsson, K., Bjartell, A., and Lilja, H. (1995). Secretory leukocyte protease inhibitor in the male genital tract: PSA-induced proteolytic processing in human semen and tissue localization, J Androl 16, 64-74.

Park, P. W., Reizes, O., and Bemfield, M. (2000). Cell surface heparan sulfate proteoglycans: selective regulators of ligand-receptor encounters, J Biol Chem 275, 29923-29926.

Plowman, G. D., Green, J. M., Neubauer, M. G., Buckley, S. D., McDonald, V. L., Todaro, G. J., and Shoyab, M. (1992). The epithelin precursor encodes two proteins with opposing activities on epithelial cell growth, J Biol Chem 267, 13073-13078.

Rappolee, D. A., and Werb, Z. (1988). Secretory products of phagocytes, Curr Opin Immunol 1, 47-55.

Rehault, S., Brillard-Bourdet, M., Juliano, M. A., Juliano, L., Gauthier, F., and Moreau, T. (1999). New, sensitive fluorogenic substrates for human cathepsin G based on the sequence of serpin-reactive site loops, J Biol Chem 274, 13810-13817.

Romer, J., Bugge, T. H., Pyke, C., Lund L. R., Flick, M. J., Degen, J. L., and Dano, K. (1996) Impaired wound healing in mice with a disrupted plasminogen gene, Nat Med 2, 287-292.

Sallenave, J. M., Si-Ta har, M., Cox, G., Chignard, M., and Gauldie, J. (1997). Secretory leukocyte proteinase inhibitor is a major leukocyte elastase inhibitor in human neutrophils, J Leukoc Biol 61, 695-702.

Shoyab, M., McDonald, V. L., Byles, C., Todaro, G. J., and Plowman, G. D. (1990). Epithelins 1 and 2: isolation and characterization of two cysteine-rich growth-modulating proteins, Proc Natl Acad Sci USA 87, 7912-7916.

Singer, A. J., and Clark, R. A. (1999). Cutaneous wound healing, N Engl J Med 341, 738-746.

Somorin, O., Tokura, S., Nishi, N., and Noguchi, J. (1979). The action of trypsin on synthetic chromogenic arginine substrates, J Biochem (Tokyo) 85, 157-162.

Song, X., Jin, W., Thompson, J., Mizel D. E., Lei, K., Billinghurst, R. C., Poole, A. R. and Whal, S. (1999). Secretory leukocyte protease inhibitor suppresses the inflammation and joint damage of bacterial cell wall-induced arthritis. J Exp Med 190, 535-542.

Sparro, G., Galdenzi, G., Eleuteri, A. M., Angeletti, M., Schroeder, W., and Fioretti, E. (1997). Isolation and N-terminal sequence of multiple forms of granulins in human urine, Protein Expr Purif 10, 169-174.

Taggart, C., Coakley, R. J., Greally, P., Canny, G., O'Neill, S. J., and McElvaney, N. G. (2000). Increased elastase release by CF neutrophils is mediated by tumor necrosis factor-alpha and interleukin-8, Am J Physiol Lung Cell Mol Physiol 278, L33-L41.

Tempst, P., Geromanos, S., Elicone, C., and Erdjument-Bromage, H. (1994). Improvements in microsequencer performance for low picomole sequence analysis. METHODS 6, 248-261.

Thompson, R. C., and Ohlsson, K. (1986). Isolation, properties, and complete amino acid sequence of human secretory leukocyte protease inhibitor, a potent inhibitor of leukocyte elastase, Proc Natl Acad Sci USA 83, 6692-6696.

van Wetering, S., van der Linden, A. C., van Sterkenburg, M. A., de Boer, W. I., Kuijpers, A. L., Schalkwijk, J., and Hiemstra, P. S. (2000). Regulation of SLPI and elafin release from bronchial epithelial cells by neutrophil defensins, Am J Physiol Lung Cell Mol Physiol 278, L51-L58.

Wahl, S. M., Worley, P., Jin, W., McNeely, T. B., Eisenberg, S., Fasching, C., Orenstein, J. M., and Janoff, E. N. (1997). Anatomic dissociation between HIV-1 and its endogenous inhibitor in mucosal tissues, Am J Pathol 150, 1275-1284.

Weinzimer, S. A., Gibson, T. B., Collett-Solberg, P. F., Khare, A., Liu, B., and Cohen, P. (2001). Transferrin is an insulin-like growth factor-binding protein-3 binding protein, J Clin Endocrinol Metab 86, 1806-1813.

Witte, M. B., and Barbul, A. (1997). General principles of wound healing, Surg Clin North Am 77, 509-528.

Wright, C. D., Kennedy, J. A., Zitnik, R. J., and Kashem, M. A. (1999). Inhibition of murine neutrophil serine proteinases by human and murine secretory leukocyte protease inhibitor, Biochem Biophys Res Commun 254, 614-617.

Xu, S. Q., Tang, D., Chamberlain, S., Pronk, G., Masiarz, F. R., Kaur, S., Prisco, M., Zanocco-Marani, T., and Baserga, R. (1998). The granulin/epithelin precursor abrogates the requirement for the insulin-like growth factor 1 receptor for growth in vitro, J Biol Chem 273, 20078-20083.

Ying, Q. L., Kemme, M., and Simon, S. R. (1994). Functions of the N-terminal domain of secretory leukoprotease inhibitor, Biochemistry 33, 5445-5450.

Zanocco-Marani, T., Bateman, A., Romano, G., Valentinis, B., He, Z. H., and Baserga, R. (1999). Biological activities and signaling pathways of the granulin/epithelin precursor, Cancer Res 59, 5331-5340.

Zhang, H., and Serrero, G. (1998). Inhibition of tumorigenicity of the teratoma PC cell line by transfection with antisense cDNA for PC cell-derived growth factor (PCDGF, epithelin/granulin precursor), Proc Natl Acad Sci USA 95, 14202-14207.

Zhang, Y., DeWitt, D. L., McNeely, T. B., Wahl, S. M., and Wahl, L. M. (1997). Secretory leukocyte protease inhibitor suppresses the production of monocyte prostaglandin H synthase-2, prostaglandin E2, and matrix metalloproteinases, J Clin Invest 99, 894-900.

Zhou, J., Gao, G., Crabb, J. W., and Serrero, G. (1993). Purification of an autocrine growth factor homologous with mouse epithelin precursor from a highly tumorigenic cell line, J Biol Chem 268, 10863-10869.

Zhu, J., and Kahn, C. R. (1997). Analysis of a peptide hormone-receptor interaction in the yeast two-hybrid system, Proc Natl Acad Sci USA 94, 13063-13068.

Zhu, J., Nathan, C., and Ding, A. (1999). Suppression of macrophage responses to bacterial lipopolysaccharide by a non-secretory form of secretory leukocyte protease inhibitor, Biochim Biophys Acta 1451, 219-223.

Zitnik, R. J., Zhang, J., Kashem, M. A., Kohno, T., Lyons, D. E., Wright, C. D., Rosen, E., Goldberg, I., and Hayday, A. C. (1997). The cloning and characterization of a murine secretory leukocyte protease inhibitor cDNA, Biochem Biophys Res Commun 232, 687-697.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

---

What is claimed is:

1. A therapeutic method comprising enhancing wound healing in a mammal afflicted with a wound comprising administering an effective amount of a composition comprising proepithelin (PEPI) to said mammal; and wherein the mammal is a secretory leukocyte protease inhibitor (SLPI) deficient mammal.

2. The method of claim 1, wherein the composition further comprises an effective amount of secretory leukocyte protease inhibitor (SLPI).

3. The method of claim 1, wherein the proepithelin comprises an amino acid sequence having any one of SEQ ID NO:1, or 2.

4. The method of claim 2, wherein the secretory leukocyte protease inhibitor comprises the amino acid sequence SEQ ID NO:7.

5. The method of claim 1, wherein the proepithelin is produced recombinantly.

6. The method of claim 5, wherein the proepithelin is encoded by a nucleic acid comprising SEQ ID NO:3.

7. The method of claim 1, wherein the mammal is a human.

8. The method of claim 1, wherein the wound involves epithelial tissue.

9. The method of claim 1 wherein the wound involves skin, respiratory tract, kidney, uterus or cervix.

10. The method of claim 1 wherein the wound involves connective tissue.

11. The method of claim 1, wherein the wound is due to surgical intervention.

12. The method of claim 1, wherein the wound is created by accidental trauma.

13. The method of claim 1, wherein the proepithelin is administered prior to creation of the wound.

14. The method of claim 2, wherein the secretory leukocyte protease inhibitor is administered prior to creation of the wound.

15. The method of claim 1, wherein the proepithelin is administered after the wound occurs.

16. The method of claim 2, wherein the secretory leukocyte protease inhibitor is administered after the wound occurs.

17. The method of claim 1, wherein the proepithelin is administered parenterally, by injection, infusion, or topical application.

18. The method of claim 2, wherein the secretory leukocyte protease inhibitor is administered parenterally, by injection, infusion, or topical application.

19. The method of claim 1, wherein the mammal also has a deficiency of endogenous proepithelin.

20. The method of claim 1, wherein the rate of wound healing is enhanced.

21. The method of claim 1, wherein inflammation is inhibited.

22. The method of claim 1, wherein the proepithelin is human proepithelin.

23. The method of claim 2, wherein the secretory leukocyte protease inhibitor is human secretory leukocyte protease inhibitor.

24. A therapeutic method comprising inhibiting inflammation in a mammal afflicted with a wound comprising administering an effective amount of a composition comprising proepithelin (PEPI) to said mammal; and wherein the mammal is a secretory leukocyte protease inhibitor (SLPI) deficient mammal.

25. The method of claim 24, wherein the composition further comprises an effective amount of secretory leukocyte protease inhibitor (SLPI).

26. The method of claim 24, wherein the proepithelin comprises an amino acid sequence having any one of SEQ ID NO:1, or 2.

27. The method of claim 25, wherein the secretory leukocyte protease inhibitor comprises the amino acid sequence SEQ ID NO:7.

28. The method of claim 24, wherein the proepithelin is produced recombinantly.

29. The method of claim 28, wherein the proepithelin is encoded by a nucleic acid comprising SEQ ID NO:3.

30. The method of claim 24, wherein the mammal is a human.

31. The method of claim 24, wherein the wound involves epithelial tissue.

32. The method of claim 24 wherein the wound involves skin, respiratory tract, kidney, uterus or cervix.

33. The method of claim 24 wherein the wound involves connective tissue.

34. The method of claim 24, wherein the wound is due to surgical intervention.

35. The method of claim 24, wherein the wound is created by accidental trauma.

36. The method of claim 24, wherein the proepithelin is administered prior to creation of the wound.

37. The method of claim 25, wherein the secretory leukocyte protease inhibitor is administered prior to creation of the wound.

38. The method of claim 24, wherein the proepithelin is administered after the wound occurs.

39. The method of claim 25, wherein the secretory leukocyte protease inhibitor is administered after the wound occurs.

40. The method of claim 24, wherein the proepithelin is administered parenterally, by injection, infusion, or topical application.

41. The method of claim 25, wherein the secretory leukocyte protease inhibitor is administered parenterally, by injection, infusion, or topical application.

42. The method of claim 24, wherein the mammal also has a deficiency of endogenous proepithelin.

43. The method of claim 24, wherein the rate of wound healing is enhanced.

44. The method of claim 24, wherein inflammation is inhibited.

45. The method of claim 24, wherein the proepithelin is human proepithelin.

46. The method of claim 25, wherein the secretory leukocyte protease inhibitor is human secretory leukocyte protease inhibitor.

* * * * *

SEQUENCE LISTING

<160> NUMBER OF SEQ ID NOS: 32

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

-continued

```
Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gly Thr Cys Cys Pro Ser Leu Gly Gly Ser Trp
    450                 455                 460
```

-continued

```
Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
            485                 490                 495

Lys Glu Val Val Ser Ala Gln Pro Ala Thr Phe Leu Ala Arg Ser Pro
                500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
        530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 2
<211> LENGTH: 593
<212> TYPE: PRT
<213> ORGANISM: Homo sapiens

<400> SEQUENCE: 2

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240
```

```
Ser Asp His Leu His Cys Cys Pro Gln Asp Thr Val Cys Asp Leu Ile
            245                 250                 255

Gln Ser Lys Cys Leu Ser Lys Glu Asn Ala Thr Thr Asp Leu Leu Thr
        260                 265                 270

Lys Leu Pro Ala His Thr Val Gly Asp Val Lys Cys Asp Met Glu Val
    275                 280                 285

Ser Cys Pro Asp Gly Tyr Thr Cys Cys Arg Leu Gln Ser Gly Ala Trp
290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
        435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 3
<211> LENGTH: 2178
<212> TYPE: DNA
<213> ORGANISM: Homo sapiens

<400> SEQUENCE: 3
gtagtctgag cgctacccgg ttgctgctgc ccaaggaccg cggagtcgga cgcaggcaga     60
ccatgtggac cctggtgagc tgggtggcct taacagcagg gctggtggct ggaacgcggt    120
```

```
gcccagatgg tcagttctgc cctgtggcct gctgcctgga ccccggagga gccagctaca      180
gctgctgccg tccccttctg gacaaatggc ccacaacact gagcaggcat ctgggtggcc      240
cctgccaggt tgatgcccac tgctctgccg ccactcctg catctttacc gtctcaggga       300
cttccagttg ctgccccttc cagaggccg tggcatgcgg ggatggccat cactgctgcc       360
cacggggctt ccactgcagt gcagacgggc gatcctgctt ccaaagatca ggtaacaact      420
ccgtgggtgc catccagtgc cctgatagtc agttcgaatg cccggacttc tccacgtgct      480
gtgttatggt cgatggctcc tggggtgct gccccatgcc ccaggcttcc tgctgtgaag       540
acagggtgca ctgctgtccg cacggtgcct tctgcgacct ggttcacacc cgctgcatca      600
cacccacggg cacccacccc ctggcaaaga agctccctgc ccagaggact aacagggcag      660
tggccttgtc cagctcggtc atgtgtccgg acgcacggtc ccggtgccct gatggttcta     720
cctgctgtga gctgcccagt gggaagtatg gctgctgccc aatgcccaac gccacctgct     780
gctccgatca cctgcactgc tgcccccaag acactgtgtg tgacctgatc cagagtaagt     840
gcctctccaa ggagaacgct accacggacc tcctcactaa gctgcctgcg cacacagtgg     900
gggatgtgaa atgtgacatg gaggtgagct gcccagatgg ctatacctgc tgccgtctac     960
agtcgggggc ctggggctgc tgcccttttta cccaggctgt gtgctgtgag gaccacatac    1020
actgctgtcc cgcgggggttt acgtgtgaca cgcagaaggg tacctgtgaa caggggcccc    1080
accaggtgcc ctggatggag aaggcccag ctcacctcag cctgccagac ccacaagcct      1140
tgaagagaga tgtcccctgt gataatgtca gcagctgtcc ctcctccgat acctgctgcc    1200
aactcacgtc tggggagtgg ggctgctgtc caatcccaga ggctgtctgc tgctcggacc    1260
accagcactg ctgcccccag ggctacacgt gtgtagctga gggcagtgt cagcgaggaa     1320 gcgagatcgt ggctggactg gagaagatgc ctgcccgccg ggcttcctta tcccacccca    1380
gagacatcgg ctgtgaccag caccagct gcccggtggg gcagacctgc tgcccgagcc      1440
tgggtgggag ctgggcctgc tgccagttgc cccatgctgt gtgctgcgag gatcgccagc    1500
actgctgccc ggctggctac acctgcaacg tgaaggctcg atcctgcgag aaggaagtgg    1560
tctctgccca gcctgccacc ttcctggccc gtagccctca cgtgggtgtg aaggacgtgg    1620
agtgtgggga aggacacttc tgccatgata ccagacctg ctgccgagac aaccgacagg     1680
gctgggcctg ctgtcctac cgccaggggc tctgttgtgc tgatcggcgc cactgctgtc    1740
ctgctggctt ccgctgcgca gccagggta ccaagtgttt gcgcagggag gccccgcgct    1800
gggacgcccc tttgagggac ccagccttga cagctgct gtgagggaca gtactgaaga     1860
ctctgcagcc ctcgggaccc cactcggagg gtgccctctg ctcaggcctc cctagcacct    1920
ccccctaacc aaattctccc tggaccccat tctgagctcc ccatcaccat gggaggtggg    1980
gcctcaatct aaggccttcc ctgtcagaag ggggttgtgt caaaagccac attacaagct    2040
gccatcccct ccccgtttca gtggaccctg tggccaggtg cttttcccta tccacagggg    2100
tgtttgtgtg tgtgcgcgtg tgcgtttcaa taaagtttgt acactttcaa aaaaaaaaaa    2160
aaaaaaaaaa aaaaaaaa                                                 2178
```

<210> SEQ ID NO 4
<211> LENGTH: 589
<212> TYPE: PRT
<213> ORGANISM: Mus musculus

<400> SEQUENCE: 4

-continued

```
Met Trp Val Leu Met Ser Trp Leu Ala Phe Ala Ala Gly Leu Val Ala
 1               5                  10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Arg Ile Thr Ser His His Leu Asp Gly Ser Cys Gln Thr His
    50                  55                  60

Gly His Cys Pro Ala Gly Tyr Ser Cys Leu Leu Thr Val Ser Gly Thr
65                  70                  75                  80

Ser Ser Cys Cys Pro Phe Ser Lys Gly Val Ser Cys Gly Asp Gly Tyr
                85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
            115                 120                 125

Gln Phe Glu Cys Pro Asp Ser Ala Thr Cys Cys Ile Met Val Asp Gly
        130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Arg Ala Val Ser Leu Pro Phe Ser Val Val Cys Pro
            195                 200                 205

Asp Ala Lys Thr Gln Cys Pro Asp Asp Ser Thr Cys Cys Glu Leu Pro
        210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
            275                 280                 285

Pro Glu Gly Tyr Thr Cys Cys Arg Leu Asn Thr Gly Ala Trp Gly Cys
        290                 295                 300

Cys Pro Phe Ala Lys Ala Val Cys Cys Glu Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Pro Trp Met Lys Lys Val Ile Ala Pro Leu Arg Leu
            340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
```

-continued

```
                420             425             430
Thr Pro Leu Gln Ile Gly Asp Ile Gly Cys Asp Gln His Thr Ser Cys
        435                 440                 445
Pro Val Gly Gln Thr Cys Cys Pro Ser Leu Lys Gly Ser Trp Ala Cys
    450                 455                 460
Cys Gln Leu Pro His Ala Val Cys Cys Glu Asp Arg Gln His Cys Cys
465                 470                 475                 480
Pro Ala Gly Tyr Thr Cys Asn Val Lys Ala Arg Thr Cys Glu Lys Asp
                485                 490                 495
Val Asp Phe Ile Gln Pro Pro Val Leu Leu Thr Leu Gly Pro Lys Val
            500                 505                 510
Gly Asn Val Glu Cys Gly Glu Gly His Phe Cys His Asp Asn Gln Thr
        515                 520                 525
Cys Cys Lys Asp Ser Ala Gly Val Trp Ala Cys Cys Pro Tyr Leu Lys
    530                 535                 540
Gly Val Cys Cys Arg Asp Gly Arg His Cys Cys Pro Gly Gly Phe His
545                 550                 555                 560
Cys Ser Ala Arg Gly Thr Lys Cys Leu Arg Lys Ile Pro Arg Trp
                565                 570                 575
Asp Met Phe Leu Arg Asp Pro Val Pro Arg Pro Leu Leu
            580                 585
```

<210> SEQ ID NO 5
<211> LENGTH: 589
<212> TYPE: PRT
<213> ORGANISM: Mus musculus

<400> SEQUENCE: 5

```
Met Trp Val Leu Met Ser Trp Leu Ala Phe Ala Ala Gly Leu Val Ala
1               5                   10                  15
Gly Thr Gln Cys Pro Asp Gly Gln Phe Cys Pro Val Ala Cys Cys Leu
            20                  25                  30
Asp Gln Gly Gly Ala Asn Tyr Ser Cys Cys Asn Pro Leu Leu Asp Thr
        35                  40                  45
Trp Pro Arg Ile Thr Ser His His Leu Asp Gly Ser Cys Gln Thr His
    50                  55                  60
Gly His Cys Pro Ala Gly Tyr Ser Cys Leu Leu Thr Val Ser Gly Thr
65                  70                  75                  80
Ser Ser Cys Cys Pro Phe Ser Lys Gly Val Ser Cys Gly Asp Gly Tyr
                85                  90                  95
His Cys Cys Pro Gln Gly Phe His Cys Ser Ala Asp Gly Lys Ser Cys
                100                 105                 110
Phe Gln Met Ser Asp Asn Pro Leu Gly Ala Val Gln Cys Pro Gly Ser
            115                 120                 125
Gln Phe Glu Cys Pro Asp Ser Ala Thr Cys Cys Ile Met Val Asp Gly
        130                 135                 140
Ser Trp Gly Cys Cys Pro Met Pro Gln Ala Ser Cys Cys Glu Asp Arg
145                 150                 155                 160
Val His Cys Cys Pro His Gly Ala Ser Cys Asp Leu Val His Thr Arg
                165                 170                 175
Cys Val Ser Pro Thr Gly Thr His Thr Leu Leu Lys Lys Phe Pro Ala
            180                 185                 190
Gln Lys Thr Asn Arg Ala Val Ser Leu Pro Phe Ser Val Val Cys Pro
        195                 200                 205
```

```
Asp Ala Lys Thr Gln Cys Pro Asp Ser Thr Cys Cys Glu Leu Pro
    210                 215                 220
Thr Gly Lys Tyr Gly Cys Cys Pro Met Pro Asn Ala Ile Cys Cys Ser
225                 230                 235                 240
Asp His Leu His Cys Cys Pro Gln Asp Thr Val Cys Asp Leu Ile Gln
                245                 250                 255
Ser Lys Cys Leu Ser Lys Asn Tyr Thr Thr Asp Leu Leu Thr Lys Leu
            260                 265                 270
Pro Gly Tyr Pro Val Lys Glu Val Lys Cys Asp Met Glu Val Ser Cys
        275                 280                 285
Pro Glu Gly Tyr Thr Cys Cys Arg Leu Asn Thr Gly Ala Trp Gly Cys
    290                 295                 300
Cys Pro Phe Ala Lys Ala Val Cys Cys Glu Asp His Ile His Cys Cys
305                 310                 315                 320
Pro Ala Gly Phe Gln Cys His Thr Glu Lys Gly Thr Cys Glu Met Gly
                325                 330                 335
Ile Leu Gln Val Pro Trp Met Lys Lys Val Ile Ala Pro Leu Arg Leu
            340                 345                 350
Pro Asp Pro Gln Ile Leu Lys Ser Asp Thr Pro Cys Asp Asp Phe Thr
        355                 360                 365
Arg Cys Pro Thr Asn Asn Thr Cys Cys Lys Leu Asn Ser Gly Asp Trp
    370                 375                 380
Gly Cys Cys Pro Ile Pro Glu Ala Val Cys Cys Ser Asp Asn Gln His
385                 390                 395                 400
Cys Cys Pro Gln Gly Phe Thr Cys Leu Ala Gln Gly Tyr Cys Gln Lys
                405                 410                 415
Gly Asp Thr Met Val Ala Gly Leu Glu Lys Ile Pro Ala Arg Gln Thr
            420                 425                 430
Thr Pro Leu Gln Ile Gly Asp Ile Gly Cys Asp Gln His Thr Ser Cys
        435                 440                 445
Pro Val Gly Gln Thr Cys Cys Pro Ser Leu Lys Gly Ser Trp Ala Cys
    450                 455                 460
Cys Gln Leu Pro His Ala Val Cys Cys Glu Asp Arg Gln His Cys Cys
465                 470                 475                 480
Pro Ala Gly Tyr Thr Cys Asn Val Lys Ala Arg Thr Cys Glu Lys Asp
                485                 490                 495
Val Asp Phe Ile Gln Pro Pro Val Leu Leu Thr Leu Gly Pro Lys Val
            500                 505                 510
Gly Asn Val Glu Cys Gly Glu Gly His Phe Cys His Asp Asn Gln Thr
        515                 520                 525
Cys Cys Lys Asp Ser Ala Gly Val Trp Ala Cys Cys Pro Tyr Leu Lys
    530                 535                 540
Gly Val Cys Cys Arg Asp Gly Arg His Cys Cys Pro Gly Gly Phe His
545                 550                 555                 560
Cys Ser Ala Arg Gly Thr Lys Cys Leu Arg Lys Ile Pro Arg Trp
                565                 570                 575
Asp Met Phe Leu Arg Asp Pro Val Pro Arg Pro Leu Leu
            580                 585

<210> SEQ ID NO 6
<211> LENGTH: 2145
<212> TYPE: DNA
<213> ORGANISM: Mus musculus

<400> SEQUENCE: 6
```

-continued

```
gagatgcctc ccagggagcc cggaccccga cgcaggcaga ccatgtgggt cctgatgagc      60
tggctggcct tcgcggcagg gctggtagcc ggaacacagt gtccagatgg gcagttctgc     120
cctgttgcct gctgccttga ccagggagga gccaactaca gctgctgtaa ccctcttctg     180
gacacatggc ctagaataac gagccatcat ctagatggct cctgccagac ccatggccac     240
tgtcctgctg gctattcttg tcttctcact gtgtctggga cttccagctg ctgcccgttc     300
tctaagggtg tgtcttgtgg tgatggctac cactgctgcc cccagggctt ccactgtagt     360
gcagatggga atcctgcttt ccagatgtca gataacccct gggtgctgt  ccagtgtcct     420
gggagccagt ttgaatgtcc tgactctgcc acctgctgca ttatggttga tggttcgtgg     480
ggatgttgtc ccatgcccca ggcctcttgc tgtgaagaca gagtgcattg ctgtccccat     540
ggggcctcct gtgacctggt tcacacacga tgcgtttcac ccacgggcac ccacacccta     600
ctaaagaagt tccctgcaca aaagaccaac agggcagtgt cttt gccttt ttctgtcgtg    660
tgccctgatg ctaagaccca gtgtcccgat gattctacct gctgtgagct acccactggg     720
aagtatggct gctgtccaat gcccaatgcc atctgctgtt ccgaccacct gcactgctgc     780
ccccaggaca ctgtatgtga cctgatccag agtaagtgcc tatccaagaa ctacaccacg     840
gatctcctga ccaagctgcc tggatacccc gtgaaggagg tgaagtgcga catggaggtg     900
agctgccctg aaggatatac ctgctgccgc ctcaacactg gggcctgggg ctgctgtcca     960
tttgccaagg ccgtgtgttg tgaggatcac attcattgct gcccggcagg gtttcagtgt    1020
cacacagaga aaggaacctg cgaaatgggt atcctccaag taccctggat gaagaaggtc    1080
atagccccc  tccgcctgcc agacccacag atcttgaaga gtgatacacc ttgtgatgac    1140
ttcactaggt gtcctacaaa caatacctgc tgcaaactca attctgggga ctggggctgc    1200
tgtcccatcc cagaggctgt ctgctgctca gacaaccagc attgctgccc tcagggcttc    1260
acatgtctgg ctcaggggta ctgtcagaag ggagacacaa tggtggctgg cctggagaag    1320
atacctgccc gccagacaac cccgctccaa attggagata tcggttgtga ccagcatacc    1380
agctgcccag tagggcaaac ctgctgccca agcctcaagg gaagttgggc ctgctgccag    1440
ctgccccatg ctgtgtgctg tgaggaccgg cagcactgtt gcccggccgg gtacacctgc    1500
aatgtgaagg cgaggacctg tgagaaggat gtcgattta  tccagcctcc cgtgctcctg    1560
accctcggcc ctaaggttgg aatgtggag  tgtggagaag gcatttctg  ccatgataac    1620
cagacctgtt gtaaagacag tgcaggagtc tgggcctgct gtccctacct aaagggtgtc    1680
tgctgtagag atggacgtca ctgttgcccc ggtggcttcc actgttcagc caggggaacc    1740
aagtgtttgc gaaagaagat tcctcgctgg gacatgtttt tgagggatcc ggtcccaaga    1800
ccgctactgt aaggaagggc tacagactta aggaactcca cagtcctggg aaccctgttc    1860
cgagggtacc cactactcag gcctccctag cgcctcctcc cctaacgtct ccccggccta    1920
ctcatcctga gtcaccctat caccatggga ggtggagcct caaactaaaa ccttctttta    1980
tggaaagaag gctgtggcca aaagcccgt  atcaaactgc catttcttcc ggtttctgtg    2040
gaccttgtgg ccaggtgctc ttcccgagcc acaggtgttc tgtgagcttg cttgtgtgtg    2100
tgtgcgcgtg tgcgtgtgtt gctccaataa agtttgtaca ctttc                    2145
```

<210> SEQ ID NO 7
<211> LENGTH: 132
<212> TYPE: PRT
<213> ORGANISM: Homo sapiens -continued

<400> SEQUENCE: 7

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130

<210> SEQ ID NO 8
<211> LENGTH: 625
<212> TYPE: DNA
<213> ORGANISM: Homo sapiens

<400> SEQUENCE: 8
agagtcactc ctgccttcac catgaagtcc agcggcctct tccccttcct ggtgctgctt        60
gccctgggaa ctctggcacc ttgggctgtg aaggctctg gaaagtcctt caaagctgga       120
gtctgtcctc ctaagaaatc tgcccagtgc cttagataca agaaacctga gtgccagagt       180
gactggcagt gtccagggaa gaagagatgt tgtcctgaca cttgtggcat caaatgcctg       240
gatcctgttg acacccccaaa cccaacaagg aggaagcctg ggaagtgccc agtgacttat      300
ggccaatgtt tgatgcttaa ccccccaat ttctgtgaga tggatggcca gtgcaagcgt       360
gacttgaagt gttgcatggg catgtgtggg aaatcctgcg tttcccctgt gaaagcttga      420
ttcctgccat atggaggagg ctctggagtc ctgctctgtg tggtccaggt cctttccacc      480
ctgagacttg gctccaccac tgatatcctc ctttggggaa aggcttggca cacagcaggc      540
tttcaagaag tgccagttga tcaatgaata aataaacgag cctatttctc tttgcaaaaa      600
aaaaaaaaaa aaaaaaaaa aaaaa                                             625

<210> SEQ ID NO 9
<211> LENGTH: 131
<212> TYPE: PRT
<213> ORGANISM: Mus musculus

<400> SEQUENCE: 9

Met Lys Ser Cys Gly Leu Leu Pro Phe Thr Val Leu Leu Ala Leu Gly
1               5                   10                  15

Ile Leu Ala Pro Trp Thr Val Glu Gly Gly Lys Asn Asp Ala Ile Lys
            20                  25                  30

Ile Gly Ala Cys Pro Ala Lys Lys Pro Ala Gln Cys Leu Lys Leu Glu
        35                  40                  45

Lys Pro Gln Cys Arg Thr Asp Trp Glu Cys Pro Gly Lys Gln Arg Cys
    50                  55                  60

```
Cys Gln Asp Ala Cys Gly Ser Lys Cys Val Asn Pro Val Pro Ile Arg
 65                  70                  75                  80

Lys Pro Val Trp Arg Lys Pro Gly Arg Cys Val Lys Thr Gln Ala Arg
                 85                  90                  95

Cys Met Met Leu Asn Pro Pro Asn Val Cys Gln Arg Asp Gly Gln Cys
            100                 105                 110

Asp Gly Lys Tyr Lys Cys Cys Glu Gly Ile Cys Gly Lys Val Cys Leu
        115                 120                 125

Pro Pro Met
    130

<210> SEQ ID NO 10
<211> LENGTH: 1123
<212> TYPE: DNA
<213> ORGANISM: Mus musculus

<400> SEQUENCE: 10
ggcacgaggg atgccaaacc cctacctaac cagaagaaga gaagaaaggc cactgccgag      60
gtcacttcca gtacttggag gagaaagcaa cgttcccatt tacagctgag taacaggagc     120
cacaaggtat gtctgactca aaagttcagg ctctcgatga ctgtgcggtg ctgcccagtg     180
tgtcttcttc aatgtaacct caggacctag aacagcacct tgcatgtgct ctcaggtggt     240
tactctgatg gcctcatggt cctgcctgaa acagaaagtc tgccacctac ttctgtagca     300
gcaagactcc tgttctgtgg ctaagcttcc tgcctgtgca agagccacag ggaggggcca     360
aatgcatgcc actggggcca cgcctcctgg taaagacata aatagtgatc ctcgggactg     420
gtcatcagag ctcccctgcc ttcaccatga agtcctgcgg ccttttacct ttcacggtgc     480
tccttgctct ggggatcctg gcaccctgga ctgtggaagg aggcaaaaat gatgctatca     540
aaatcggagc ctgccctgct aaaaagcctg cccagtgcct taagcttgag aagccacaat     600
gccgtactga ctgggagtgc ccgggaaagc agaggtgctg ccaagatgct tgcggttcca     660
agtgcgtgaa tcctgttccc attcgcaaac cagtgtggag gaagcctggg aggtgcgtca     720
aaactcaggc aagatgtatg atgcttaacc ctcccaatgt ctgccagagg acgggcagt     780 gtgacggcaa atacaagtgc tgtgagggta tatgtgggaa agtctgcctg ccccgatgt     840 gagcctgatc cctgacattg gcgccggctc tggactcgtg ctcggtgtgc tctggaaact     900
acttccctgc tcccaggcgt ccctgctccg ggttccatgg ctcccggctc cctgtatccc     960
aggcttggat cctgtggacc agggttactg ttttaccact aacatctcct tttggctcag    1020
cattcaccga tctttaggga aatgctgttg gagagcaaat aaataaacgc attcatttct    1080
ctatgcaaaa aaaaaaaaa aaaaaaaaa aaaaaaaaa aaa                         1123

<210> SEQ ID NO 11
<211> LENGTH: 39
<212> TYPE: DNA
<213> ORGANISM: Artificial Sequence
<220> FEATURE:
<223> OTHER INFORMATION: A T7 translation inititation sequence.

<400> SEQUENCE: 11
tctagaaata attttgttta actttaagaa ggagatata                             39

<210> SEQ ID NO 12
<211> LENGTH: 16
<212> TYPE: PRT
<213> ORGANISM: Homo sapiens
```

-continued

```
<400> SEQUENCE: 12

Met Trp Thr Leu Val Ser Trp Val Ala Leu Thr Ala Gly Leu Val Ala
1               5                   10                  15

<210> SEQ ID NO 13
<211> LENGTH: 41
<212> TYPE: PRT
<213> ORGANISM: Homo sapiens

<400> SEQUENCE: 13

Gly Thr Arg Cys Pro Asp Gly Gln Phe Cys Pro Val Ala Cys Cys Leu
1               5                   10                  15

Asp Pro Gly Gly Ala Ser Tyr Ser Cys Cys Arg Pro Leu Leu Asp Lys
            20                  25                  30

Trp Pro Thr Thr Leu Ser Arg His Leu
        35                  40

<210> SEQ ID NO 14
<211> LENGTH: 56
<212> TYPE: PRT
<213> ORGANISM: Homo sapiens

<400> SEQUENCE: 14

Gly Gly Pro Cys Gln Val Asp Ala His Cys Ser Ala Gly His Ser Cys
1               5                   10                  15

Ile Phe Thr Val Ser Gly Thr Ser Ser Cys Cys Pro Phe Pro Glu Ala
            20                  25                  30

Val Ala Cys Gly Asp Gly His His Cys Cys Pro Arg Gly Phe His Cys
        35                  40                  45

Ser Ala Asp Gly Arg Ser Cys Phe
    50                  55

<210> SEQ ID NO 15
<211> LENGTH: 9
<212> TYPE: PRT
<213> ORGANISM: Homo sapiens

<400> SEQUENCE: 15

Gln Arg Ser Gly Asn Asn Ser Val Gly
1               5

<210> SEQ ID NO 16
<211> LENGTH: 57
<212> TYPE: PRT
<213> ORGANISM: Homo sapiens

<400> SEQUENCE: 16

Ala Ile Gln Cys Pro Asp Ser Gln Phe Glu Cys Pro Asp Phe Ser Thr
1               5                   10                  15

Cys Cys Val Met Val Asp Gly Ser Trp Gly Cys Cys Pro Met Pro Gln
            20                  25                  30

Ala Ser Cys Cys Glu Asp Arg Val His Cys Cys Pro His Gly Ala Phe
        35                  40                  45

Cys Asp Leu Val His Thr Arg Cys Ile
    50                  55

<210> SEQ ID NO 17
<211> LENGTH: 26
<212> TYPE: PRT
<213> ORGANISM: Homo sapiens
```

-continued

```
<400> SEQUENCE: 17

Thr Pro Thr Gly Thr His Pro Leu Ala Lys Lys Leu Pro Ala Gln Arg
 1               5                  10                  15

Thr Asn Arg Ala Val Ala Leu Ser Ser Ser
             20                  25

<210> SEQ ID NO 18
<211> LENGTH: 56
<212> TYPE: PRT
<213> ORGANISM: Homo sapiens

<400> SEQUENCE: 18

Val Met Cys Pro Asp Ala Arg Ser Arg Cys Pro Asp Gly Ser Thr Cys
 1               5                  10                  15

Cys Glu Leu Pro Ser Gly Lys Tyr Gly Cys Cys Pro Met Pro Asn Ala
             20                  25                  30

Thr Cys Cys Ser Asp His Leu His Cys Cys Pro Gln Asp Thr Val Cys
         35                  40                  45

Asp Leu Ile Gln Ser Lys Cys Leu
     50                  55

<210> SEQ ID NO 19
<211> LENGTH: 19
<212> TYPE: PRT
<213> ORGANISM: Homo sapiens

<400> SEQUENCE: 19

Ser Lys Glu Asn Ala Thr Thr Asp Leu Leu Thr Lys Leu Pro Ala His
 1               5                  10                  15

Thr Val Gly

<210> SEQ ID NO 20
<211> LENGTH: 56
<212> TYPE: PRT
<213> ORGANISM: Homo sapiens

<400> SEQUENCE: 20

Asp Val Lys Cys Asp Met Glu Val Ser Cys Pro Asp Gly Tyr Thr Cys
 1               5                  10                  15

Cys Arg Leu Gln Ser Gly Ala Trp Gly Cys Cys Pro Phe Thr Gln Ala
             20                  25                  30

Val Cys Cys Glu Asp His Ile His Cys Cys Pro Ala Gly Phe Thr Cys
         35                  40                  45

Asp Thr Gln Lys Gly Thr Cys Glu
     50                  55

<210> SEQ ID NO 21
<211> LENGTH: 27
<212> TYPE: PRT
<213> ORGANISM: Homo sapiens

<400> SEQUENCE: 21

Gln Gly Pro His Gln Val Pro Trp Met Glu Lys Ala Pro Ala His Leu
 1               5                  10                  15

Ser Leu Pro Asp Pro Gln Ala Leu Lys Arg Asp
             20                  25

<210> SEQ ID NO 22
<211> LENGTH: 54
<212> TYPE: PRT
```

<213> ORGANISM: Homo sapiens

<400> SEQUENCE: 22

Val Pro Cys Asp Asn Val Ser Ser Cys Pro Ser Ser Asp Thr Cys Cys
1               5                   10                  15

Gln Leu Thr Ser Gly Glu Trp Gly Cys Cys Pro Ile Pro Glu Ala Val
            20                  25                  30

Cys Cys Ser Asp His Gln His Cys Cys Pro Gln Arg Tyr Thr Cys Val
        35                  40                  45

Ala Glu Gly Gln Cys Gln
    50

<210> SEQ ID NO 23
<211> LENGTH: 24
<212> TYPE: PRT
<213> ORGANISM: Homo sapiens

<400> SEQUENCE: 23

Arg Gly Ser Glu Ile Val Ala Gly Leu Glu Lys Met Pro Ala Arg Arg
1               5                   10                  15

Ala Ser Leu Ser His Pro Arg Asp
            20

<210> SEQ ID NO 24
<211> LENGTH: 55
<212> TYPE: PRT
<213> ORGANISM: Homo sapiens

<400> SEQUENCE: 24

Ile Gly Cys Asp Gln His Thr Ser Cys Pro Val Gly Gly Thr Cys Cys
1               5                   10                  15

Pro Ser Leu Gly Gly Ser Trp Ala Cys Cys Gln Leu Pro His Ala Val
            20                  25                  30

Cys Cys Glu Asp Arg Gln His Cys Cys Pro Ala Gly Tyr Thr Cys Asn
        35                  40                  45

Val Lys Ala Arg Ser Cys Glu
    50                  55

<210> SEQ ID NO 25
<211> LENGTH: 21
<212> TYPE: PRT
<213> ORGANISM: Homo sapiens

<400> SEQUENCE: 25

Lys Glu Val Val Ser Ala Gln Pro Ala Thr Phe Leu Ala Arg Ser Pro
1               5                   10                  15

His Val Gly Val Lys
            20

<210> SEQ ID NO 26
<211> LENGTH: 56
<212> TYPE: PRT
<213> ORGANISM: Homo sapiens

<400> SEQUENCE: 26

Asp Val Glu Cys Gly Glu Gly His Phe Cys His Asp Asn Gln Thr Cys
1               5                   10                  15

Cys Arg Asp Asn Arg Gln Gly Trp Ala Cys Cys Pro Tyr Arg Gln Gly
            20                  25                  30

Val Cys Cys Ala Asp Arg Arg His Cys Cys Pro Ala Gly Phe Arg Cys

```
              35                  40                  45
Ala Ala Arg Gly Thr Lys Cys Leu
     50                  55

<210> SEQ ID NO 27
<211> LENGTH: 20
<212> TYPE: PRT
<213> ORGANISM: Homo sapiens

<400> SEQUENCE: 27

Arg Arg Glu Ala Pro Arg Trp Asp Ala Pro Leu Arg Asp Pro Ala Leu
  1               5                  10                  15

Arg Gln Leu Leu
             20

<210> SEQ ID NO 28
<211> LENGTH: 13
<212> TYPE: PRT
<213> ORGANISM: Homo sapiens

<400> SEQUENCE: 28

Asn Ser Val Gly Ala Ile Gln Cys Pro Asp Ser Gln Phe
  1               5                  10

<210> SEQ ID NO 29
<211> LENGTH: 20
<212> TYPE: PRT
<213> ORGANISM: Homo sapiens

<400> SEQUENCE: 29

Ala Pro Ala His Leu Ser Leu Pro Asp Pro Gln Ala Leu Lys Arg Asp
  1               5                  10                  15

Val Pro Cys Asp
             20

<210> SEQ ID NO 30
<211> LENGTH: 13
<212> TYPE: PRT
<213> ORGANISM: Homo sapiens

<400> SEQUENCE: 30

Val Gly Val Lys Asp Val Glu Cys Gly Glu Gly His Phe
  1               5                  10

<210> SEQ ID NO 31
<211> LENGTH: 14
<212> TYPE: PRT
<213> ORGANISM: Homo sapiens

<400> SEQUENCE: 31

Trp Pro Thr Thr Leu Ser Arg His Leu Gly Gly Pro Cys Gln
  1               5                  10

<210> SEQ ID NO 32
<211> LENGTH: 13
<212> TYPE: PRT
<213> ORGANISM: Homo sapiens

<400> SEQUENCE: 32

Ala Ser Leu Ser His Pro Arg Asp Ile Gly Cys Asp Gln
  1               5                  10
```